US006320017B1

(12) United States Patent
Ansell

(10) Patent No.: US 6,320,017 B1
(45) Date of Patent: Nov. 20, 2001

(54) POLYAMIDE OLIGOMERS

(75) Inventor: Steven Michial Ansell, Vancouver (CA)

(73) Assignee: INEX Pharmaceuticals Corp. (CA)

( * ) Notice: Subject to any disclaimer, the term of this patent is extended or adjusted under 35 U.S.C. 154(b) by 0 days.

(21) Appl. No.: 09/218,988

(22) Filed: Dec. 22, 1998

Related U.S. Application Data

(63) Continuation of application No. 08/996,783, filed on Dec. 23, 1997.
(60) Provisional application No. 60/073,852, filed on Feb. 2, 1998.

(51) Int. Cl.⁷ .......................... C08G 69/08; C08G 73/10; A61K 9/127
(52) U.S. Cl. .......................... 528/310; 528/170; 528/322; 528/328; 528/332; 528/335; 528/336; 528/342; 424/450; 554/35; 554/36; 554/37; 554/79
(58) Field of Search .......................... 528/170, 310, 528/322, 328, 332, 335, 336, 342; 424/450; 554/35, 36, 37, 79

(56) References Cited

U.S. PATENT DOCUMENTS

| | | | |
|---|---|---|---|
| 4,426,330 | 1/1984 | Sears | 260/403 |
| 5,135,737 | 8/1992 | Keana | 424/9 |
| 5,324,844 | 6/1994 | Zalipsky | 548/520 |
| 5,356,633 | 10/1994 | Woodle et al. | 424/450 |
| 5,556,948 | * 9/1996 | Tagawa et al. | 424/178.1 |
| 5,593,622 | 1/1997 | Yoshioka et al. | 264/4.32 |
| 5,686,101 | * 11/1997 | Tagawa et al. | 424/450 |

FOREIGN PATENT DOCUMENTS

| | | | |
|---|---|---|---|
| 0 442 372 A1 | 8/1991 | (EP) | G01N/33/532 |
| 0 607 978 A1 | 7/1994 | (EP) | C07F/9/57 |
| WO90 04384 A | 5/1990 | (WO) | A61K/9/127 |
| WO94 22429 A | 10/1994 | (WO) | A61K/9/127 |

* cited by examiner

*Primary Examiner*—P. Hampton-Hightower
(74) *Attorney, Agent, or Firm*—Townsend and Townsend and Crew, LLP

(57) ABSTRACT

The present invention relates to new polyamide oligomers. These oligomers can be conjugated to lipids, nucleic acids, peptides, proteins, etc. The oligomer-lipid conjugates can be used to form liposomes, virusomes, micelles, etc., optionally containing drugs or biological agents. The polyamide oligomers are heterobifunctional allowing the attachment of other suitable ligand compounds (e.g., a targeting moiety). In addition, methods of use for the liposomes, virusomes, micelles, etc., are provided.

24 Claims, 21 Drawing Sheets

*Fig. 6a*   15  n = 3
            13  n = 7
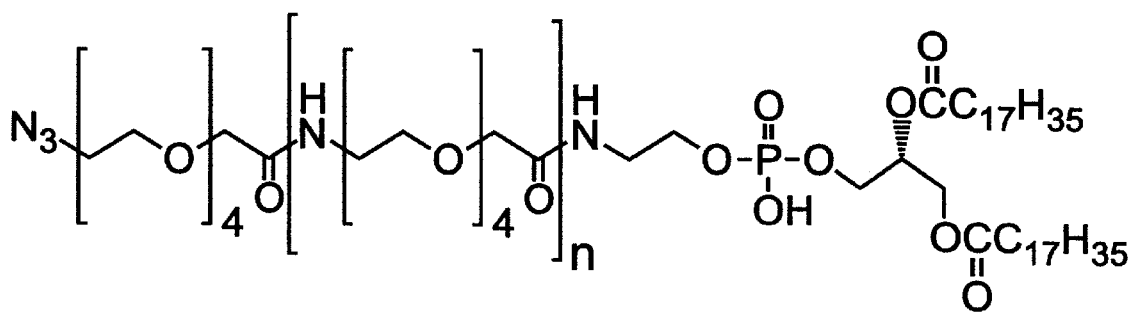
*Fig. 6b*   16  R = $C_{14}H_{29}$
            17  R = $C_{16}H_{33}$
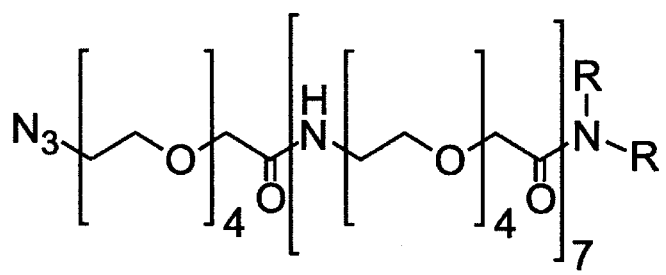
*Fig. 6c*   18  R = $C_{13}H_{27}$
            19  R = $C_{15}H_{31}$
            20  R = $C_{17}H_{35}$
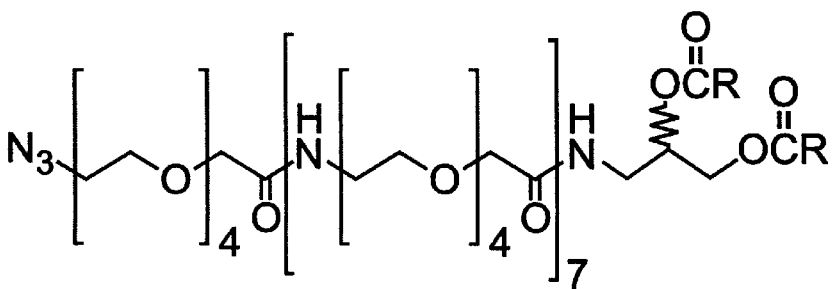

*Fig. 6d*     21   R = C$_{17}$H$_{35}$
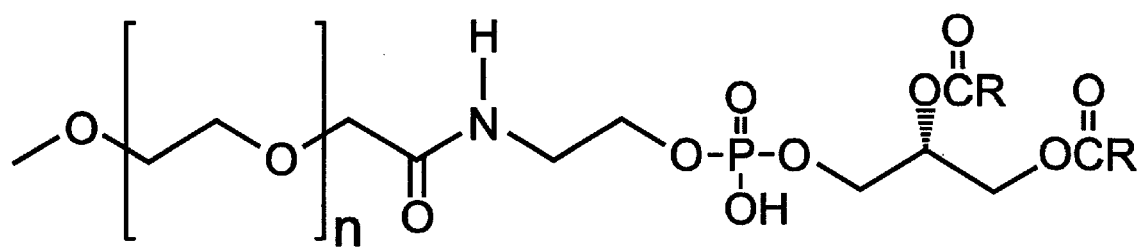
*Fig. 6e*     22   R = C$_{13}$H$_{27}$
              23   R = C$_{19}$H$_{39}$
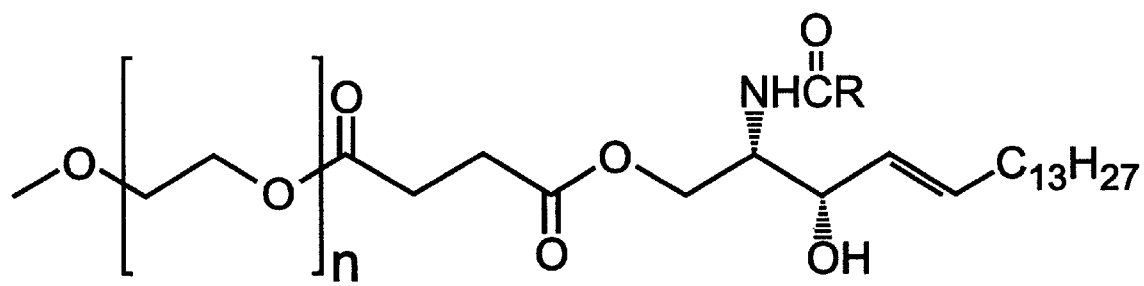

POLYAMIDE OLIGOMERS

This application claims the benefit of U.S. application Ser. No. 60/073,852, filed Feb. 2, 1998, and U.S. application Ser. No. 08/996,783, filed Dec. 23, 1997, which was converted to U.S. application Ser. No. 60/113,658 the disclosures of which are all incorporated herein by reference.

FIELD OF THE INVENTION

The present application relates to a series of polyamide oligomers based on ω-amino (oligoethyleneglycol) alkanoic acid monomers. These compounds can be used as heterobifunctional crosslinkers which can be conjugated to a variety of biomaterials which include, inter alia, proteins, nucleic acids and lipids. Oligomer-lipid conjugates of this invention can be incorporated into liposomes, micelles and other drug delivery systems for a variety of purposes.

BACKGROUND OF THE INVENTION

The pharmacokinetics of liposomal formulations can be improved if the vesicles can be maintained in circulation. An important mechanism for clearance of liposomal formulations is thought to involve the adsorption of proteins onto the liposome surface which mediates subsequent clearance by the cells of the reticuloendothelial system (RES). This clearance may be reduced by the attachment of hydrophilic polymers, such as polyethyleneglycol (PEG), to the liposome surface. These polymers may act in one or both of two ways: (i) they may inhibit or stop protein adsorption on to the liposome's surface, or (ii) they may act as a "steric barrier" to inhibit interactions between the cells involved in clearance and any proteins that might be bound to the liposome surface. The steric barrier effect may also be used to inhibit aggregation in some systems.

PEG-lipid conjugates are used in some commercial liposome formulations to create a steric barrier at the liposome surfaces. PEG is attractive because it is cheap, readily available, non immunogenic and is soluble in all but the most apolar of solvents (see, Torchlin, et al., *Biochim. Biophys. Acta.*, 1195:11–20 (1994); Parr, et al., *Biochim. Biophys. Acta.*, 1195:11–20 (1994); and Woodle, et al., *Bioconjugate Chem.*, 5:493 (1994)). The latter properties allow easy conjugation to a wide range of substrates.

U.S. Pat. No. 5,013,556 and European Patent Applications Nos. 0572 049 A2 and 0 354 855 describe liposomes bearing PEG moieties covalently linked to the external surface. As described therein, the PEG moieties are linked to amino groups in the head group of at least one phospholipid species forming the liposomes.

U.S. Pat. No. 4,426,330 describes phospholipids wherein the polar head group has been modified by covalent attachment of a PEG moiety. European Patent Application No. 0 220 797 A2 describes a process for the preparation of liposomes.

One major drawback of the use of polyethylene glycol is that it exists as a distribution of oligomers with different molecular weights. Further, batch to batch variation can occur. Thus, the properties of the PEG-bound liposomes will vary. What is needed in the art is a specific molecular weight material of defined length to allow selective properties to be imparted to liposomes or other drug delivery systems. The present invention fulfills this and other needs.

SUMMARY OF THE INVENTION

In one aspect, the present invention relates to an intrinsically heterobifunctional polyamide oligomer (PAO) of Formula I:

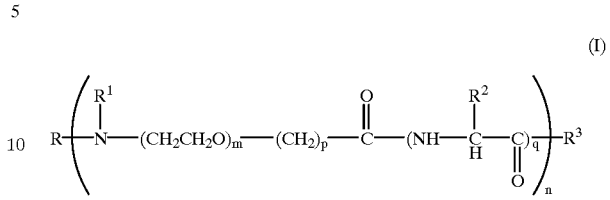

(I)

In Formula I, R is a functional group including, but not limited to, hydrogen, alkyl or acyl. $R^1$ is a functional group including, but not limited to, hydrogen or alkyl. In an alternative embodiment, R, $R^1$ and the nitrogen to which they are bound form an azido moiety. $R^2$, in Formula I, is a functional group including, but not limited to, hydrogen, optionally substituted alkyl, optionally substituted aryl or the side chain of any natural or synthetic amino acid or amino acid mimetic. $R^3$, in Formula I, is a functional group including, but not limited to, halogen, hydroxy, alkoxy, mercapto, hydrazino, amino or $NR^4R^5$, wherein $R^4$ and $R^5$ are independently hydrogen or alkyl. In Formula I, the index "n" is an integer having a value ranging from 4 to 80; the index "m" is an integer having a value ranging from 2 to 6; the index "p" is an integer having a value ranging from 1 to 4; and the index "q" is an integer having a value of 0 or 1.

The parentheses between R and $R^3$ define a monomeric unit. There are "n" monomers in any given compound of Formula I. The values of m, p and q and the definitions of $R^1$ and $R^2$ may vary from monomer to monomer for any given value of "n" monomers.

In another aspect, this invention relates to a compound of Formula II:

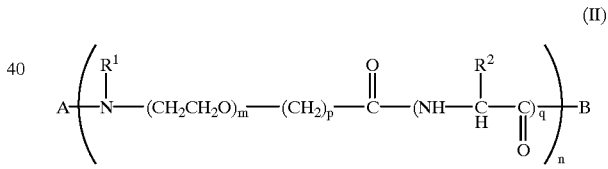

(II)

In Formula II, $R^1$ is a functional group including, but not limited to, hydrogen or alkyl. A, in Formula II, is a functional group including, but not limited to, hydrogen, alkyl, acyl or a ligand. In an alternative embodiment, $R^1$, A, and the nitrogen to which they are bound form an azido moiety. B, in Formula II, is a functional group including, but not limited to, halogen, hydroxy, alkoxy, amino, $NR^4R^5$ (wherein $R^4$ and $R^5$ are independently hydrogen or alkyl), mercapto, hydrazino, diacylglycerolyl, dialkylglycerolyl, N,N-dialkylamino, 1,2-diacyloxy-3-aminopropane, 1,2-dialkyloxy-3-aminopropane and a ligand. In Formula II, the index "n" is an integer having a value ranging from 4 to 80; the index "m" is an integer having a value ranging from 2 to 6; the index "p" is an integer having a value ranging from 1 to 4; and the index "q" is an integer having a value of 0 or 1. As described above, the parentheses between R and $R^3$ define a monomeric unit. There are "n" monomers in any given compound of Formula II. The values of m, p and q and the definitions of $R^1$ and $R^2$ can vary from monomer to monomer for any given value of "n" monomers.

In yet another aspect, this invention relates to a compound of Formula III:

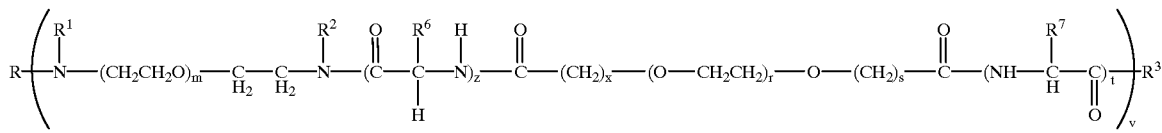

(III)

In Formula III, R is a functional group including, but not limited to, hydrogen, alkyl or aryl. $R^1$ and $R^2$ are functional groups which may be the same or different and include, but are not limited to, hydrogen or alkyl. In another embodiment, R, $R^1$ and the nitrogen to which they are bound form an azido moiety. $R^6$ and $R^7$ are functional groups which may be the same or different and include, but are not limited to, hydrogen, optionally substituted alkyl or optionally substituted aryl, wherein the substituents include aryl, amino, carboxyl, thiol or hydroxy groups or the side chain of any natural or synthetic amino acid or amino acid mimetic. The index "v" is an integer having a value ranging from 2 to 40; the indexes "m" and "r" are independently selected and have values ranging from 2 to 6; the indexes "x" and "s" are independently selected and have values ranging from 1 to 4; z and t are independently 0 or 1; and $R^3$, in Formula III, is a functional group including, but not limited to, halogen, hydrogen, alkoxy, mercapto, hydrazino, amino or $NR^4R^5$, wherein $R^4$ and $R^5$ are independently hydrogen or alkyl. The parenthesis between R and $R^3$ define a monomeric unit. $R^1$, m, $R^6$, z, x, r, $R^7$ and t can be the same or different throughout the series of "v" monomers.

In still yet another aspect, this invention relates to a compound of Formula IV:

aminopropane and a ligand. The parenthesis between A and B define a monomeric unit. $R^1$, m, $R^6$, z, x, r, $R^7$ and t can be the same or different throughout the series of "v" monomers.

In certain aspects, the present invention relates to intrinsically heterobifunctional polyamide oligomers that serve, inter alia, as a replacement to PEG, because they have superior properties. In these aspects, the oligomeric structures defined herein provide the following surprising advantages over PEG. First, unlike PEG which exists as a distribution of molecular weights, the oligomers of the present invention are of known molecular weights. Second, the present invention relates to biodegradable oligomeric material. Third, the present oligomers are intrinsically heterobifunctional bridges that can be used without the need to activate the end groups as in PEG polymers. Fourth, the present oligomers are hydrophilic, thereby providing a convenient way to keep other material in solution. There are other advantages of this invention which will be apparent to those skilled in the art.

In yet another aspect, this invention relates to a liposome, a micelle, a virosome, a lipid-nucleic acid particle, or other drug delivery composition containing a lipid conjugated to the polyamide oligomer of Formula II or Formula IV.

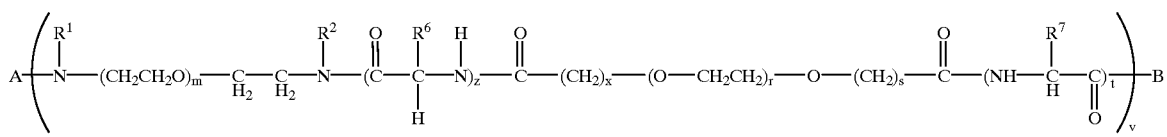

(IV)

In Formula IV, $R^1$ and $R^2$ are functional groups which may be the same or different and include, but are not limited to, hydrogen or alkyl. $R^6$ and $R^7$ in Formula IV, are functional groups which may be the same or different and include, but are not limited to, hydrogen, optionally substituted alkyl or optionally substituted aryl, wherein the substituents include aryl, amino, carboxyl, thiol or hydroxy groups or the side chain of any natural or synthetic amino acid or amino acid mimetic. The index "v" is an integer having a value ranging from 2 to 40; the indexes "m" and "r" are independently selected and have values ranging from 2 to 6; the indexes "x" and "s" are independently selected and have values ranging from 1 to 4; z and t are independently 0 or 1. A, in Formula IV, is a functional group including, but not limited to, hydrogen, alkyl, acyl or a ligand. In an alternative embodiment, $R^1$, A, and the nitrogen to which they are bound form an azido moiety. B, in Formula IV, is a functional group including, but not limited to, halogen, hydroxy, alkoxy, amino, $NR^4R^5$ (wherein $R^4$ and $R^5$ are independently hydrogen or alkyl), mercapto, hydrazino, diacylglycerolyl, dialkylglycerolyl, N,N-dialkylamino, 1,2-diacyloxy-3-aminopropane, 1,2-dialkyloxy-3-

In yet another aspect, a liposome, a micelle, a virosome, a lipid-nucleic acid particle, or other drug delivery composition contains surface-bound ligand molecules, targeting vectors, antibodies or reporter molecules to bind to specific target tissues or cells.

In another aspect, the compound of Formula II or Formula IV is a bridge, i.e., a linker molecule, with at least one ligand molecule (e.g., an antibody) covalently attached thereto. In a presently preferred embodiment, the compound of Formula II or Formula IV is a bridge with at least two ligand molecules (e.g., an antibody and a therapeutic peptide) covalently attached thereto.

In still yet another aspect, this invention relates to a liposome, a micelle, a virosome, a lipid-nucleic acid particle, or other drug delivery composition for administering a bioactive agent via the bloodstream.

In another aspect, this invention relates to a method of enhancing the blood-circulation time of liposomes, micelles, virosomes, lipid-nucleic acid particles or other lipidized drug delivery compositions administered intravenously. The enhanced circulation time is achieved by adding to the liposomes, micelles, virosomes, lipid-nucleic acid particles or other drug delivery compositions an amphipathic lipid derivatized with a compound of Formula II or Formula IV.

Other features, objects and advantages of the invention and its preferred embodiments will become apparent from the detailed description which follows.

BRIEF DESCRIPTION OF THE DRAWINGS

FIG. 6 illustrates various compounds of the present invention (A–C) and comparison compounds (D–E).

FIG. 16A: LDH levels (circles); FIG. 16B: AST levels (squares); ASL levels (triangles). Error bars represent standard deviation.

FIG. 19A illustrates human cell lines; FIG. 19B illustrates rodent cell lines.

DEFINITIONS

Figure 1:
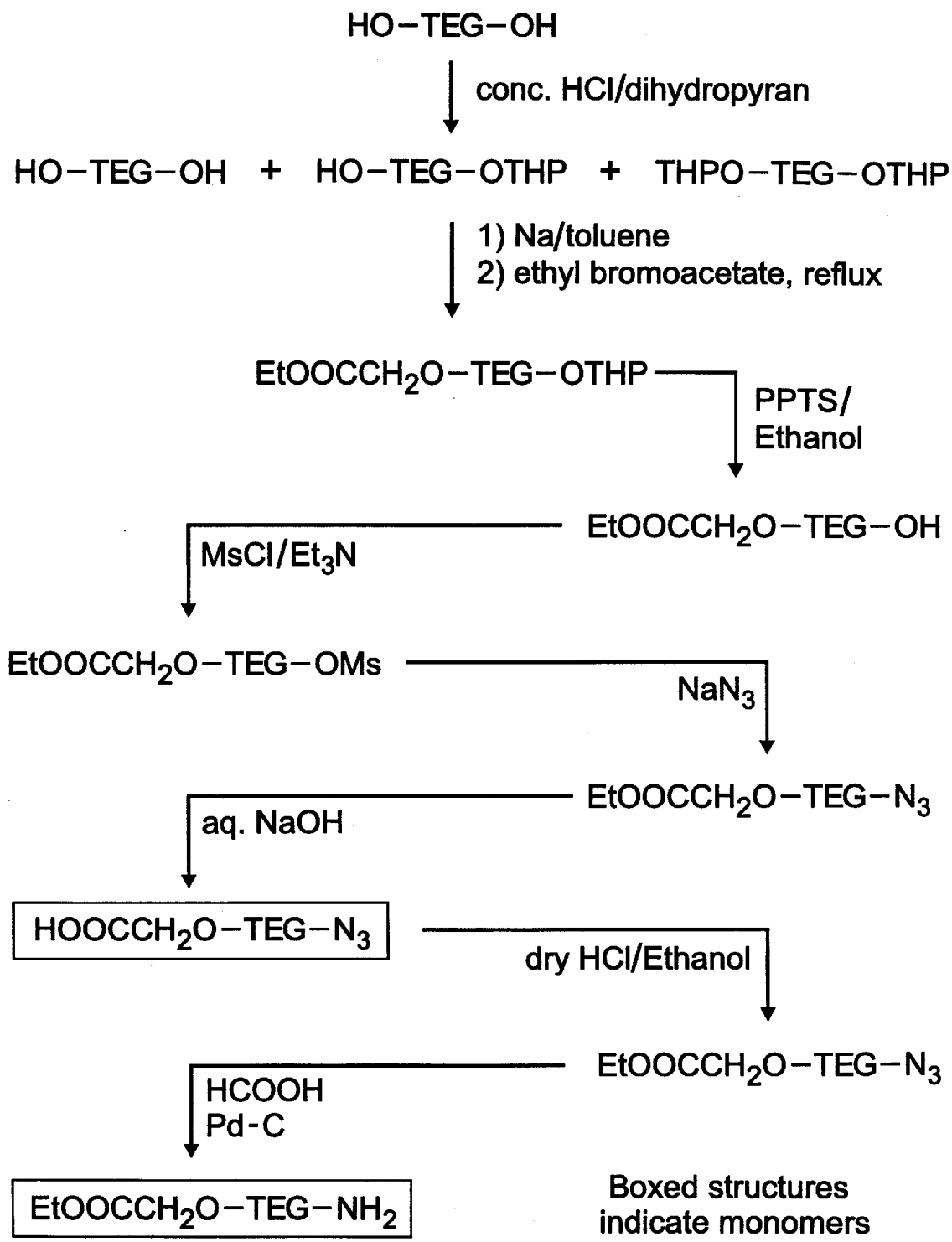
FIG. 1 illustrates the synthesis of suitable monomers exemplified by 14-amino-3,6,9,12-tetraoxatetradecanoic acid.

The term "lipid" refers to a group of organic compounds that are esters of fatty acids and are characterized by being insoluble in water but soluble in many organic solvents.

They are usually divided in at least three classes: (1) "simple lipids" which include fats and oils as well as waxes; (2) "compound lipids" which include phospholipids and glycolipids; (3) "derived lipids" such as steroids.

The term "vesicle-forming lipid" is intended to include any amphipathic lipid having a hydrophobic moiety and a polar head group, and which by itself can form spontaneously into bilayer vesicles in water, as exemplified by most phospholipids.

The term "vesicle adopting lipid" is intended to include any amphipathic lipid which is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane. Vesicle adopting lipids include lipids capable of adopting a non-lamellar phase, yet which are capable of assuming a bilayer structure in the presence of a bilayer stabilizing component. Bilayer stabilizing components include, but are not limited to, polyamide oligomers of this invention (e.g., the compounds of Formulae II and IV), peptides, proteins, detergents, lipid-derivatives, PEG coupled to phosphatidylethanolamine and PEG conjugated to ceramides (see U.S. application Ser. No.08/485,608, which is incorporated herein by reference).

The term "amphipathic lipid" refers, in part, to any suitable material wherein the hydrophobic portion of the lipid material orients into a hydrophobic phase, while a hydrophilic portion orients toward the aqueous phase. Amphipathic lipids are usually the major component of a lipid vesicle. Hydrophilic characteristics derive from the presence of polar or charged groups such as carbohydrates, phosphato, carboxylic, sulfato, amino, sulfhydryl, nitro, hydroxy and other like groups. Hydrophobicity can be conferred by the inclusion of apolar groups that include, but are not limited to, long chain saturated and unsaturated aliphatic hydrocarbon groups and such groups substituted by one or more aromatic, cycloaliphatic or heterocyclic group(s). Examples of amphipathic compounds include, but are not limited to, phospholipids, aminolipids and sphingolipids. Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine or dilinoleoylphosphatidylcholine. Other compounds lacking in phosphorus, such as sphingolipid, glycosphingolipid families, diacylglycerols and β-acyloxyacids, are also within the group designated as amphipathic lipids. Additionally, the amphipathic lipids described above may be mixed with other lipids including triglycerides and sterols.

The term "neutral lipid" refers to any of a number of lipid species which exist either in an uncharged or neutral zwitterionic form at physiological pH. Such lipids include, for example, diacylphosphatidylcholine, diacylphosphatidylethanolamine, ceramide, sphingomyelin, cephalin, cholesterol, cerebrosides and diacylglycerols.

The term "non-cationic lipid" refers to any neutral lipid as described above as well as anionic lipids. Examples of anionic lipids include, but are not limited to, phosphatidylglycerol, cardiolipin, diacylphosphatidylserine, diacylphosphatidic acid, N-dodecanoyl phosphatidylethanolamines, N-succinyl phosphatidylethanolamines, N-glutaryl phosphatidylethanolamines, lysylphosphatidylglycerols, and other anionic modifying groups joined to neutral lipids.

The term "cationic lipid" refers to any of a number of lipid species which carry a net positive charge at physiological pH. Such lipids include, but are not limited to, N,N-dioleyl-N,N-dimethylammonium chloride ("DODAC"); N-(2,3-dioleyloxy)propyl)-N, N, N-trimethylammonium chloride ("DOTMA"); N, N-distearyl-N,N-dimethylammonium bromide ("DDAB"); N-(2,3-dioleoyloxy)propyl)-N,N,N-trimethylammonium chloride ("DOTAP"); 3β-(N-(N',N'-dimethylaminoethane)-carbamoyl)cholesterol ("DC-Chol") and N-(1,2-dimyristyloxyprop-3-yl)-N,N-dimethyl-N-hydroxyethyl ammonium bromide ("DMRIE"). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine ("DOPE"), from GIBCO/BRL, Grand Island, N.Y., USA); LIPOFECTAMINE® (commercially available cationic liposomes comprising N-(1-(2,3-dioleyloxy)propyl)-N-(2-(sperminecarboxamido)ethyl)-N,N-dimnethylammonium trifluoroacetate ("DOSPA") and ("DOPE"), from GIBCO/BRL); and TRANSFECTAM® (commercially available cationic lipids comprising dioctadecylamidoglycyl carboxyspermine ("DOGS") in ethanol from Promega Corp., Madison, Wis., USA).

The term "fusogenic" refers to the ability of a liposome or other drug delivery system to fuse with membranes of a cell. The membranes can be either the plasma membrane or membranes surrounding organelles, e.g., endosome, nucleus, etc. "Fusogenesis" is the fusion of a liposome to such a membrane.

The term "dendrimer" includes reference to branched polymers which possess multiple generations. In dendrimers, each generation creates multiple branch points.

The term "ligand" includes any molecule, compound or device with a reactive functional group and includes lipids, amphipathic lipids, carrier compounds, bioaffinity compounds, biomaterials, biopolymers, biomedical devices, analytically detectable compounds, therapeutically active compounds, enzymes, peptides, proteins, immune stimulators, radiolabels, fluorogens, biotin, drugs, haptens, DNA, RNA, polysaccharides, liposomes, virosomes, micelles, immunoglobulins, functional groups or toxins. The foregoing list is not intended to be exhaustive.

As used herein, the term "alkyl" denotes branched or unbranched hydrocarbon chains, such as, methyl, ethyl, n-propyl, iso-propyl, n-butyl, sec-butyl, iso-butyl, tertbutyl, octa-decyl and 2-methylpentyl. These groups can be optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoromethyl, 3-hydroxyhexyl, 2-carboxypropyl, 2-fluoroethyl, carboxymethyl, cyanobutyl and the like.

The term "alkylene" refers to a divalent alkyl as defined above, such as methylene ($—CH_2—$), propylene ($—CH_2CH_2CH_2-$), chloroethylene ($—CHClCH_2—$), 2-thiobutene $—CH_2\ CH(SH)CH_2CH_2$, 1-bromo-3-hydroxyl-4-methylpentene ($—CHBrCH_2CH(OH)CH(CH_3)CH_2—$), and the like.

The term "alkenyl" denotes branched or unbranched hydrocarbon chains containing one or more carbon-carbon double bonds.

The term "alkynyl" refers to branched or unbranched hydrocarbon chains containing one or more carbon-carbon triple bonds.

The term "aryl" denotes a chain of carbon atoms which form at least one aromatic ring having preferably between about 6–14 carbon atoms, such as phenyl, naphthyl, indenyl, and the like, and which may be substituted with one or more functional groups which are attached commonly to such chains, such as hydroxyl, bromo, fluoro, chloro, iodo, mercapto or thio, cyano, cyanoamido, alkylthio, heterocycle, aryl, heteroaryl, carboxyl, carbalkoyl, alkyl, alkenyl, nitro, amino, alkoxyl, amido, and the like to form aryl groups such as biphenyl, iodobiphenyl, methoxybiphenyl, anthryl, bromophenyl, iodophenyl, chlorophenyl, hydroxyphenyl, methoxyphenyl, formylphenyl, acetylphenyl, trifluoromethylthiophenyl, trifluoromethoxyphenyl, alkylthiophenyl, trialkylammoniumphenyl, amidophenyl, thiazolylphenyl, oxazolylphenyl, imidazolylphenyl, imidazolylmethylphenyl, and the like.

The term "acyl" denotes the —C(O)R group, wherein R is alkyl or aryl as defined above, such as formyl, acetyl, propionyl, or butyryl.

The term "ethoxyacetyl" denotes —C(O)CH$_2$COCH$_2$CH$_3$.

The term "alkoxy" denotes —OR—, wherein R is alkyl.

The term "amido" denotes an amide linkage: —C(O)NR— (wherein R is hydrogen or alkyl).

The term "amino" denotes an amine linkage: —NR—, wherein R is hydrogen or alkyl.

The term "carboxyl" denotes —C(O)O—, and the term "carbonyl" denotes —C(O)—.

The term "carbonate" indicates —OC(O)O—.

The term "carbamate" denotes —NHC(O)O—, and the term "urea" denotes —NHC(O)NH—.

The term "phosphoro" denotes —OP(O)(OH)O—.

The term "azido" denotes —N$_3$.

The term "side chain" of amino acids denotes the R group bonded to the α-carbon of naturally-occurring amino acids as well as synthetic amino acids and/or or amino acid mimetics. This group includes, but is not limited to, hydrogen (glycine); methyl (alanine); isopropyl (valine); isobutyl (leucine); secbutyl (isoleucine); hydroxymethyl (serine); benzyl (phenylalanine); and the like.

The term "diacylglycerolyl" denotes 2-fatty acyl chains, $R^1$ and $R^2$ having independently between 2 and 30 carbons bonded to the 1- and 2-position of glycerol by ester linkages. The acyl groups can be saturated or have varying degrees of unsaturation. Diacylglycerolyls have the following general formula:

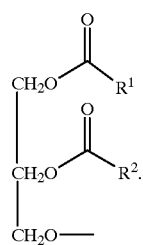

The term "dialkylglycerolyl" denotes two C$_1$–C$_{30}$ alkyl chains bonded to the 1- and 2-position of glycerol by ether linkages. Dialkylglycerolyls have the following general formula:

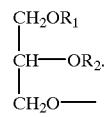

The term "N-N-dialkylamino" denotes

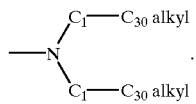

The term "1,2-diacyloxy-3-aminopropane" denotes 2-fatty acyl chains C$_1$–C$_{30}$ bonded to the 1- and 2-position of propane by an ester linkage. The acyl groups can be saturated or have varying degrees of unsaturation. The 3-position of the propane molecule has a —NH— group attached. 1,2-diacyloxy-3-aminopropanes have the following general formula:

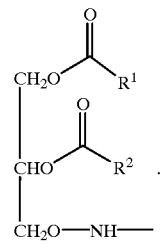

The term "1,2-dialkyl-3-aminopropane" denotes 2-alkyl chains (C$_1$–C$_{30}$) bonded to the 1- and 2-position of propane by an ether linkage. The 3-position of the propane molecule has a —NH— group attached. 1,2-dialkyl-3-aminopropanes have the following general formula:

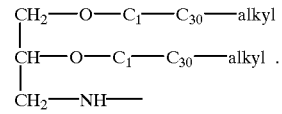

DETAILED DESCRIPTION OF THE INVENTION AND PREFERRED EMBODIMENTS

A. Compounds and Oligomer Synthesis

The present invention relates to an intrinsically heterobifunctional polyamide oligomer (PAO) of Formula I:

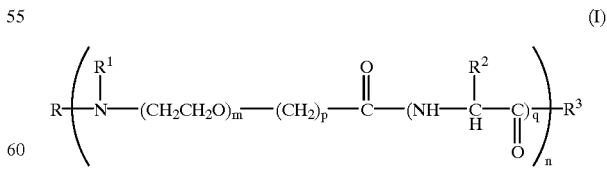

(I)

wherein: R, $R^1$, $R^2$, $R^3$, m, p, q and n have been previously defined.

Polyamide oligomers of Formula I can be prepared by the repeated dimerization of suitable monomers having the following general formula:

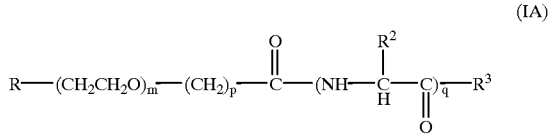

(IA)

wherein: R is $NH_2$, $NR^4R^5$ (wherein $R^4$ and $R^5$ may be the same or different and are selected from group consisting of hydrogen, alkyl, acyl or any protecting group for an amino function), $N_3$, $NO_2$, CN or any other functional group which can be reduced to an amino function; $R^2$ is hydrogen, optionally substituted alkyl, optionally substituted aryl or the side chain of any natural or synthetic amino acid or amino acid mimetic; m is 2 to 6; p is 1 to 4; q is 0 or 1; and $R^3$ is hydroxy or alkoxy.

Examples of suitable amino protecting groups are well known to those skilled in the art and include those described in Greene, W., et al., *Protective Groups in Organic Synthesis*, 2nd Edition (1991), Wiley Interscience, New York.

Figure 2:
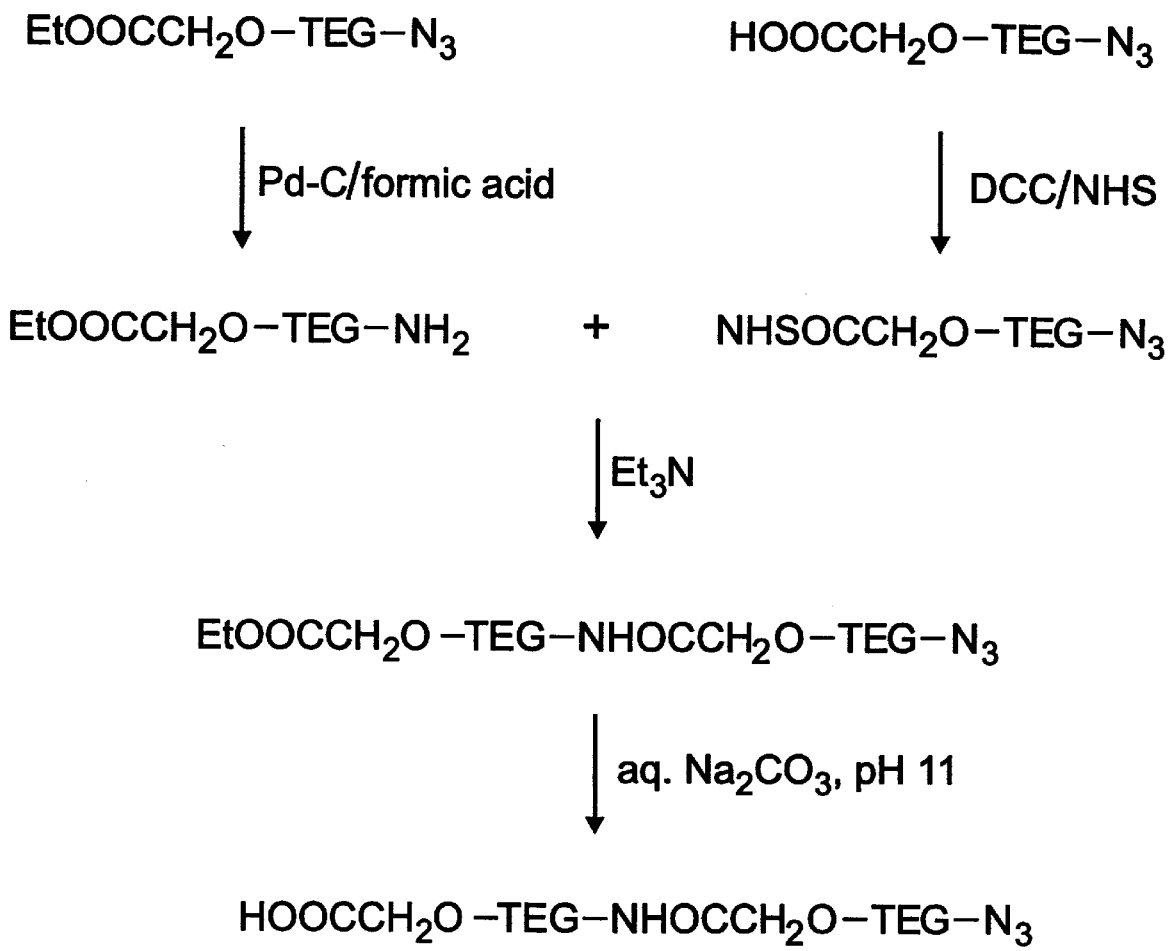
FIG. 2 illustrates the synthesis of a claimed oligomer exemplified by octa-(14-amino-3,6,9,12-tetraoxatetradecanoic acid)

One preferred embodiment of a monomeric compound of Formula IA is the embodiment wherein m is 4, p is 1, q is 0, R is $N_3$ and $R^3$ is $OCH_2CH_3$. This monomer can be activated for dimerization either by deprotection of the acyl group in which case basic hydrolysis yields the analogue in which $R^3$ is OH or, alternatively, by reduction of the $N_3$ group to a $NH_2$ group under conditions which do not favor hydrolysis of $R^3$. Suitable conditions are well known to those skilled in the art (see, e.g., Hudlicky, M. (1996) *Reductions in Organic Chemistry*, 2nd Edition, American Chemical Society, Washington, 100, the teachings of which are incorporated herein by reference). In a presently preferred embodiment, the reduction is effected by treatment of the azide with palladium-carbon in the presence of formic acid. Suitably deprotected monomers with complementary reactivity can then be dimerized to form an amide bond using methods which are commonly applied to the formation of peptides and are well known to those skilled in the art (see, e.g., Bodansky, M., et al., *Principles of Peptide Synthesis*, 2nd Edition (1993), Springer-Verlag Inc., New York, the teachings of which are incorporated herein by reference). In a preferred embodiment, this dimerization is performed by first activating the free acid in which R is $N_3$ and $R^3$ is OH using N-hydroxysuccinimide (NHS) and N,N-dicyclohexylcarbodiimide (DCC), and then adding the free base in which R is $NH_2$ and $R^3$ is OEt in the presence of triethylamine. The dimerized material thus prepared can then be used as one of the precursors in a subsequent dimerization using the same methods as described above. It will be readily apparent to those skilled in the art that repetition of this dimerization procedure using suitable precursors can be used to assemble a wide range of possible oligomers. In one preferred embodiment, monomers of Formula IA, in which m is 4, p is 1, q is 0, R is $N_3$ and $R^3$ is OEt, are subjected to three dimerization cycles (see, FIG. 2) to produce the octamer of Formula I, wherein n is 8, m is 4, p is 1, q is 0, $R^1$ is hydrogen, R is $N_3$ and $R^3$ is OEt for all of the monomeric units. Again, however, it will be readily apparent to those of skill in the art that the values of m, p and q and the definitions of $R^1$ and $R^2$ can vary from monomer to monomer for any given value of "n" monomers.

In yet another preferred embodiment, a monomer of Formula IA, in which m is 4, p is 1, q is 0, R is NHtBOC (tBOC=tert-butoxycarbonyl) and $R^3$ is OEt, can be employed in forming the oligomers of Formula I. In this embodiment, deprotection of the amine is effected by treatment with triflouroacetic acid. Dimerization is then effected as described above. It will be clear to those skilled in the art that a great many latent amines, protected amines or protected carboxylic acid groups can be utilized for the generation of suitable monomers and still remain within the orbit of the invention.

Monomers of Formula IA can be prepared from oligo-ethyleneglycols in a number of ways which will be readily apparent to those skilled in the art. Oligo-ethyleneglycols ranging from diethylene glycol to hexaethylene glycol are available commercially. Higher order oligo-ethyleneglycols can be synthesized by methods known in the art (see, e.g., Keegstra, et al., *Journal of Organic Chemistry*, 57:6678 (1992)).

In a preferred embodiment, tetraethylene glycol is used as the precursor as illustrated in FIG. 1. Tetraethylene glycol (TEG) is treated with one half equivalent of dihydropyran and the mono-protected TEG (TEG-mTHP) is isolated. The TEG-mTHP is then treated with an excess of sodium, followed by ethyl bromoacetate. Deprotection of the tetrahydropyran group is effected by treatment with pyridinyl p-toluenesulfonate salt in ethanol. Treatment of the product with methane sulfonyl chloride, followed by sodium azide or a suitable latent amino reagent, such as potassium phthalimide or ammonia, generates a suitable monomer. Protection or deprotection of the amino or carboxyl groups may be required. It will be readily apparent to those skilled in the art that this strategy can be used with a wide range of protecting groups, activating agents and alkylating agents without departing from the scope of the invention. Some specific examples of these methods are described in PCT Publication WO 92/01474, the teachings of which are incorporated herein by reference.

In another embodiment, a large excess of TEG can be treated directly with sodium, followed by ethyl bromoacetate. Subsequent manipulation would proceed by treatment with methane sulfonyl chloride, followed by methods as discussed above.

In more general embodiments, it may be desirable to include "α-amino acids" as crosslinkers between some or all of the monomeric units of the oligomers of the present invention. This embodiment corresponds to a compound of Formula I, wherein q is 1 for some or all of the monomers for any given value of "n" monomers. Suitable amino acids include all known naturally-occurring amino acids, as well as other amino acids and amino acid mimetics which have been prepared synthetically.

It will be immediately apparent to those skilled in the art that the versatility of the present method allows amide bond formation to take place with monomers having varying amounts of ethylene glycol units. Although the foregoing example has been described with the synthesis of TEG units, synthesis of molecules having varying numbers of ethylene glycol units on either side of an amide bond is possible, i.e., for embodiments of Formula I wherein "m" can have different values in the range of 2 to 6 for all of the monomeric units for any given value of "n" monomers.

An alternative embodiment of this invention relates to PAO oligomers of Formula III:

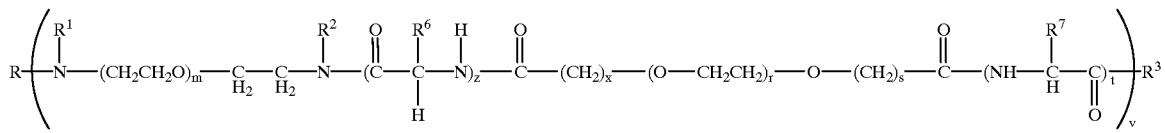

(III)

wherein: R is hydrogen, alkyl or aryl; $R^1$ and $R^2$ are independently selected and are hydrogen or alkyl; $R^6$ and $R^7$ are independently selected and are hydrogen, optionally substituted alkyl or optionally substituted aryl, wherein the substituents include aryl, amino, carboxyl, thiol or hydroxy groups or the side chain of any natural or synthetic amino acid or amino acid mimetic; $R^3$ is halogen, hydrogen, alkoxy, mercapto, hydrazino, amino or $NR^4R^5$, wherein $R^4$ and $R^5$ are independently hydrogen or alkyl. Alternatively, R, $R^1$ and the nitrogen to which they are bound form an azido moiety. The index "v" is an integer having a value ranging from 2 to 40; the indexes "m" and "r" are independently selected and have values ranging from 2 to 6; the indexes "x" and "s" are independently selected and have values ranging from 1 to 4; z and t are independently 0 or 1. The parenthesis between R and $R^3$ define a monomeric unit. As described above, $R^1$, m, $R^6$, z, x, r, $R^7$ and t can be the same or different throughout the series "v" of monomers.

One approach to the synthesis of PAO of Formula III involves the mono-protection of a hydrophilic diamine and diacid with subsequent condensation. The diamine is a compound of Formula IIIA,

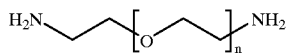

(IIIA)

wherein: the index "n" has a value ranging from 2 to 6, and the diacid is a compound of Formula IIIB:

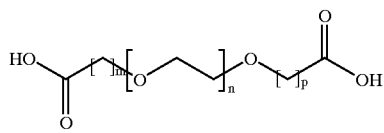

(IIIB)

wherein: the index "n" has a value ranging from 2 to 6, and the indexes "m" and "p" are independently selected and have values ranging from 1 to 4. Condensation of the unprotected amino and carboxylic acid groups form an amide bond.

Although the range of values of m in FIG. IA and n in FIGS. IIIA and IIIB are from about 2 to about 6, it will be apparent to those skilled in the art that smaller or larger values of m and n will be acceptable provided the molecules retain their chemical and physical properties.

Procedures for the formation of amide bonds are well known in the art (see, e.g., Bodansky, M., et al., *Principles of Peptide Synthesis*, 2nd Edition, Springer-Verlag Inc., New York (1993)). By using such procedures, the resulting conjugate has protected amino and carboxylic acid functionalities. Selective deprotection of one or the other of these protective groups generates a suitable precursors for the next dimerization cycle. Many methods have been published for the protection and deprotection of amino and carboxylic acid groups (see, e.g., Greene, W., et al., *Protective Groups in Organic Synthesis*, 2nd Edition, Wiley Interscience, New York (1991)). The mono-protected monomers are prepared by treating the monomer with a 1:1 mole ratio of a protecting agent. This process will generate a mixture of unprotected, mono-protected and di-protected monomers. The mono-protected monomer can then be isolated by conventional procedures known to those skilled in the art. Another method for producing a mono-protected monomer involves the selective introduction of a latent amine or carboxyl group. Such functional groups can then be converted to the amine or carboxylic acid groups by chemical means. Examples are azido (see, Bertozzi, et. al., *Journal of Organic Chemistry* 56:4326 (1991)) or nitrile groups in the case of amines, and hydroxy groups in the case of carboxylic acids. Introduction and chemical conversion of such groups can be achieved using well known methods (see, March, J., *Advanced Organic Chemistry*, 3rd Edition, Wiley Interscience, New York (1985), the teachings of which are incorporated herein by references).

The PAOs of this invention also include dendrimers. The branching point can occur at $R^2$ in Formulae I, IA and II. In Formulae III and IV, the branch point can occur at $R^6$ and $R^7$. In dendrimers, each generation creates multiple branch points.

B. Reaction of the Olilomer With a Suitable Liland(s)

In another preferred embodiment of this invention, the polyamide oligomer acts as a heterobifunctional bridge. In this respect, this invention relates to a compound having the general formula:

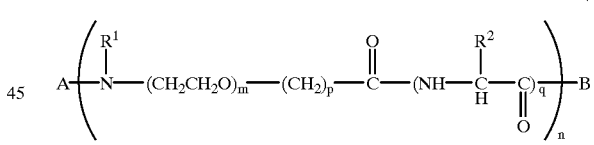

(II)

wherein: A, $R^1$, $R^2$, B, m, p, q and n have been defined above.

The attachment of a covalent ligand(s) (i.e., A or B, or A and B) to the polyamide oligomer is made on at least one side of the compound. Any compound which can react with one side of the PAO can be used as a ligand. Suitable ligands include, but are not limited to, lipids, amphipathic lipids, carrier compounds, bioaffinity compounds, biomaterials, biopolymers, biomedical devices, analytically detectable compounds, therapeutically active compounds, enzymes, peptides, proteins, immune stimulators, radiolabels, fluorogens, biotin, drugs, haptens, DNA, RNA, polysaccharides, liposomes, micelles, immunoglobulins, functional groups or toxins. Antibodies of various classes and subclasses and various specificity can also be used as ligands. Suitable biomaterials include, but are not limited to, stents, catheters and other devices. The PAOs of this invention are suitable replacements for polymers used in other mammalian systems.

In one preferred embodiment, an amphiphilic lipid is covalently attached as ligand B. In this embodiment, A is a functional group such as hydrogen, alkyl or acyl or other suitable ligand (e.g., a targeting molecule). Suitable amphiphilic lipids which can be covalently attached as ligand B include, but are not limited to, phospholipids with a reactive functionality such as phosphatidylethanolamines (PE), aminolipids, dialkylamines, diacylglycerols, dialkylglycerols, diacyloxypropanamines, dialkyloxypropanamines, and cholesterol. Suitable amphipathic lipids with a reactive functionality can be found among neutral, cationic and non-cationic lipids. Such lipids are preferably amphipathic vesicle-forming or vesicle adopting lipids having two hydrocarbon chains, typically acyl chains and a polar head group. The hydrocarbon chains are typically between 8–22 carbons in length and can be saturated or unsaturated. Hydrocarbon chains having between 14–18 carbons are especially preferred.

Typically, the PAO-lipid conjugates of the present invention are prepared by derivatization of the polar head groups of the phospholipids, such as diacylglycerophospholipids. An example of a diacylglycerophospholipid which can be conjugated to PAO includes, but is not limited to, distearoyl phospatidylethanolamine (DSPE). The phospholipids usually contain two acyl chains bonded to the 1- and 2-positions of glycerol by ester linkages. Preferably, the PAO is linked to an amino group in the head group of at least one phospholipid species forming a liposome.

the other on the PAO. For example, when R and $R^1$ of Formula I are both hydrogen, thus forming an amine, this functional group can be reacted with a ligand (A) with an activated carboxyl group, such as an acyl chloride or NHS ester, to form an amide. By suitable choice of reactive groups, the desired coupling will be obtained.

A convenient method to attach proteins to a PAO as ligand A is via a carbamate linkage. U.S. Pat. No. 5,324,844, incorporated herein by reference, describes the use of the functional group succinidyl carbonate to attach proteins, and this method is also applicable to the compounds described herein.

It will be immediately obvious to a person skilled in the art that conventional peptide chemistry which results in either activation or protection of amino and carboxylic acid groups is applicable herein (see, e.g., Bodansky, M., et al., *Principles of Peptide Synthesis,* 2nd Edition, Springer-Verlag Inc., New York (1993)). By using these conventional procedures, selective protection and activation of either side of the PAO can be accomplished. Subsequent deprotection or activation can then proceed as described above.

Compounds of Formula III can also act as a heterobifunctional bridge. This generates a compound of Formula IV:

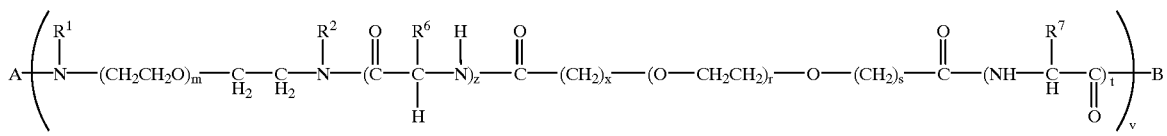

(IV)

Figure 3:
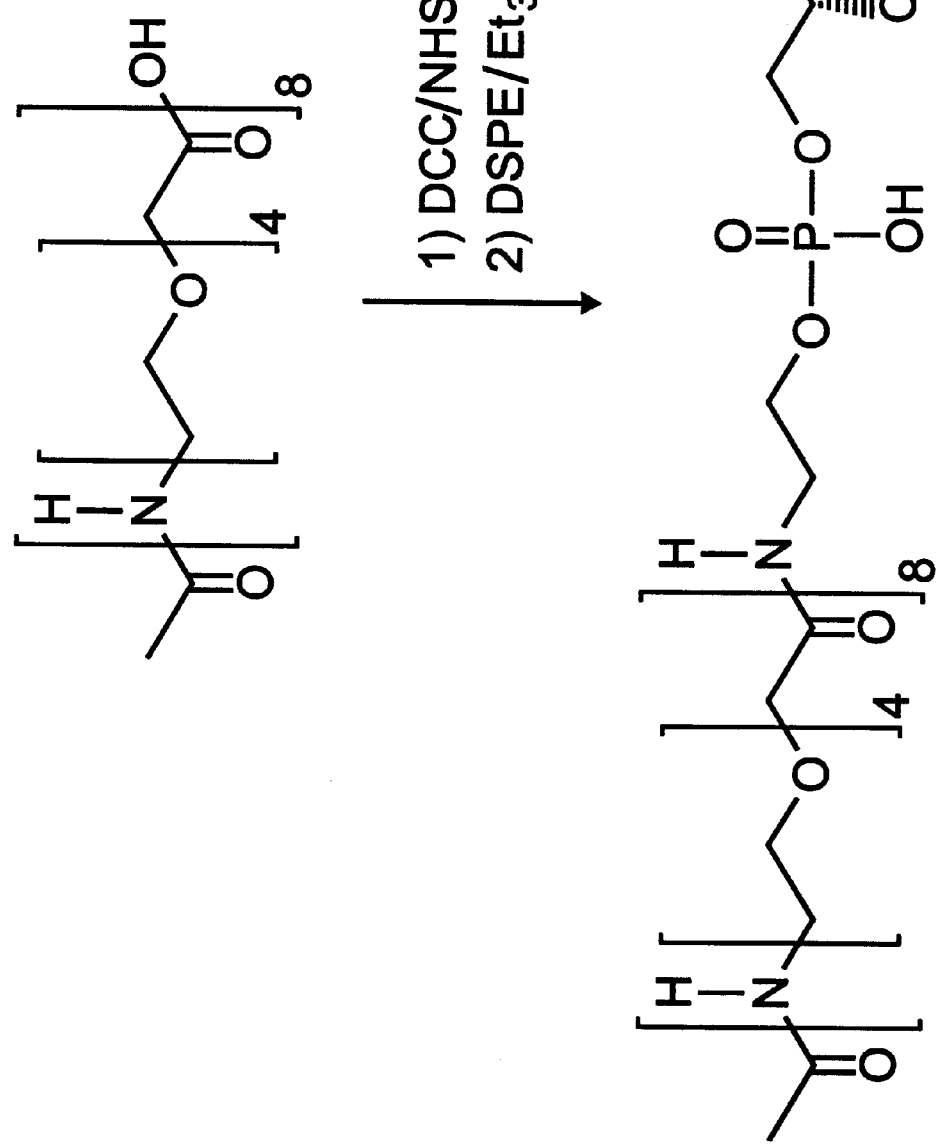
FIG. 3 illustrates the synthesis of an oligomer lipid conjugate exemplified by N-(ω-N'-acetoxy-octa-(14'-amino-3', 6', 9', 12'-tetraoxatetradecanoyl))-1,2-distearoyl-sn-glycero-3-phosphoethanolamine ("ATTA8-DSPE")

In one preferred embodiment which is illustrated in FIG. 3, N-(ω-N-acetoxy-octa-(14'-amino-3',6',9',12'-tetraoxatetradecanoyl))- 1,2-distearoyl-sn-glycero-3-phosphoethanolamine (herein referred to as "ATTA8-DPSE") was generated from the octamer using (NHS) and (DCC) to activate the molecule, i.e., the octamer. This activated octamer was then reacted with 1,2-distearoyl-sn-glycero-3-phosphoethanolamine to form a new amide bond. The details of this procedure are outlined in Example 1.

Methods known to those of skill in the art can be used for covalent attachment of ligands A and B to the PAO. Suitable linkages include, but are not limited to, amide, amine, carboxyl, carbonate, carbamate, ester and hydrazone bonds. Additional linkages, such as phosphoro and disulfide bonds, can be employed if a cross-linker is used. It will be apparent to those skilled in the art that the ligand(s) to be attached must have a complementary functional group with the PAO. The reaction of these two groups, one on the ligand and the other on the PAO, will provide the desired linkage. For example, when $R^3$ is hydroxyl and is activated, for instance with NHS and DCC, to form an active ester, and is then reacted with B which contains an amino group. Where the ligand is a glycosylated protein, such as an antibody, a primary alcohol of the glycosylated protein can be oxidized to form an aldehyde. The aldehyde can then be reacted with the PAO having a hydrazide function ($R^3$=NH$_2$NH—) to form the hydrazone (—C=N—NH—).

It may also be desirable to conjugate the A side of the PAO with a ligand. A covalent attachment of a ligand (A) of the compound of Formula II can be generated by complementary reactivity of functional groups, one on the ligand and wherein: v, m, r, x, s, z, t, $R^1$, $R^2$, $R^6$, $R^7$, A and B are as defined above. A and B can be covalently attached as described above.

C. Liposome Membrane Components

After the PAO-lipid conjugates are prepared, they can be utilized in a variety of ways including, for example, in liposomes, in micelles, in virosomes, in lipid- nucleic acid particles, nucleic acid aggregates and other lipidized drug delivery systems, i.e., compositions, which incorporate or entrap one or more bioactive agents. Such delivery systems are described in greater detail in, for example, the following copending U.S. patent applications Ser. Nos. 08/454,641, 08/485,458, 08/660,025, 08/484,282, 60/055,094, 08/856, 374, 60/053,813 and 60/063,473, entitled "Methods for Encapsulating Nucleic Acids in Lipid Bilayers," filed on Oct. 10, 1997, as well as U.S. Pat. No. 5,703,055 the teachings all of which are incorporated herein by reference.

The lipid components and PAO-lipid conjugates used in forming the various drug delivery systems will depend, in part, on the type of delivery system employed. For instance, if a liposome is employed, the lipids used in the PAO-lipid conjugate will generally be selected from a variety of vesicle-forming or vesicle adopting lipids, typically including phospholipids and sterols, such as phosphatidylethanolamine (PE), phosphatidylserine (PS), phosphatidylinositol (PI), phosphatidylglycerol (PG), phosphatidic acid (PA), which has been suitably functionalized, and the like. In contrast, if a micelle is employed, the lipids used in the PAO-lipid conjugate will generally be selected from sterylamines, alkylamines, $C_8$–$C_{22}$ alkanoic acids, lysophospholipids, detergents and the like. It will be readily apparent to those of skill in the art that the acyl chains can be varied in length and can be saturated or possess varying degrees of unsaturation. The more saturated the acyl chains the more rigid the membrane. Higher degrees of unsaturation impart more fluidity into the vesicle's membrane. Similarly, the other lipid components (e.g., lipids, cationic lipids, neutral lipids, non-cationic lipids, etc.) making up the drug delivery systems of the present invention will varying depending on the drug delivery system employed. Suitable lipids for the various drug delivery systems will be readily apparent to those of skill in the art.

When the drug delivery systems are used to deliver therapeutic genes or oligonucleotides intended to induce or to block production of some protein within the cell, cationic lipids may be included in the drug delivery system, e.g., liposome, micelle, lipid-nucleic acid particle, etc. Nucleic acid is negatively charged and may be combined with a positively charged entity to form a lipid complex suitable for formulation and cellular delivery.

Examples of suitable cationic lipids include, but are not limited to, the following: DC-Chol, (see, Gao, et al., *Biochem. Biophys. Res. Comm.*, 179:280–285 (1991); DDAB; DMRIE; DODAC, (see, commonly owned U.S. patent application Ser. No. 08/316,399, filed Sep. 30, 1994, which is incorporated herein by reference); DOGS; DOSPA; DOTAP; and DOTMA. In a presently preferred embodiment, N,N-dioleoyl-N,N-dimethylammonium chloride is used in combination with a phosphatidylethanolamine.

In addition, other cationic lipids useful in producing lipid-based carriers for gene and oligonucleotide delivery are LIPOFECTIN (U.S. Pat. Nos. 4,897,355; 4,946,787; and 5,208,036 by Eppstein, et al.) and LIPOFECTACE (U.S. Pat. No. 5,279,883 by Rose). Both agents, as well as other transfecting cationic lipids, are available from Life Technologies, Inc. in Gaithersburg, Md.

It will be apparent to those skilled in the art that it is possible and often advantageous to use a mixture of at least two polyamide oligomers molecular weights i.e., sizes. For example, in Formula I, it is possible to vary the amount of ethylene oxide (the value of m may vary from 2–6) to generate a distribution of short and long chain polyamide oligomers. The amount of each polyamide oligomer can be added to arrive at an exact ratio of each polyamide oligomer in the mixture of oligomers. For example, by controlling the distribution, it is possible to vary the properties of the drug delivery systems of the present invention (e.g., the fusogenic properties of liposomes).

In one embodiment of the present invention, a fusogenic liposome or virosome is provided. It will be readily apparent to those of skill in the art that the PAO-lipid conjugates of the present invention can advantageously be incorporated into various types of fusogenic liposomes and virosomes. Such fusogenic liposomes and virosomes can be designed to become fusogenic at the disease or target site. Those of skill in the art will readily appreciate that a number of variables can be used to control when the liposome or virosome becomes fusogenic. Such variables include, for example, the composition of the liposome or virosome, pH, temperature, enzymes, cofactors, ions, etc.

In one embodiment, the fusogenic liposome comprises: a lipid capable of adopting a non-lamellar phase, yet capable of assuming a bilayer structure in the presence of a PAO-lipid conjugate; and a PAO-lipid conjugate reversibly associated with the lipid to stabilize the lipid in a bilayer structure. In a presently preferred embodiment, the fusogenic liposome is made up of DOPE and a PAO-PE conjugate. Such fusogenic liposomes are advantageous because the rate at which they become fusogenic can be not only predetermined, but varied as required over a time scale of a few minutes to several tens of hours. It has been found, for example, that by controlling the composition and concentration of the PAO-lipid conjugate, one can control the rate at which the PAO-lipid exchanges out of the liposome in vivo and, in turn, the rate at which the liposome becomes fusogenic (see, U.S. application Ser. No. 08/485,608). For instance, it has been found that by controlling the length of the lipid acyl chain(s), one can control the rate at which the PAO-lipid exchanges out of the liposome in vivo and, in turn, the rate at which the liposome becomes fusogenic. In particular, it has been discovered that shorter acyl chains (e.g., C-8) exchange out of the liposome more rapidly than longer acyl chains (e.g., C-20). Alternatively, by controlling the composition and concentration of the PAO-lipid conjugate, one can control the rate at which the PAO-lipid is degraded, i.e., broken down, by endogenous systems, e.g., endogenoous enzymes in the serum, and, in turn, the rate at which the liposome becomes fusogenic.

The polymorphic behavior of lipids in organized assemblies can be explained qualitatively in terms of the dynamic molecular shape concept (see, Cullis, et al., in "Membrane Fusion" (Wilschut, J. and D. Hoekstra (eds.), Marcel Dekker, Inc., New York, (1991)). When the effective cross-sectional areas of the polar head group and the hydrophobic region buried within the membrane are similar then the lipids have a cylindrical shape and tend to adopt a bilayer conformation. Cone-shaped lipids which have polar head groups that are small relative to the hydrophobic component, such as unsaturated phosphatidylethanolamines, prefer non-bilayer phases such as inverted micelles or inverse hexagonal phase ($H_{II}$). Lipids with head groups that are large relative to their hydrophobic domain, such as lysophospholipids, have an inverted cone shape and tend to form micelles in aqueous solution. The phase preference of a mixed lipid system depends, therefore, on the contributions of all the components to the net dynamic molecular shape. As such, a combination of cone-shaped and inverted cone-shaped lipids can adopt a bilayer conformation under conditions where either lipid in isolation cannot (see, Madden and Cullis, *Biochim. Biophys. Acta*, 684:149–153 (1982)).

A more formalized model is based on the intrinsic curvature hypothesis (see, e.g., Kirk, et al., *Biochemistry*, 23:1093–1102 (1984)). This model explains phospholipid polymorphism in terms of two opposing forces. The natural tendency of a lipid monolayer to curl and adopt its intrinsic or equilibrium radius of curvature ($R_o$) which results in an elastically relaxed monolayer is opposed by the hydrocarbon packing constraints that result. Factors that decrease the intrinsic radius of curvature, such as increased volume occupied by the hydrocarbon chains when double bonds are introduced, tend to promote $H_{II}$ phase formation. Conversely, an increase in the size of the headgroup increases $R_o$ and promotes bilayer formation or stabilization. Introduction of apolar lipids that can fill the voids between inverted lipid cylinders also promotes $H_{II}$ phase formation (see, Gruner, et al., *Proc. Natl. Acad. Sci. USA*, 82:3665–3669 (1989); Sjoland, et al., *Biochemistry*, 28:1323–1329 (1989)).

As such, in one embodiment, the lipids which can be used to form the fusogenic liposomes of the present invention are those which adopt a non-lamellar phase under physiological conditions or under specific physiological conditions, e.g., in the presence of calcium ions, but which are capable of assuming a bilayer structure in the presence of a PAO-lipid derivative. Such lipids include, but are not limited to, phosphatidylenthanolamines, ceramides, glycolipids, or mixtures thereof. Other lipids known to those of skill in the art to adopt a non-lamellar phase under physiological conditions can also be used. Moreover, it will be readily apparent to those of skill in the art that other lipids can be induced to adopt a non-lamellar phase by various non-physiological changes including, for example, changes in pH or ion concentration (e.g., in the presence of calcium ions) and, thus, they can also be used to form the fusogenic liposomes of the present invention. In a presently preferred embodiment, the fusogenic liposome is prepared from a phosphatidylethanolamine. The phosphatidylethanolamine can be saturated or unsaturated. In a presently preferred embodiment, the phosphatidylyethanolamine is unsaturated. In an equally preferred embodiment, the fusogenic liposome is prepared from a mixture of a phosphatidylethanolamine (saturated or unsaturated) and a phosphatidylserine. In another equally preferred embodiment, the fusogenic liposome is prepared from a mixture of a phosphatidylethanolamine (saturated or unsaturated) and a cationic lipid.

In accordance with the present invention, lipids adopting a non-lamellar phase under physiological conditions can be stabilized in a bilayer structure by PAO-lipids which are either bilayer forming themselves, or which are of a complementary dynamic shape. The non-bilayer forming lipid is stabilized in the bilayer structure only when it is associated with, i.e., in the presence of, the PAO-lipid. In selecting an appropriate PAO-lipid conjugate, it is preferable that the PAO-lipid be capable of transferring out of the liposome, or of being chemically modified by endogenous systems such that, with time, it loses its ability to stabilize the lipid in a bilayer structure. Only when liposomal stability is lost or decreased can fusion of the liposome with the plasma membrane of the target cell occur. The PAO-lipid, therefore, is "reversibly associated" with the lipid and only when it is associated with the lipid is the lipid constrained to adopt the bilayer structure under conditions where it would otherwise adopt a non-lamellar phase. As such, the PAO-lipids of the present invention are capable of stabilizing the lipid in a bilayer structure, yet they are capable of exchanging out of the liposome, or of being chemically modified by endogenous systems so that, with time, they lose their ability to stabilize the lipid in a bilayer structure, thereby allowing the liposome to become fusogenic.

Typically, the PAO-lipid conjugate is present at a concentration ranging from about 0.05 mole percent to about 50 mole percent. In a presently preferred embodiment, the PAO-lipid conjugate is present at a concentration ranging from 0.05 mole percent to about 25 mole percent. In an even more preferred embodiment, the PAO-lipid conjugate is present at a concentration ranging from 0.05 mole percent to about 15 mole percent. One of ordinary skill in the art will appreciate that the concentration of the PAO-lipid conjugate can be varied depending on the PAO-lipid conjugate employed and the rate at which the liposome is to become fusogenic.

By controlling the composition and concentration of the PAO-lipid conjugate, one can control the rate at which the PAO-lipid conjugate exchanges out of the liposome and, in turn, the rate at which the liposome becomes fusogenic. For instance, when a PAO-phosphatidylethanolamine conjugate or a PAO-ceramide conjugate is used as the bilayer stabilizing component, the rate at which the liposome becomes fusogenic can be varied, for example, by varying the concentration of the PAO-lipid conjugate, by varying the molecular weight or composition of the PAO, or by varying the chain length and degree of saturation of the acyl chain groups on the phosphatidylethanolamine or the ceramide. In addition, other variables including, for example, pH, temperature, ionic strength, etc. can be used to vary and/or control the rate at which the liposome becomes fusogenic. Other methods which can be used to control the rate at which the liposome becomes fusogenic will become apparent to those of skill in the art upon reading this disclosure.

In one preferred embodiment of the present invention, the liposomes contain cholesterol. It has been determined that when cholesterol-free liposomes are used in vivo, they have a tendency to absorb cholesterol from the plasma lipoproteins and cell membranes. Cholesterol, if included, is generally present at a concentration ranging from 0.2 mole percent to about 50 mole percent and, more preferably, at a concentration ranging from about 35 mole percent to about 45 mole percent.

D. Liposome Preparation

A variety of methods are available for preparing liposomes as described in, e.g., Szoka, et al., *Ann. Rev. Biophys. Bioeng.,* 9:467 (1980), U.S. Pat. Nos. 4,186,183, 4,217,344, 4,235,871, 4,261,975, 4,485,054, 4,501,728, 4,774,085, 4,837,028, 4,946,787, PCT Publication No. WO 91/17424, Deamer and Bangham, *Biochim. Biophys. Acta,* 443:629–634 (1976); Fraley, et al., *Proc. Natl. Acad. Sci. USA,* 76:3348–3352 (1979); Hope, et al., *Biochim. Biophys. Acta,* 812:55–65 (1985); Mayer, et al., *Biochim. Biophys. Acta,* 858:161–168 (1986); Williams, et al., *Proc. Natl. Acad. Sci.,* 85:242–246 (1988), the text *Liposomes,* Marc J. Ostro, ed., Marcel Dekker, Inc., New York, 1983, Chapter 1, and Hope, et al., *Chem. Phys. Lip.,* 40:89 (1986), all of which are incorporated herein by reference. Suitable methods include, but are not limited to, sonication, extrusion, high pressure/homogenization, microfluidization, detergent dialysis, calcium-induced fusion of small liposome vesicles, and ether-infusion methods, all of which are well known in the art. One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions or by adding solubilizing detergents, such as deoxycholate.

Unilamellar vesicles are generally prepared by sonication or extrusion. Sonication is generally performed with a tip sonifier, such as a Branson tip sonifier, in an ice bath. Typically, the suspension is subjected to severed sonication cycles. Extrusion may be carried out by biomembrane extruders, such as the Lipex Biomembrane Extruder. Defined pore size in the extrusion filters may generate unilamellar liposomal vesicles of specific sizes. The liposomes may also be formed by extrusion through an asymmetric ceramic filter, such as a Ceraflow Microfilter, commercially available from the Norton Company, Worcester Ma.

Following liposome preparation, the liposomes which have not been sized during formation may be sized to achieve a desired size range and relatively narrow distribution of liposome sizes. A size range of about 0.2–0.4 microns allows the liposome suspension to be sterilized by filtration through a conventional filter. The filter sterilization method can be carried out on a high through-put basis if the liposomes have been sized down to about 0.2–0.4 microns.

Several techniques are available for sizing liposomes to a desired size. One sizing method is described in U.S. Pat. No. 4,737,323, incorporated herein by reference. Sonicating a liposome suspension either by bath or probe sonication produces a progressive size reduction down to small unilamellar vesicles less than about 0.05 microns in size. Homogenization is another method which relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. The size of the liposomal vesicles may be determined by quasi-electric light scattering (QELS) as described in Bloomfield, *Ann. Rev. Biophys. Bioeng.*, 10:421–450 (1981), incorporated herein by reference. Average liposome diameter may be reduced by sonication of formed liposomes. Intermittent sonication cycles may be alternated with QELS assessment to guide efficient liposome synthesis.

Extrusion of liposome through a small-pore polycarbonate membrane or an asymmetric ceramic membrane is also an effective method for reducing liposome sizes to a relatively well-defined size distribution. Typically, the suspension is cycled through the membrane one or more times until the desired liposome size distribution is achieved. The liposomes may be extruded through successively smaller-pore membranes, to achieve gradual reduction in liposome size. For use in the present invention, liposomes having a size ranging from about 0.05 microns to about 0.40 microns are preferred.

E. Use of Liposomes as Drug Delivery Vehicles

The drug delivery compositions of the present invention (e.g., liposomes, micelles, lipid-nucleic acid particles, virosomes, etc.) are useful for the systemic or local delivery of therapeutic agents or bioactive agents and are also useful in diagnostic assays. Such delivery systems are described in greater detail in, for example, the following copending U.S. patent applications Ser. Nos. 08/454,641, 08/485,458, 08/660,025, 08/484,282, 60/055,094, 08/856,374, 60/053,813 and 60/063,473, entitled "Methods for Encapsulating Nucleic Acids in Lipid Bilayers," filed on Oct. 10, 1997 the teachings of all of which are incorporated herein by reference.

The following discussion refers generally to liposomes; however, it will be readily apparent to those of skill in the art that this same discussion is fully applicable to the other drug delivery systems of the present invention (e.g., micelles, virosomes, lipid-nucleic acid particles, etc.).

For the delivery of therapeutic or bioactive agents, the compositions can be loaded with a therapeutic agent and administered to the subject requiring treatment. The therapeutic agents which are administered using the present invention can be any of a variety of drugs which are selected to be an appropriate treatment for the disease to be treated. Often the drug will be an antineoplastic agent, such as vincristine, doxorubicin, mitoxantrone, camptothecin, cisplatin, bleomycin, cyclophosphamide, methotrexate, streptozotocin, and the like. Especially preferred antitumor agents include, for example, actinomycin D, vincristine, vinblastine, cystine arabinoside, anthracyclines, alkylative agents, platinum compounds, antimetabolites, and nucleoside analogs, such as methotrexate and purine and pyrimidine analogs. It may also be desirable to deliver anti-infective agents to specific tissues by the present methods. The compositions of the present invention can also be used for the selective delivery of other drugs including, but not limited to, local anesthetics, e.g., dibucaine and chlorpromazine; beta-adrenergic blockers, e.g., propranolol, timolol and labetolol; antihypertensive agents, e.g., clonidine and hydralazine; anti-depressants, e.g., imipramine, amitriptyline and doxepim; anti-conversants, e.g., phenytoin; antihistamines, e.g., diphenhydramine, chlorphenirimine and promethazine; antibiotic/antibacterial agents, e.g., gentamycin, ciprofloxacin, and cefoxitin; antifungal agents, e.g., miconazole, terconazole, econazole, isoconazole, butaconazole, clotrimazole, itraconazole, nystatin, naftifine and amphotericin B; antiparasitic agents, hormones, hormone antagonists, immunomodulators, neurotransmitter antagonists, antiglaucoma agents, vitamins, narcotics, and imaging agents.

As mentioned above, cationic lipids can be used in the delivery of therapeutic genes or oligonucleotides intended to induce or to block production of some protein within the cell. Nucleic acid is negatively charged and may be combined with a positively charged entity to form a lipid complex suitable for formulation and cellular delivery.

Particularly useful antisense oligonucleotides are directed to targets such as c-myc, bcr-abl, c-myb, ICAM-1, C-erb B-2 and BCL-2.

The PAO-lipid conjugates of the present invention are also useful in the delivery of peptides, nucleic acids, plasmid DNA, minichromosomes and ribozymes.

Another clinical application of PAO-lipid conjugates of this invention is as an adjuvant for immunization of both animals and humans. Protein antigens, such as diphtheria toxoid, cholera toxin, parasitic antigens, viral antigens, immunoglobulins, enzymes and histocompatibility antigens, can be incorporated into or attached onto the liposomes containing the PAO-lipid conjugates of the present invention for immunization purposes.

Liposomes containing the PAO-lipid conjugates of the present invention are also particularly useful as carriers for vaccines that will be targeted to the appropriate lymphoid organs to stimulate an immune response.

Liposomes containing the PAO-lipid conjugates of the present invention can also be used as a vector to deliver immunosuppressive or immunostimulatory agents selectively to macrophages. In particular, glucocorticoids useful to suppress macrophage activity and lymphokines that activate macrophages can be delivered using the liposomes of the present invention.

Liposomes containing the PAO-lipid conjugates of the present invention and containing targeting molecules can be used to stimulate or suppress a cell. For example, liposomes incorporating a particular antigen can be employed to stimulate the B cell population displaying surface antibody that specifically binds that antigen. Liposomes incorporating growth factors or lymphokines on the liposome surface can be directed to stimulate cells expressing the appropriate receptors for these factors. Using this approach, bone marrow cells can be stimulated to proliferate as part of the treatment of cancer patients.

Liposome-encapsulated antibodies can be used to treat drug overdoses. The tendency of liposomes having encapsulated antibodies to be delivered to the liver has a therapeutic advantage in clearing substances, such as toxic agents, from the blood circulation. It has been demonstrated that whereas unencapsulated antibodies to digoxin caused intravascular retention of the drug, encapsulated antibodies caused increased splenic and hepatic uptake and an increased excretion rate of digoxin.

Liposomes containing the PAO-lipid conjugates of this invention also find utility as carriers for introducing lipid or protein antigens into the plasma membrane of cells that lack the antigens. For example, histocompatibility antigens or viral antigens can be introduced into the surface of viral infected or tumor cells to promote recognition and killing of these cells by the immune system.

In addition, liposomes containing the PAO-lipid conjugates of the present invention can be used to deliver any product (e.g., therapeutic agents, diagnostic agents, labels or other compounds) including those currently formulated in PEG-derivatized liposomes.

In certain embodiments, it is desirable to target the liposomes of this invention using targeting moieties that are specific to a cell type or tissue. Targeting of liposomes using a variety of targeting moieties, such as ligands, cell surface receptors, glycoproteins, vitamins (e.g., riboflavin) and monoclonal antibodies, has been previously described (see, e.g., U.S. Pat. Nos. 4,957,773 and 4,603,044, the teachings of which are incorporated herein by reference). The targeting moieties can comprise the entire protein or fragments thereof.

Targeting mechanisms generally require that the targeting agents be positioned on the surface of the liposome in such a manner that the target moiety is available for interaction with the target, for example, a cell surface receptor. The liposome is designed to incorporate a connector portion into the membrane at the time of liposome formation. The connector portion must have a lipophilic portion that is firmly embedded and anchored into the membrane. It must also have a hydrophilic portion that is chemically available on the aqueous surface of the liposome. The hydrophilic portion is selected so as to be chemically suitable with the targeting agent, such that the portion and agent form a stable chemical bond. Therefore, the connector portion usually extends out from the liposome's surface and is configured to correctly position the targeting agent. In some cases, it is possible to attach the target agent directly to the connector portion, but in many instances, it is more suitable to use a third molecule to act as a "molecular bridge." The bridge links the connector portion and the target agent off of the surface of the liposome, thereby making the target agent freely available for interaction with the cellular target.

Standard methods for coupling the target agents can be used. For example, phosphatidylethanolamine, which can be activated for attachment of target agents, or derivatized lipophilic compounds, such as lipid-derivatized bleomycin, can be used. Antibody-targeted liposomes can be constructed using, for instance, liposomes that incorporate protein A (see, Renneisen, et al., *J. Bio. Chem.*, 265:16337–16342 (1990) and Leonetti, et al., *Proc. Natl. Acad. Sci.* (USA), 87:2448–2451 (1990). Other examples of antibody conjugation are disclosed in U.S. patent application Ser. No. 08/316,394, filed Sep. 30, 1994, the teachings of which are incorporated herein by reference. Examples of targeting moieties can also include other proteins, specific to cellular components, including antigens associated with neoplasms or tumors. Proteins used as targeting moieties can be attached to the liposomes via covalent bonds. See, Heath, *Covalent Attachment of Proteins to Liposomes,* 149 *Methods in Enzymology* 111–119 (Academic Press, Inc. 1987). Other targeting methods include the biotin-avidin system.

In some cases, the diagnostic targeting of the liposome can subsequently be used to treat the targeted cell or tissue. For example, when a toxin is coupled to a targeted liposome, the toxin can then be effective in destroying the targeted cell, such as a neoplasmic cell.

In addition, as described above, one of the advantages of the PAO compounds of the present invention is that they are intrinsically heterobifunctional where each end of the molecule is different. As such, a lipid or other ligand can be conjugated to one end of the PAO, while an antibody or other targeting moiety can be conjugated to the other end of the PAO. Accordingly, the PAO compounds of the present invention can serve as the "connector portion" or the "molecular bridge" as described above.

Moreover, it will be readily apparent to those of skill in the art that the PAO compounds of the present invention can be conjugated to biomaterials, biopolymers and biomedical devices including, but not limited to, catheters and stents. Other uses for the PAO compounds of the present invention will be readily apparent to those of skill in the art upon a reading of the disclosure.

F. Use of the Liposomes as Diagnostic Agents

The drug delivery compositions, e.g., liposomes, prepared using the PAO-lipids of this invention can be labeled with markers that will facilitate diagnostic imaging of various disease states including tumors, inflamed joints, lesions, etc. Typically, these labels will be radioactive markers, although fluorescent labels can also be used. The use of gamma-emitting radioisotopes is particularly advantageous as they can easily be counted in a scintillation well counter, do not require tissue homogenization prior to counting and can be imaged with gamma cameras.

Gamma- or positron-emitting radioisotopes are typically used, such as $^{99}$Tc, $^{24}$Na, $^{51}$Cr, $^{59}$Fe, $^{67}$Ga, $^{86}$Rb, $^{111}$In, $^{125}$J, and $^{195}$Pt as gamma-emitting; as $^{68}$Ga, $^{82}$Rb, $^{22}$Na, $^{75}$Br, $^{122}$I and $^{18}$F as positron-emitting.

The liposomes can also be labelled with a paramagnetic isotope for purposes of in vivo diagnosis, as through the use of magnetic resonance imaging (MRI) or electron spin resonance (ESR). See, for example, U.S. Pat. No. 4,728,575, the teachings of which are incorporated herein by reference.

G. Loading the Liposomes

Methods of loading conventional drugs into liposomes include, for example, an encapsulation technique, loading into the bilayer and a transmembrane potential loading method.

In one encapsulation technique, the drug and liposome components are dissolved in an organic solvent in which all species are miscible and concentrated to a dry film. A buffer is then added to the dried film and liposomes are formed having the drug incorporated into the vesicle walls. Alternatively, the drug can be placed into a buffer and added to a dried film of only lipid components. In this manner, the drug will become encapsulated in the aqueous interior of the liposome. The buffer which is used in the formation of the liposomes can be any biologically compatible buffer solution of, for example, isotonic saline, phosphate buffered saline, or other low ionic strength buffers. Generally, the drug will be present in an amount of from about 0.01 ng/mL to about 50 mg/mL. The resulting liposomes with the drug incorporated in the aqueous interior or in the membrane are then optionally sized as described above.

Transmembrane potential loading has been described in detail in U.S. Pat. Nos. 4,885,172, 5,059,421, and 5,171,578, the contents of which are incorporated herein by reference. Briefly, the transmembrane potential loading method can be used with essentially any conventional drug which can exist in a charged state when dissolved in an appropriate aqueous medium. Preferably, the drug will be relatively lipophilic so that it will partition into the liposome membranes. A transmembrane potential is created across the bilayers of the liposomes or protein-liposome complexes and the drug is loaded into the liposome by means of the transmembrane potential. The transmembrane potential is generated by creating a concentration gradient for one or more charged species (e.g., Na⁺, K⁺and/or H⁺) across the membranes. This concentration gradient is generated by producing liposomes having different internal and external media and has an associated proton gradient. Drug accumulation can than occur in a manner predicted by the Henderson-Hasselbach equation.

The liposome compositions of the present invention can by administered to a subject according to standard techniques. Preferably, pharmaceutical compositions of the liposome compositions are administered parenterally, i.e., intraperitoneally, intravenously, subcutaneously or intramuscularly. More preferably, the pharmaceutical compositions are administered intravenously by a bolus injection. Suitable formulations for use in the present invention are found in *Remington's Pharmaceutical Sciences*, Mack Publishing Company, Philadelphia, Pa., 17th ed. (1985). The pharmaceutical compositions can be used, for example, to diagnose a variety of conditions, or treat a diseased state. The diseases include, but are not limited to, inflammation associated with rheumatoid arthritis, post-ischemic leukocyte-mediated tissue damage (reperfusion injury), acute leukocyte-mediated lung injury (e.g., adult respiratory distress syndrome), septic shock, and acute and chronic inflammation, including atopic dermatitis and psoriasis. In addition, various neoplasms and tumor metastases can be treated.

Preferably, the pharmaceutical compositions are administered intravenously. Thus, this invention provides compositions for intravenous administration which comprise a solution of the liposomes suspended in an acceptable carrier, preferably an aqueous carrier. A variety of aqueous carriers can be used, e.g., water, buffered water, 0.9% isotonic saline, and the like. These compositions can be sterilized by conventional, well known sterilization techniques, or may be sterile filtered. The resulting aqueous solutions may be packaged for use as is or lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, etc.

The concentration of liposome compositions in the pharmaceutical formulations can vary widely, i.e., from less than about 0.05%, usually at or at least about 2–5% to as much as 10 to 30% by weight and will be selected primarily by fluid volumes, viscosities, etc., in accordance with the particular mode of administration selected. For diagnosis, the amount of composition administered will depend upon the particular label used (i.e., radiolabel, fluorescence label, and the like), the disease state being diagnosed and the judgement of the clinician, but will generally be between about 1 and about 5 mg per kilogram of body weight.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

Example I

This example illustrates the synthesis of N-(ω-azido-octa-(14'-amino-3',6',9',12'-tetraoxatetradecanoyl))-1,2-distearoyl-sn-glycero-3-phosphoethanolamine ("ATTA-DPSE").

Synthesis of 1-O-tetrahydropyratiyl-11-hydroxy-3,6,9-trioxaundecanol 1

Concentrated hydrochloric acid (5 mL) was slowly added to a solution of dihydropyran (215 g) in tetraethylene glycol (600 g). The exothermic reaction was cooled in an ice bath and then stirred overnight at room temperature. The solution was diluted with water (1 L) and neutralized with excess sodium bicarbonate solution until slightly basic. The solution was washed twice with diethyl ether (200 mL). The combined ethereal extracts were washed twice with water (200 mL). The aqueous fractions were washed with diethyl ether (100 mL) and then combined with the original aqueous extract. This extract was then washed four times with methylene chloride. The methylene chloride fractions were combined and washed with water (200 mL), which in turn was washed with methylene chloride. The combined methylene chloride fractions were dried down on a rotovap. Residual water was removed by azeotropic distillation with toluene on a rotovap (four times), yielding 1 as a colorless crude oil (390 g).

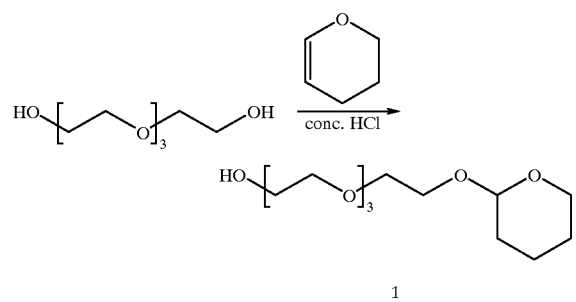

Synthesis of Ethyl 14-hydroxy-3,6,9,12-tetraoxatetradecanoate 2

A solution of crude 1 (390 g) in toluene (1 L) was treated with sodium (64 g) in a closed flask vented through a mineral oil bubbler. The mixture was stirred at room temperature for five days and then filtered through glass wool to remove unreacted sodium. Ethyl bromoacetate (100 mL) was added and the mixture refluxed for three hours. The solution was cooled and washed with water (2×500 mL). The aqueous phase was washed with methylene chloride (2×100 mL). The organic fractions were combined and the solvent removed on a rotovap. The residue was then dissolved in ethanol (1 L) and treated with pyridinyl p-toluenesulfonic acid (30 g) at 60° C. for one hour. The solution was diluted with water and washed with ether (2×400 mL). The ether fractions were washed with water (100 mL). The combined aqueous fractions were washed with methylene chloride (4×), yielding 180 g of crude 2 after removal of the solvent.

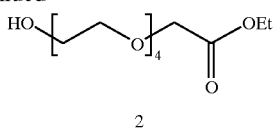

2

Synthesis of 14-azido-3,6,9,12-tetraoxatetradecanoic acid 3

Triethylamine (81 mL) was slowly added to a stirred solution of crude 2 (110 g) and methane sulfonylchloride (36 mL) in benzene (600 mL). The solution was stirred at room temperature for one hour, diluted with water and acidified with dilute hydrochloric acid. The mixture was extracted with methylene chloride (3×). The solvent was removed on a rotovap. Residual methylene chloride was removed by addition of toluene followed by removal of solvent on a rotovap (3×). The residue was dissolved in ethanol (750 mL). Sodium azide (24 g) was added and the solution refluxed for four hours. Periodic additions of water were made as a gel like precipitate formed to keep most of the material in solution. The mixture was then stirred at room temperature overnight. The mixture was filtered, diluted with water and extracted with methylene chloride (6×). The combined methylene chloride fractions were washed with water, which in turn was washed with methylene chloride (4×). The solvent was removed from the combined methylene chloride fractions using a rotovap. The residue was suspended in a solution of sodium hydroxide (32 g) in water (100 mL) and stirred at 45° C. for half an hour. The mixture was diluted with water (200 mL) and extracted with methylene chloride (3×100 mL). The methylene chloride fractions were washed with water (2×50 mL) and the aqueous fractions combined with the previous aqueous extracts. The combined aqueous fractions were acidified with concentrated hydrochloric acid and extracted with methylene chloride (3×100 mL). The solvent was removed from the organic fractions using a rotovap and the residue dried by addition of ethanol followed by removal of the solvent, yielding 3 as a yellow oil (77 g).

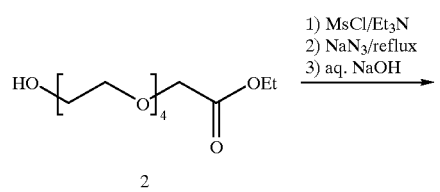

Synthesis of Ethyl 14-amino-3,6,9,12-tetraoxatetradecanoate 4

A solution of anhydrous hydrogen chloride in ethanol was prepared by slow addition of acetyl chloride (100 mL) to anhydrous ethanol (500 mL), followed by stirring at room temperature for one hour. 3 (44 g) was added and the solution stirred for one hour. Water (1 L) was added and the solution extracted with methylene chloride (3×). The solvent was removed on a rotovap and the residue dissolved in ethanol. Activated charcoal was added and the mixture stirred for approximately half an hour after which it was filtered through celite. The solvent was then removed on a rotovap. The residue was dissolved in ethanol/water (50:50) (200 mL). Formic acid was added (16 g) followed by 10% palladium/carbon (2.7 g). The solution was warmed to 60° C. and stirred until evolution of gas had ceased. The mixture was filtered through celite. The filtrate was neutralized with aqueous sodium bicarbonate until samples diluted with water were neutral (pH~7) by analysis with pH paper. The solvent was then removed on a rotovap. Residual water and salt were removed by filtration and azeotropic distillation with ethanol (2×), yielding crude 4 as a yellow oil (33 g).

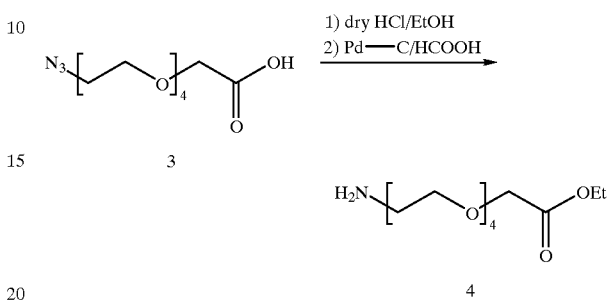

Synthesis of Ethyl-ω-azido-bis-(14-amino-3,6,9,12-tetraoxatetradecanoate) 5

A solution of 3 (33 g) in methylene chloride (100 mL) was treated with N-hydroxysuccimide (NHS, 20 g) and N,N-dicyclohexylcarbodiimide (DCC, 27 g dissolved in 300 mL methylene chloride). The solution was stirred for one hour and filtered. A solution of 4 (33 g) in ethanol (100 mL) was added to the filtrate, followed by triethylamine (20 mL). The reaction mixture was stirred at room temperature for 1 h, filtered and diluted with water. Extraction of the aqueous phase with methylene chloride yielded ~10 g crude 3. The aqueous phase was acidified with dilute hydrochloric acid and extracted with methylene chloride (3×). The solvent was removed on a rotovap and the residue dissolved in water. All residual solvent was removed using the rotovap and the aqueous suspension filtered. The aqueous solution was then extracted with methylene chloride (3×), yielding ~40 g of crude 5 after removal of the solvent. Crude 5 was passed down a silica gel column (300 g $SiO_2$, 4–16% MeOH/$CH_2Cl_2$), yielding 16 g of 5.

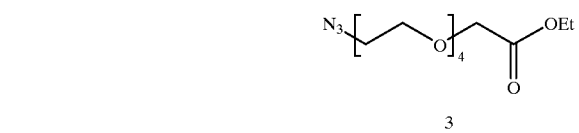

Synthesis of Ethyl-ω-azido-tetra-(14-amino-3,6,9,12-tetraoxatetradecanoate) 8

A suspension of 5 (15 g) in a solution of sodium carbonate (15 g) in water (150 mL) was stirred at 45° C. until all of the oil had dissolved. The solution was stirred at 45° C. for a further half an hour and then extracted with methylene chloride (2×). The solution was acidified (pH=2) with dilute hydrochloric acid and extracted with methylene chloride (3×). Removal of solvent yielded the crude acid 6 (9 g).

5 (15 g) was added to an anhydrous solution of hydrogen chloride in ethanol (prepared from 40 mL acetyl chloride and 200 mL ethanol) and stirred at room temperature for two hours. The solution was diluted with water and extracted with methylene chloride (3×). The solvent was removed on a rotovap. The residue was dissolved in ethanol (100 mL) and treated with formic acid (2.4 g) and 10% palladium on carbon (0.7 g, slow addition). The suspension was heated to 60° C. until evolution of gas ceased, after which it was filtered through celite. The filtrate contained a crude solution of the amine 7.

A solution of 6 (9 g) in methylene chloride (100 mL) was treated with NHS (4.3 g) and DCC (4.0 g) at room temperature for one hour with stirring. The solution was filtered and added slowly to the solution of 7, which had immediately, previously been treated with triethylamine (2 mL). The solution was stirred for half an hour. More triethylamine (3 mL) was added and the solution stirred for a further hour. The mixture was diluted with water, acidified with dilute hydrochloric acid and extracted with methylene chloride (3×). The solvent was removed on a rotovap and the residue taken up in water. The suspension was filtered and extracted with methylene chloride (3×). The combined organic fractions were dried over magnesium sulphate, filtered and the solvent removed. The residue was passed down a silica gel column (200 g SiO$_2$, 4–16% MeOH/CH$_2$Cl$_2$), yielding 8 (9.8 g) as a yellow oil.

with dilute hydrochloric acid and extracted with methylene chloride (3×). Removal of solvent yielded the crude acid 9 (3.86 g).

8 (4.9 g) was added to an anhydrous solution of hydrogen chloride in ethanol (prepared from 10 mL acetyl chloride and 50 mL ethanol) and stirred at room temperature for two hours. The solution was diluted with water and extracted with methylene chloride (3×). The solvent was removed on a rotovap. The residue was dissolved in ethanol (100 mL) and treated with formic acid (0.5 g) and 10% palladium on carbon (0.2 g, slow addition). The suspension was heated to 60° C. until evolution of gas ceased, after which it was filtered through celite. The filtrate contained a crude solution of the amine 10. TLC analysis showed that all of the starting azide had been converted to a primary amine (flourescamine test positive).

A solution of 9 (3.86 g) in methylene chloride (50 mL) was treated with NHS (0.76 g) and DCC (0.96 g) at room temperature for one hour with stirring. The solution was filtered and added slowly to the solution of 7, which had immediately previously treated with triethylamine (1 mL). The solution was stirred for half an hour. More triethylamine (2 mL) was added and the solution stirred for a further hour. The mixture was diluted with water, acidified with dilute hydrochloric acid and extracted with methylene chloride (3×). The solvent was removed on a rotovap and the residue

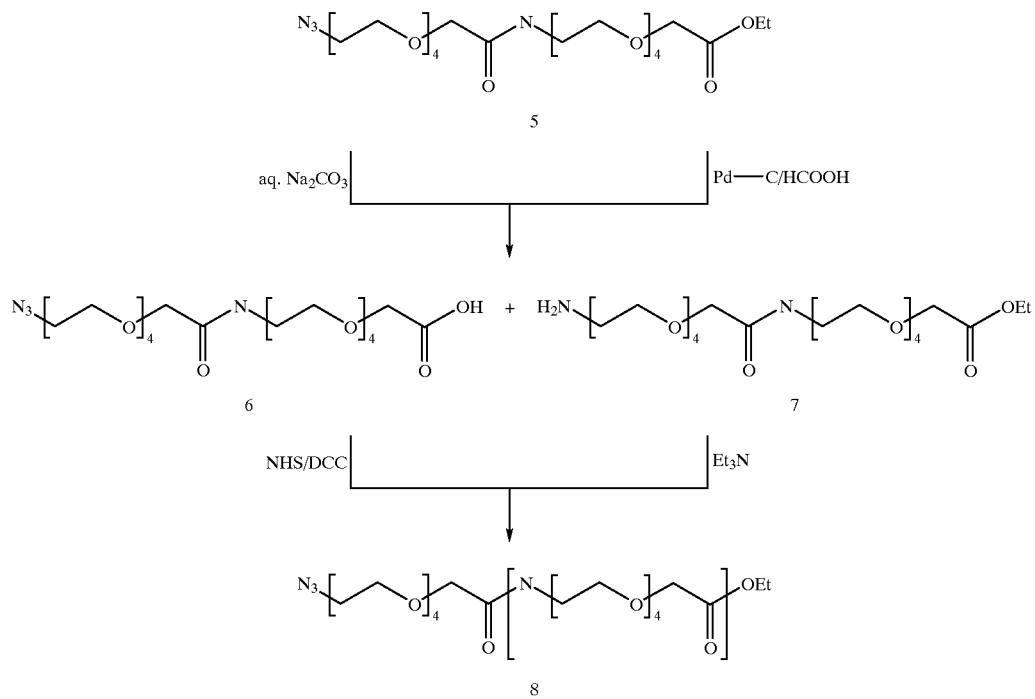

Synthesis of Ethyl-ω-azido-octa-(14-amino-3,6,9,12-tetraoxatetradecanoate) 11

A suspension of 8 (4.9 g) in a solution of sodium carbonate (2.5 g) in water (50 mL) was stirred at 45° C. until all of the oil had dissolved. The solution was stirred at 45° C. for a further half an hour and then extracted with methylene chloride (1×). The solution was acidified (pH=2)

taken up in water. The suspension was filtered and extracted with methylene chloride (2×). The combined organic fractions were dried over magnesium sulphate, filtered and the solvent removed. The residue (7.6 g) was passed down a silica gel column (200 g SiO$_2$, 4–16% MeOH/CH$_2$Cl$_2$), yielding 11 (3.9 g) as a colorless oil.

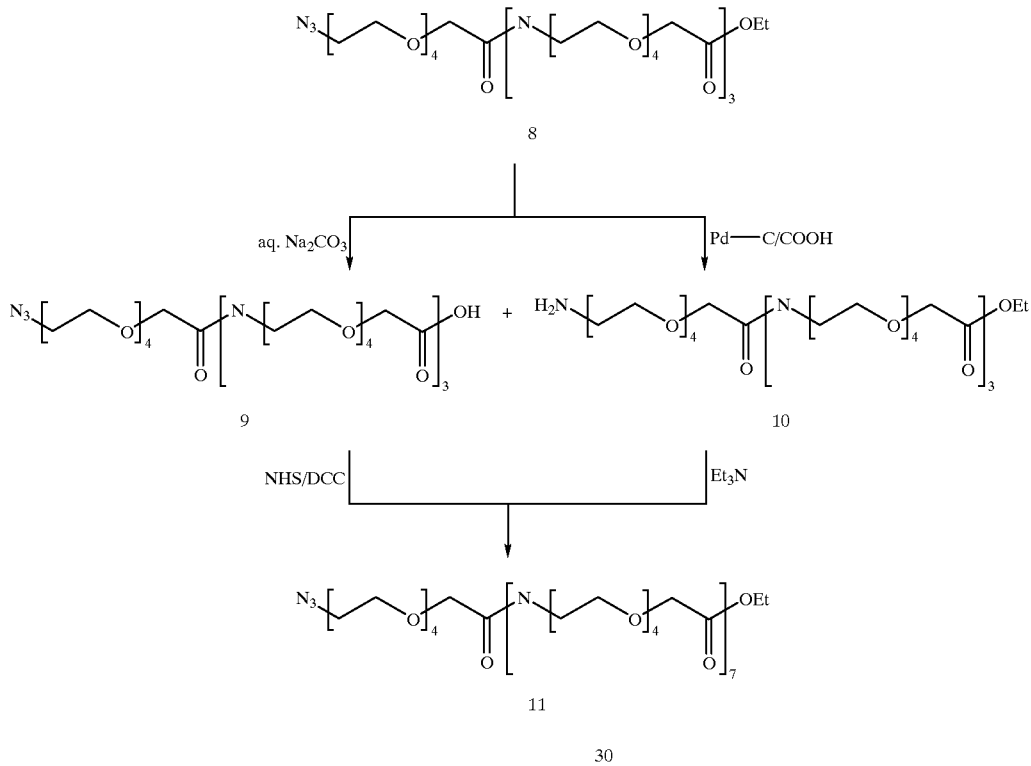

Synthesis of N-(ω-azido-octa-(14'-amino-3', 6', 9', 12'-tetraoxatetradecanoyl))-1,2-distearoyl-sn-glycero-3-phosphoethanolamine (ATTA8-DSPE) 13

11 (3.9 g) was hydrolyzed using the protocol outlined for 8, yielding 3.5 g of the crude acid 12. A solution of 12 in chloroform (50 mL) was treated with NHS (0.66 g) and DCC (0.44 g) at room temperature with stirring for one hour. The solution was filtered and treated with DSPE (1.35 g). The suspension was warmed to 60° C. until most of the DSPE had dissolved. Triethylamine (0.5 mL) was added and the solution warmed until all solids had dissolved. The solution was stirred at room temperature for one hour, diluted with water and carefully acidified to pH 5 with dilute hydrochloric acid. The mixture was extracted with methylene chloride (3×). The solvent was removed on a rotovap. The residue was taken up in water, filtered and extracted with methylene chloride. The solvent was removed on a rotovap. The residue was suspended in methanol, centrifuged at 3000 rpm for one hour and the supernatant decanted. The solvent was removed on a rotovap. The residue was then taken up in water, filtered through a 0.22 μm filter and lyophilized. Column chromatography (100 g $SiO_2$, 4–100% $MeOHCH_2Cl_2$), followed by uptake in water and lyophilization, yielded 13 (1.76 g) as a sticky white powder.

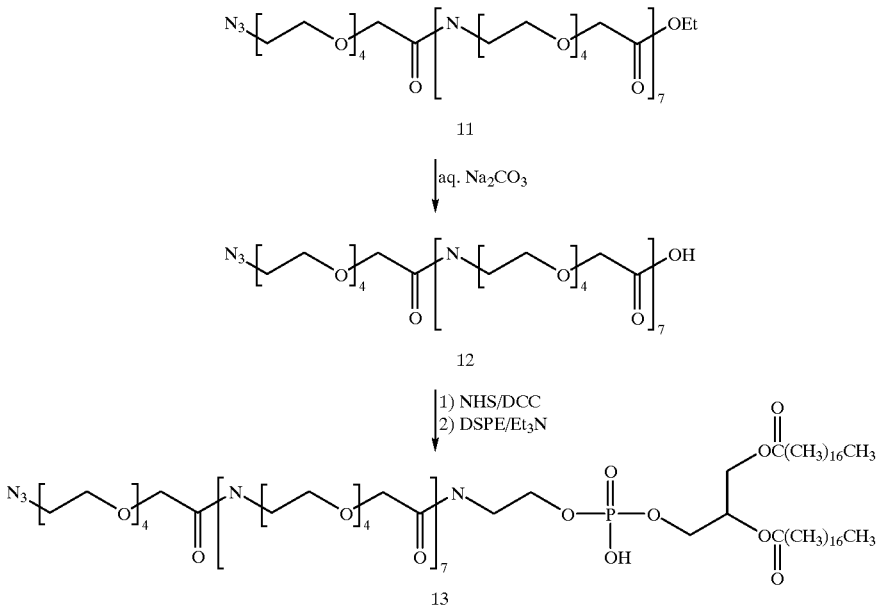

Example II

This example illustrates the synthesis of N-(ω-azido-octa-(14'-amino-3'-6'-9',12' tetraoxatetradecanoyl))-1,2-dioleoyl-sn-glycero-3-phosphoethanolamine.

Synthesis of N-(&)-azido-octa-(14'-amino-3'-6'-9',12' tetraoxatetradecanoyl))-1,2-dioleoyl-sn-3-glycero-phosphoethanolamine (ATTA8-DOPE) 14

11 (1.2 g) was hydrolyzed as using the protocol outlined for 8 with a solution of aqueous sodium carbonate (0.3 g in 20 mL), yielding 1.1 g of the crude acid 13. A solution of 13 in chloroform (10 mL) was treated with NHS (0.15 g) and DCC (0.16 g) at room temperature with stirring for one hour. The solution was filtered and treated with DOPE (0.32 g). Triethylamine (10 drops) was added. The solution was stirred at room temperature for an hour, diluted with water and carefully acidified to pH 7 with dilute hydrochloric acid. The mixture was extracted with methylene chloride (5×). The solution was dried over anhydrous magnesium sulphate, filtered and the solvent removed on a rotovap. The residue was taken up in water, centrifuged at 3000 rpm for one hour. The supernatant was filtered through a 0.22 μm filter and lyophilized. Column chromatography (70 g $SiO_2$, 4–100% $MeOH/CH_2Cl_2$), followed by uptake in water and lyophilization, yielded 13 (0.3 g) as an oil. An additional 0.8 g of a mixture of 13 and 14 was also recovered but not further purified.

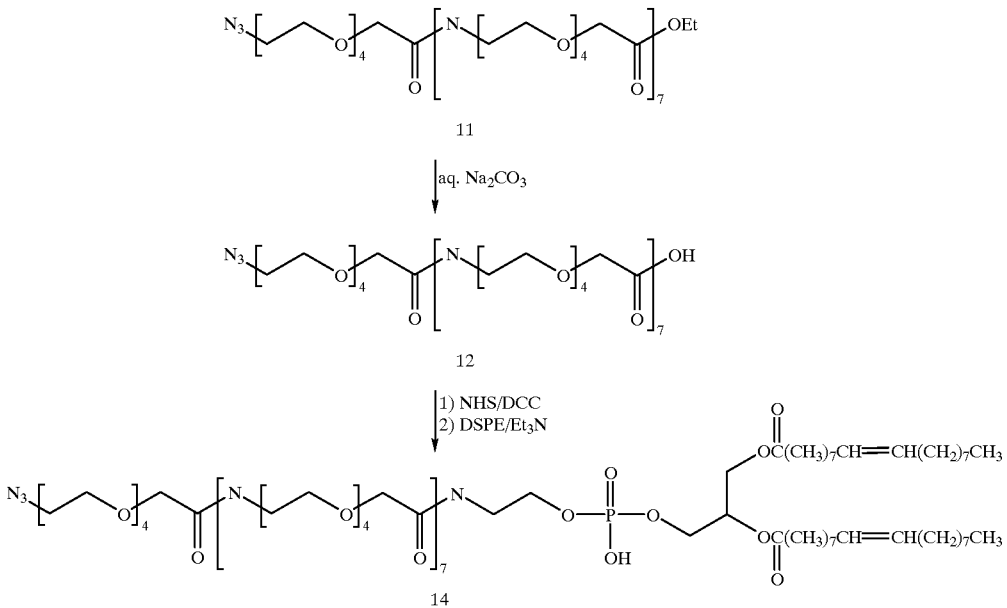

Example III

Figure 4:
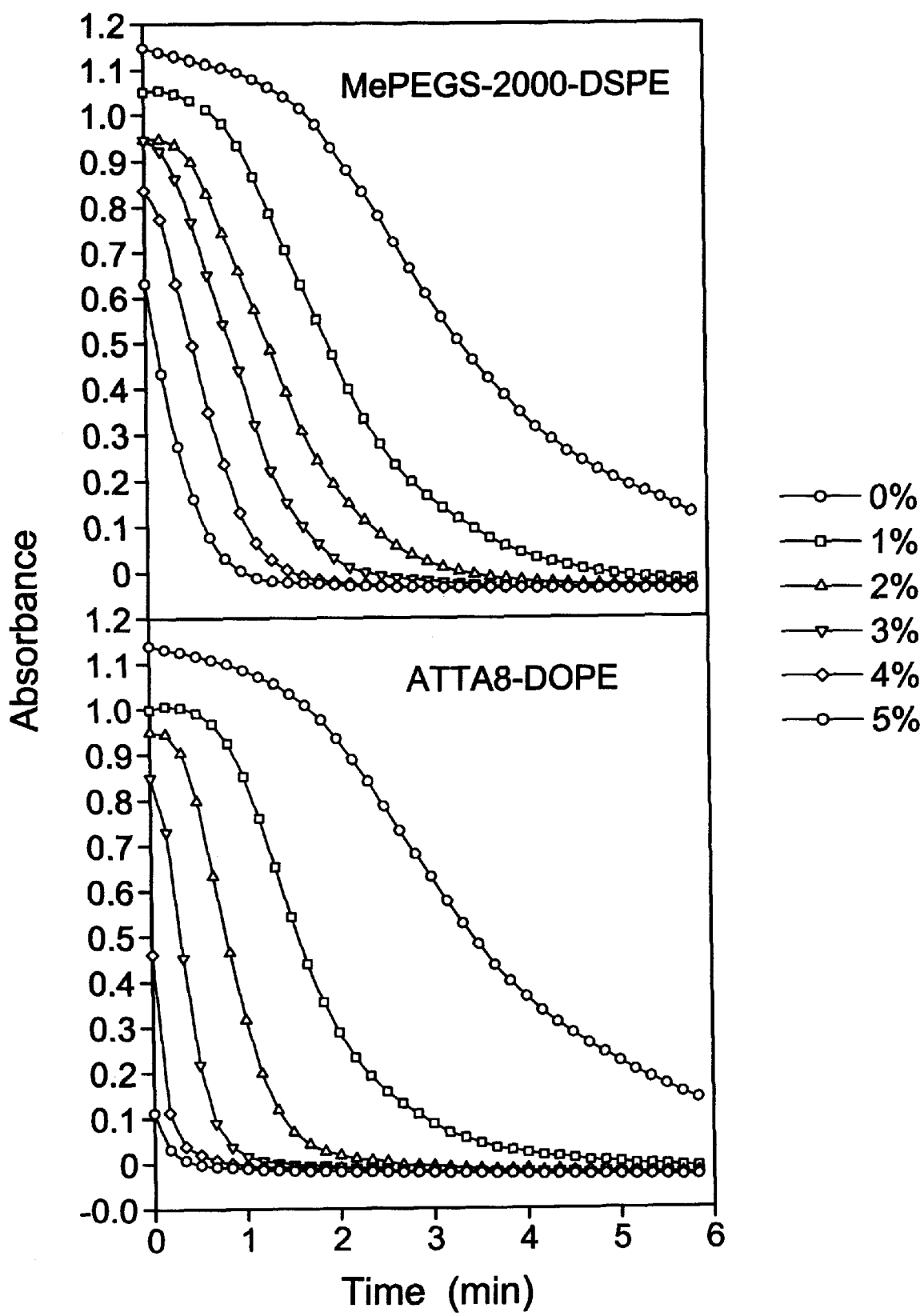
FIG. 4 illustrates inhibition of aggregation of stearylamine/POPC (5:95)—DOPS/POPC (20:80) systems using the compounds of the present invention.

This example illustrates inhibition of aggregation-disaggregation reactions as shown in FIG. 4.

Liposome Preparation

Liposomes were prepared as described by Hope, et al. Briefly, lipid mixtures of the appropriate composition were dissolved in chloroform and concentrated to a homogenous film under a nitrogen stream in a warm water bath. The film was then dried overnight in a lyophilizer. The dried lipid was hydrated in HBS at 45° C. (approximate lipid concentration of 40 mM) and the resultant multilameliar vesicles frozen in liquid nitrogen and thawed at 45° C. five times before being extruded through two stacked polycarbonate 100 nm filters (Nucleopore) using an extrusion device (Lipex Biomembranes, Inc., Vancouver, Canada) at 45° C. Lipid concentrations were determined using a phosphate assay, following which the liposomes were diluted with buffer to the desired concentration.

Lipid Assay

Samples with an estimated phosphate content in the range 50–150 nmol were digested in perchloric acid (0.7 mL) at 180° C. for one hour. The samples were allowed to cool. Ammonium molybdate solution (7 mL, prepared by dissolving 4.4 g in 2 l of distilled water and 40 mL of sulfuric acid) and Fiske reagent (0.7 mL) were added and the solutions vortexed. The solutions were heated in a boiling water bath for thirty minutes, allowed to cool and assayed relative to a standard curve (0, 50, 100, 200 nmol phosphate) at 815 nm. Phosphate assays were performed in triplicate.

Aggregation-disaggregation Assay

Liposomes comprised of stearylamine/POPC (5:95) and DOPS/POPC (20:80) were prepared in buffer (10 mM hepes, 15 mM NaCl, pH 7.4) and diluted to 1 mM. Aliquots of the DOPS vesicles (1 mL) were added to tubes (11×). Stock solutions containing MePEGA-2000-DSPE N-(2'-O-(ω-monomethoxypolyethylene glycol $_{2000}$) hydroxyacetic acid)-1,2distearoyl-sn-glycero-3-phosphoethanolamine) and ATTA8-DOPE were prepared in ethanol or chloroform. Aliquots of each solution containing the mole equivalent of 1%, 2%, 3%, 4% or 5% of half of the total lipid (assuming that the external leaflet=~50% of the total lipid) were added to the 1 mL DOPS vesicle samples. No polymer-lipid was added to the eleventh DOPS sample. The aliqouts were incubated at 37° C. for one hour with occasional stirring, and then allowed to cool to room temperature. A UV/visible spectrophotometer was zeroed at 550 nm using the 0% sample. An aliquot of cationic liposomes (0.5 mL) was added to anionic liposomes (0.5 mL) in a cuvette and mixed vigorously. Photometric monitoring was started approximately 3 seconds after mixing. Absorbance measurements were taken at the specified timepoints for the duration of the experiment.

Example IV

Synthesis of DPG-S-ATTA8-Phe$_5$

A solution of 1,2-dipalmitoyl-sn-glycero-3-succinate (DPG-S) (1 g) in chloroform is treated with N-hydroxysuccinimide (NHS) (0.25 g) and 1-ethyl-3-(3-dimethylaminopropyl)-carbodiimide (EDC) (0.35 g) for one hour. The solution is filtered. The filtrate is washed with dilute hydrochloric acid, is dried over magnesium sulphate and filtered. Octa-(14-amino-3,6,9,12-tetraoxatetradecanoic acid) (ATTA8) (2.5 g) is added, followed by triethylamine (0.5 mL). The solution is stirred at room temperature for one hour, is washed with dilute hydrochloric acid and then is dried over magnesium sulphate. The solvent is removed by a rotovap. The residue is subjected to column chromatography over silica gel to yield DPG-S-ATTA8 as a colorless wax. A solution of DPG-S-ATTA8 (170 mg) in chloroform (1 mL) is treated with NHS (12 mg) and EDC (19 mg) for one hour at room temperature. The solution is washed with diluted hydrochloric acid and then is dried over magnesium sulphate. Next, the solution is filtered and the solvent removed under vacuum. The residue is dissolved in water and immediately added to a solution of penta-phenylalanine (100 mg) in NaHCO$_3$ buffer (pH=8.0) (2 mL). The reaction mixture is stirred at room temperature for 1 hour. The reaction mixture is extracted with methylene chloride, dried over anhydrous magnesium sulfate, and then is filtered. The solvent is removed under vacuum. The residue is subjected to column chromatography to yield DPG-S-ATTA8-Phe$_5$ as a colorless powder after lyophilization.

Example V

This data demonstrates the use of polyethylene glycol-phosphatidylethanolamines (PEG-PE) and (ATTA8-DSPE) to increase the encapsulation efficiency of therapeutic cationic peptides. These results indicate that ATTA 8 is superior to PEG in encapsulation efficiency. High encapsulation of these peptides can be achieved because of the ability of ATTA8-DSPE to provide superior negative surface charge and steric stabilization.

Lipid films (total of 100 mg of lipid) were prepared by dissolving appropriate quantities of individual lipids in 200 to 500 μL of chloroform, mixing the lipids, then removing the chloroform under high vacuum. Specifically, prepared lipid films were sphingomyelin /cholesterol/PEG-PE (50/45/5 molar ratios; prepared from 53.2 mg sphingomyelin, 26 mg cholesterol and 20 mg PEG-PE) and sphingomyelin/cholesterol/ATTA8-DSPE (50/45/5 molar ratios; prepared from 53.2 mg sphingomyelin, 26 mg cholesterol and 20 mg ATTA8-DSPE) and contained 1 μCi of 3H-cholesterylhexadecylether as a radiolabelled tracer. Films were hydrated by the addition of 1.0 mL of IntraBiotics Protegrin IB510 (an antibacterial peptide from IntraBiotics, Sunnyvale, Calif.) at 10 mg/mL in 10 mM sodium acetate and 300 mM sucrose (pH 4.5) then vortexed extensively for 2 minutes and subjected to five freeze/thaw cycles between −196° C. and 65° C. at 3–5 minutes each time. 5 μl were removed for phosphate assay to quantify the phospholipid and for liquid scintillation counting (LSC). These values were used to calculate the specific activity of the different liposomal preparations. The multilamellar vesicles were converted to large unilamellar vesicles by repeated passage, typically 10 times, of the formulations through polycarbonate filters of defined pore size (either 0.2 or 0.1 μm) at 65° C. in a Thermobarrel Extruder.

Aliquots of 200–400 μL of the large unilamellar vesicles containing IB510 were passed over a 20 cm×1 cm BioGel A-15 m (50–100 mesh) column pre-equilibrated in 150 mM NaCl and 20 mM Hepes (pH 7.5). Liposome-containing fractions were identified by LSC of 100 μL aliquots of each fraction and the 5–6 fractions with the highest lipid concentrations combined. The concentrations of liposomes and peptide were quantified by LSC and HPLC, respectively. Encapsulation efficiency was calculated from the post-column peptide/lipid ratio divided by the precolumn peptide/lipid ratio.

Results of this experiment (see Table I) indicate formulations of both IB510 in SM/chol/PEG-PE and SM/chol/ATTA8-DSPE had >85% recovery of the peptide prior to column chromatography. However ATTA8-DSPE was superior to PEG-PE in encapsulation efficiency.

TABLE 1

| Formulation (molar ratio) | Peptide/lipid after extrusion (% initial) | Encapsulation efficiency (%) | Final recovery of entrapped peptide (%) |
|---|---|---|---|
| SM/chol/PEG-PE (50/45/5) | 96.9 | 37.2 | 36.0 |
| SM/chol/ATTA8-DSPE (50/45/5) | 84.6 | 67.2 | 56.9 |

Example VI

Figure 5:
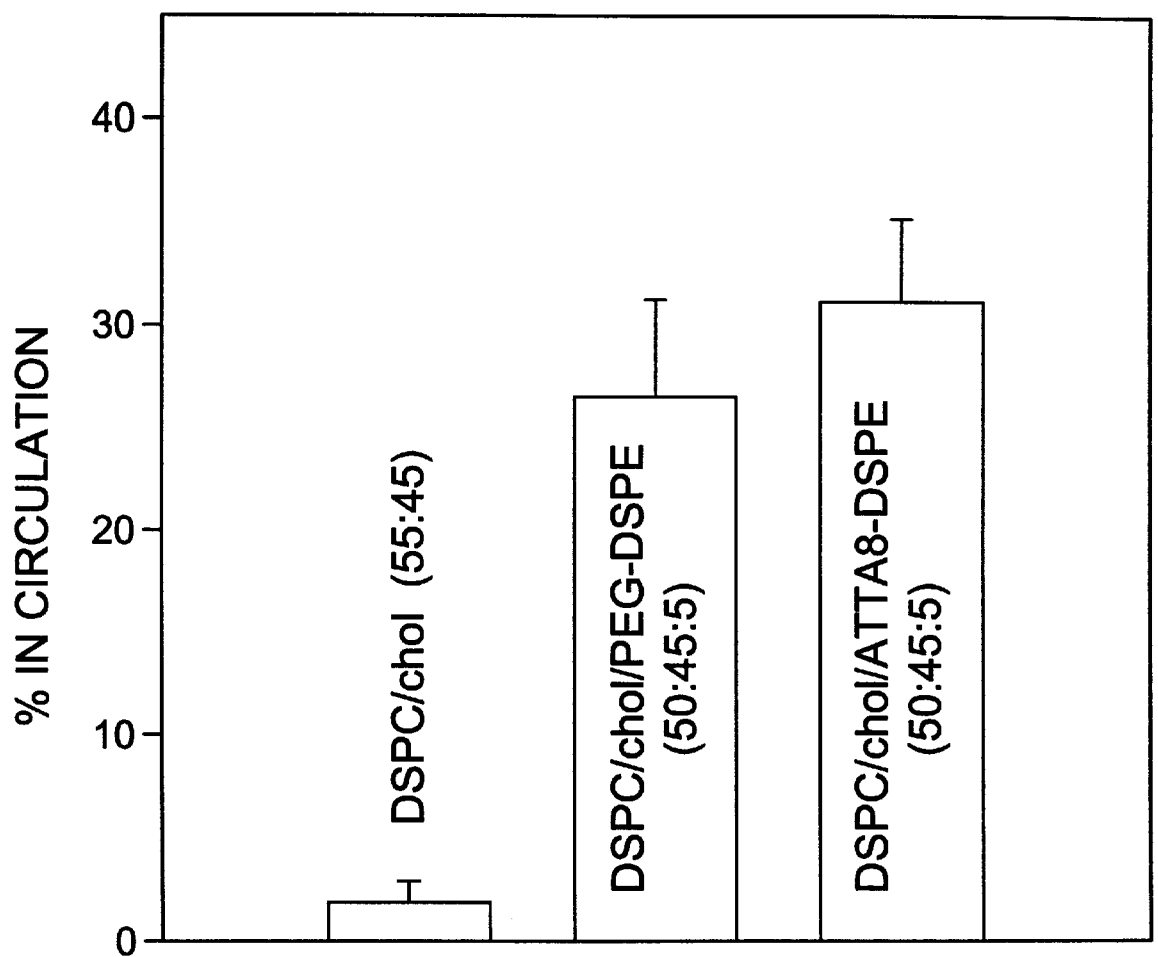
FIG. 5 illustrates in vivo clearance behavior of ATTA8-DSPE liposomes.

This data demonstrates the in vivo clearance behavior of ATTA8-DSPE liposomes. Liposomes [DSPC/chol (55:45); DSPC/chol/ATTA8-DSPE (50:45:5); DSPC/chol/MePEGA-2000-DSPE (50:45:5)] labeled with [14C]-cholesteryl hexadecyl ether were prepared in HBS (Hepes buffered saline; 10 mM Hepes, 150mM NaCl, pH7.4) and diluted to 4.5mM. Aliquots (200μL) were administered to ICR mice (6 mice per sample) by tail vein injection. The mice were sacrificed after 19 hours, the blood removed by cardiac puncture and collected in microtainer tubes with EDTA. The samples were centrifuged at 1500xg for 10 minutes and the plasma isolated. Two 100 μL samples from each mouse were counted in a scintillation counter directly in 5 mL of scintillation fluid. The percentage recovery was based on a plasma volume of 4.55% of individual mouse body weight (see, FIG. 5). The results indicate that DSPC/chol/ATTA8-DSPE was superior to DSPC/chol/PEG-DSPE as there were more liposomes in circulation using the ATTA8-DSPE.

Example VII

This example illustrates the synthesis of N-(4-azido-tetra-(14'-amino-3', 6', 9', 12'-tetraoxatetradecanoyl))-1,2-distearoyl-sn-3-phosphoethanolamine 15

With reference to FIG. 6, compound 15 was synthesized using a similar procedure as described previously for compound 13, and was isolated as a colorless powder after lyophilization. $^1$H NMR (CDCl$_3$) $^1$H NMR (CDCl$_3$)δ5.17 (m, $^1$H), 4.33 (dd, $^1$H), 4.12 (dd, $^1$H), 3.8–4.05 (m, 12H), 3.4–3.8 (m, 64H), 3.35 (t, J=5 Hz, 2H), 2.26 (m, 4H), 1.55 (bs, 4H), 1.22 (s, 56H), 0.85 (t, J=7.5 Hz, 6H).

Example VIII

This example illustrates the synthesis of N-(4-azido-octa-(14'-amino- 3',6',9',12'-tetraoxatetradecanoyl))-dimyristylamine 16

Figure 7:
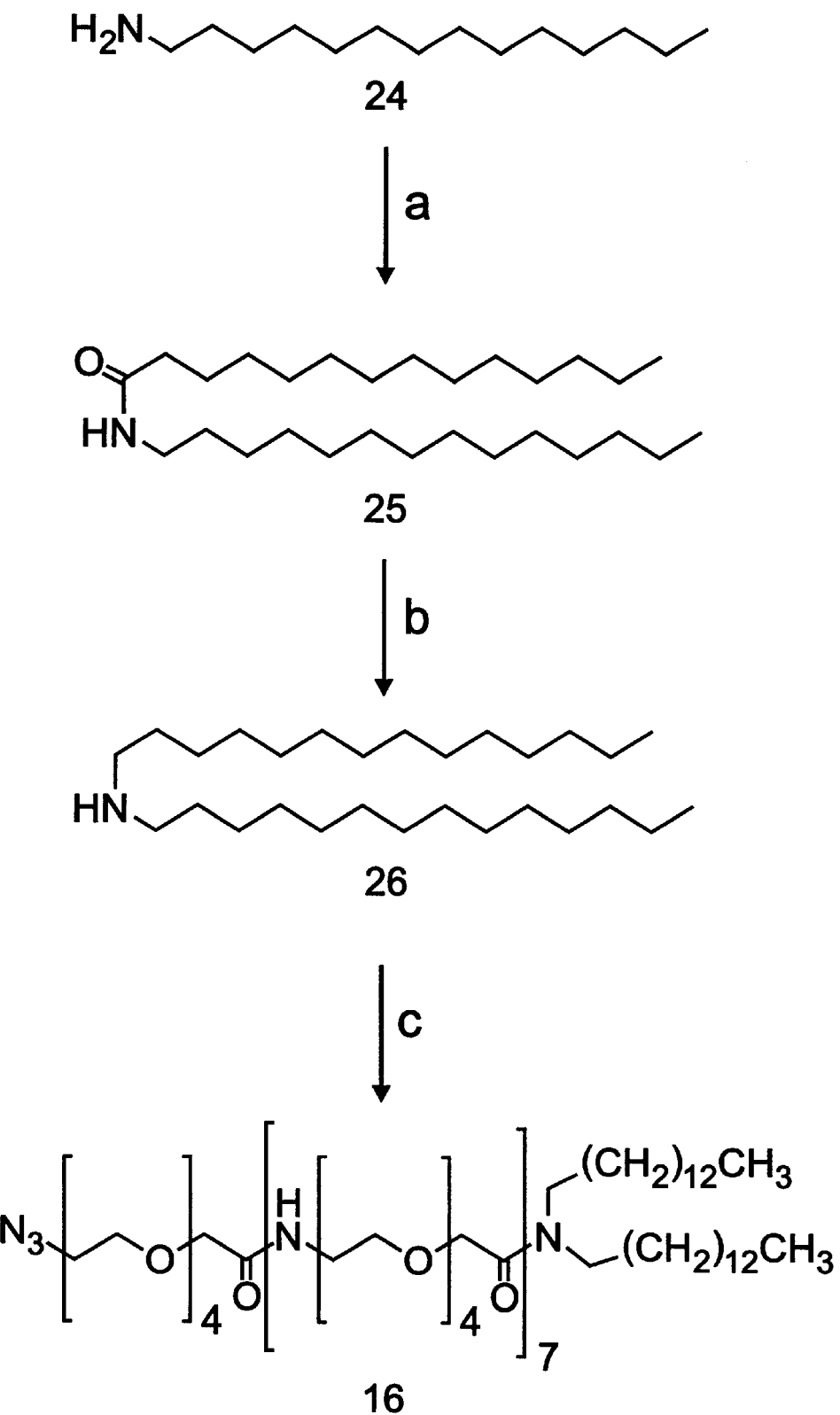
FIG. 7 illustrates the synthesis of a compound of the present invention, reagents used were (a) myristoyl chloride, $Et_3N$; (b)$LiAlH_4$, $Et_2O$; (c) NHS ester, $Et_3N$, and methylene chloride.

With reference to FIG. 7, the synthesis of compound 16 requires the synthesis of dimyristylamine 26. A solution of myristic acid (5 g) in benzene (40 mL) was treated with oxalyl chloride (2.5 mL) for 2 hours. The solvent was removed on a rotovap and the residue dissolved in benzene (20 mL). A solution of tetradecylamine 24 (2.5 g) in benzene was added. The solution was warmed to 60° C., stirred and treated with Et$_3$N (1 mL, slow addition). The reaction mixture was then allowed to stir at room temperature overnight. The suspension was then diluted with water, acidified and extracted with methylene chloride. The organic phase was dried over magnesium sulfate and the solvent removed under vacuum. The residue was passed down a silica gel column in order to remove any unreacted 24, yielding 25 (2 g) as a colorless solid. The product was suspended in ether and treated with excess LiAlH$_4$ (added slowly until vigorous evolution of gas ceased). The mixture was stirred at room temperature for one hour. Methanol was then slowly added, followed by water and finally enough dilute hydrochloric acid to acidify the mixture. The suspension was extracted with methylene chloride (the precipitate suspends in the organic phase) and the combined organic phases washed with aqueous sodium hydroxide. Column chromatography yielded 26 as a white powder (1.86 g). $^1$H NMR (CDCl$_3$) δ2.55 (t, J=7.1 Hz, 6H), 1.45 (m, 4H), 1.23 (s, 44H), 0.85 (t, J=6.7 Hz, 6H).

A solution of the acid corresponding to 16 (1.04 g) in methylene chloride (20 mL) was treated with NHS (0.10 g) and DCC (0.12 g) at room temperature for one hour. The solution was filtered and added to a solution of 26 (0.30 g) in methylene chloride (20 mL). Triethylamine (10 drops) was added and the reaction mixture allowed to stir for half an hour. The solution was then washed with dilute hydrochloric acid. The combined organic fractions were dried under vacuum and the residue redissolved in water, filtered and extracted with methylene chloride. Column chromatography yielded 16 as a colorless oil (0.62 g). $^1$H NMR (CDCl$_3$) δ7.2 (bs, ~7H), 4.16 (s, 2H), 3.98 (s, 14H), 3.1–3.7 (m, 132H), 2.2 (bm, 16H), 1.49 (bs, 4H), 1.23 (s, 44H), 0.85 (t, J=6.4Hz, 6H).

Example IX

This example illustrates the synthesis of N-(4-azido-octa-(14'-amino-3',6',9',12'-tetraoxatetradecanoyl))di(hexadecyl)amine 17.

Compound 17 was synthesized from dipalmitylamine using the method described for 16 and was obtained as a colorless oil. $^1$H NMR (CDCl$_3$) δ7.2 (bs), 4.17 (s, 2H), 3.99 (s, 14H), 3.1–3.7 (m, 132H), 1.49 (bm, 4H), 1.22 (s, 52H), 0.85 (t, J=6.52 Hz, 6H) Dipalmitylamine was synthesized from hexadecylamine using the method described for 26 and isolated as a white powder. $^1$H NMR (CDCl$_3$) δ2.57 (t, J=7.1 Hz, 6H), 1.47 (m, 4H), 1.23 (s, 52H), 0.86 (t, J=6.6 Hz, 6H).

Example X

This example illustrates the synthesis of N-(4-azido-octa-(14'-amino-3',6',9',12'-tetraoxatetradecanoyl))-rac-1',2'-dimyristoyloxypropyl-3-amine 18.

Figure 8:
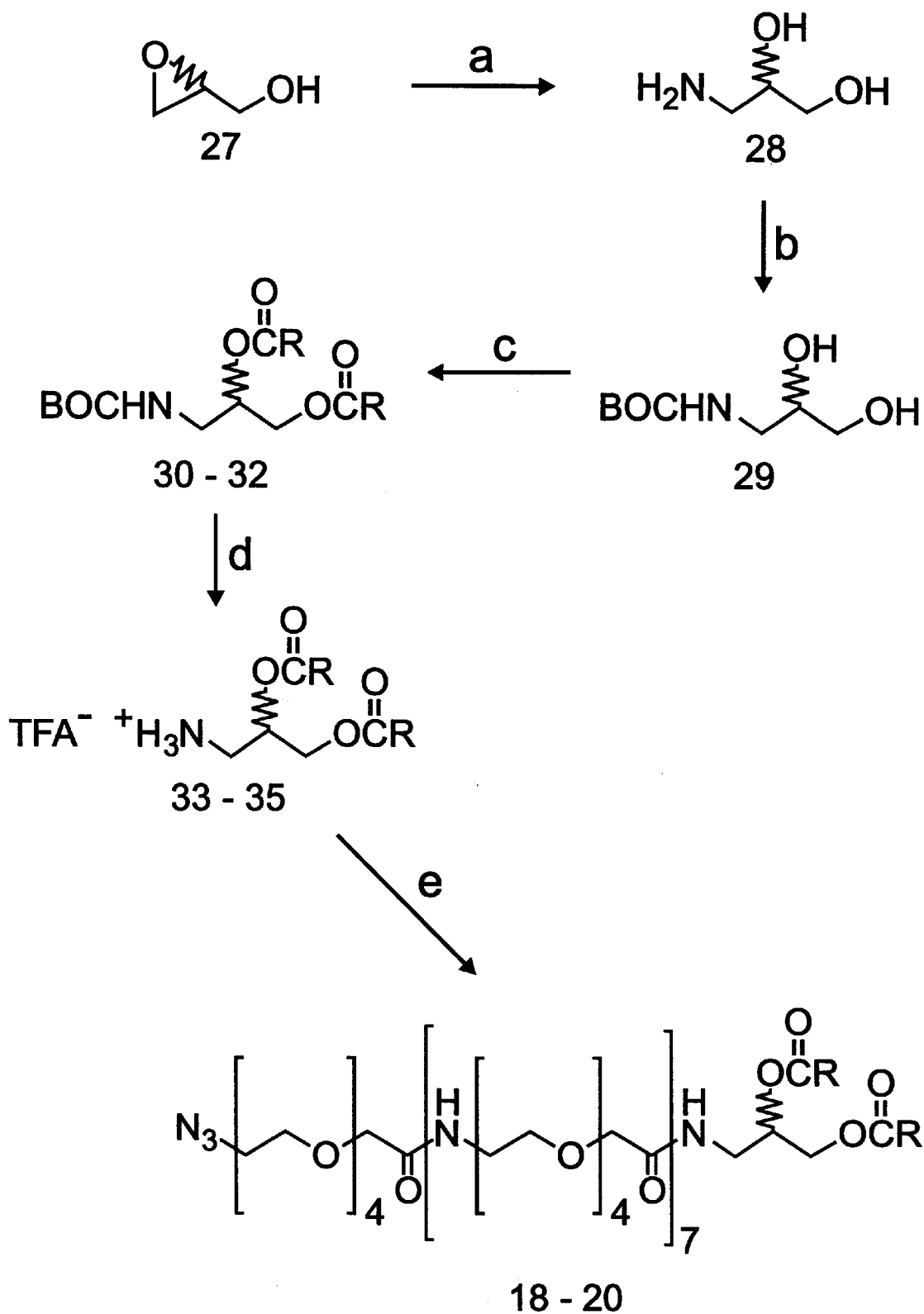
FIG. 8 illustrates the synthesis of compounds of the present invention, reagents used were (a) concentrated $NH_3$; (b) tert-butoxypyrocarbonate, $Et_3N$, EtOH; (c) acyl chloride, $Et_3N$, methylene chloride; (d) trifluoroacetic acid; (e) NHS ester, $Et_3N$, and methylene chloride.

With reference to FIG. 8, the synthesis of compound 18 proceeds via a glycidol intermediate. Synthesis of rac-3-(N-BOC)-aminopropan-1,2-diol 29 is accomplished by treating rac-Glycidol 27 (15 g) with concentrated ammonia (150 mL) overnight. The solvent was removed on a rotovap and the residue dried by azeotropic removal of water using ethanol. A solution of the residue in ethanol was treated with tert-butoxypyrocarbonate (35 g) and thriethylamine (20 mL) for four hours at room temperature. Workup followed by column chromatography yielded 29 as a colorless oil which slowly crystallized on standing. The resultant solid was dried under vacuum, yielding 29 as a colorless crystalline solid (22 g). $^1$H NMR (CDCl$_3$) δ5.39 (m, 1H), 4.08 (m, 1H), 3.94 (m, 1H), 3.70 (m, 1H), 3.52 (m, 2H), 3.17 (m, 2H), 1.40 (s, 9H).

With reference to FIG. 8, the synthesis of N-tert-butoxycarbonyl-1,2-rac-dimyristoyloxypropyl-3-amine 30 proceeded as follows. A suspension of myristic acid (3.0 g) in benzene (50 mL) was treated with oxalyl chloride (1 mL), with occasional warming, until all of the solid was dissolved and gas evolution had largely ceased. The solvent and excess oxalyl chloride was the removed on a rotovap. The residue was dissolved in benzene (50 mL) and treated with 29 (0.86 g), followed by triethylamine (1 mL). The mixture was then allowed to stir at room temperature overnight. Workup, followed by column chromatography yielded 30 (1.38 g) as a colorless powder. $^1$H NMR (CDCl$_3$) δ5.07 (m, 1H), 4.73 (m, 1H), 4.25 (dd, J=4.1 Hz, J'=11.9 Hz, 1H), 4.10 (dd, J=5.7 Hz, J'=11.9 Hz, 1H), 3.33 (bs, 2H), 2.29 (t, J=7.3 Hz, 4H), 1.59 (bm, 4H), 1.42 (s, 9H), 1.24 (s, 44H), 0.86 (t, J=6.5 Hz, 6H).

The synthesis of N-tert-butoxycarbonyl-1,2-rac-dipalmitoyloxypropyl-3-amine 31 proceeded as follows. A colorless powder (1.06 g) was synthesized as for 30 from palmitic acid (3.28 g). $^1$H NMR (CDCl$_3$) δ5.07 (m, 1H), 4.73 (m, 1H), 4.25 (dd, J=4.1 Hz, J'=11.9 Hz, 1H), 4.10 (dd, J=5.7 Hz, J'=11.9Hz, 1H), 3.33 (bs, 2H), 2.29 (t, J=7.3 Hz, 4H), 1.59 (bm, 4H), 1.42 (s, 9H), 1.24 (s, 48H), 0.86 (t, J=6.5 Hz, 6H).

The synthesis of N-tert-butoxycarbonyl-1,2-rac-distearoyloxypropyl-3-amine 32 proceeded as follows. A colorless powder (1.38 g) was synthesized as for 30 from stearic acid (3.00 g). $^1$H NMR (CDCl$_3$) δ5.06 (m, 1H), 4.72 (m, 1H), 4.25 (dd, J=4.1 Hz, J'=11.9 Hz, 1H), 4.09 (dd, J=5.6 Hz, J'=11.9 Hz, 1H), 3.32 (bs, 2H), 2.28 (t, J=7.4 Hz, 4H), 1.58 (bm, 4H), 1.41 (s, 9H), 1.24 (s, 56H), 0.85 (t, J=6.5 Hz, 6H).

General synthesis of N-(rac-2',3'-diacyoloxypropyl) ammonium triflouroacetate 33–35 proceeds as follows. Compound 30–32 (~0.90 g) was treated with neat TFA (5mL) for one hour. The solvent was removed on a rotovap and the residue recrystallized from ethanol, yielding 33–35 as fine colorless needles (84 g). 30 (0.90 g), 31 (0.90 g) and 32 (0.81 g) yielded 33 (0.84 g), 34 (0.85) and 35 (0.74 g) respectively.

Synthesis of N-(4-azido-octa-(14'-amino-3',6',9',12'-tetraoxatetradecanoyl))-rac-1',2'-dimyristoyloxypropyl-3-amine 18 proceed as follows. A solution of the acid corresponding to 16 (1.05 g) in methylene chloride was treated with NHS (0.136 g) and DCC (0.133 g) at room temperature for 1 hour. The solution was filtered and treated with 33 (0.37 g) and triethylamine (0.5 mL) at room temperature for half an hour. Following workup, 18 was isolated as a colorless oil (0.65 g) after column chromatography. $^1$H NMR (CDCl$_3$) δ5.10 (m, 1H), 4.20 (dd, J=3.4 Hz, J'=12 Hz, 1H), 4.06 (dd, partially hidden, J=6.1 Hz, J'=12 Hz, 1H), 3.95 (s, 16H), 3.2–3.8 (m, 130H), 2.25 (t, J=7.5 Hz, 4H), 1.44 (m, 4H), 1.20 (s, 40H), 0.82 (t, J=6.6 Hz, 6H).

The synthesis of N-(4-azido-octa-(14'-amino-3',6',9',12'-tetraoxatetradecanoyl))-rac-1',2'- dipalmitoyloxypropyl-3-amine 19 proceeded as follows. Compound 19 was synthesized from 34 (0.39 g, 0.121 g NHS, 0.133 g DCC, 1.01 g acid coresponding to 16) in the same way as 18, yielding 19 as a colorless oil (0.80 g) $^1$H NMR (CDCl$_3$) δ5.10 (m, 1H), 4.20 (dd, J=3.4 Hz, J'=12 Hz, 1H), 4.1 (dd, partially hidden, J=6.1 Hz, J'=12 Hz, 1H), 3.99 (s, 16H), 3.2–3.8 (m, 130H), 2.27 (t, J=7.4 Hz, 4H), 1.57 (m, 4H), 1.22 (s, 48H), 0.84 (t, J=6.2 Hz, 6H).

Synthesis of N-(4-azido-octa-(14'-amino-3',6',9',12'-tetraoxatetradecanoyl))-rac-1',2'- distearoyloxypropyl-3-amine 20 proceeded as follows. Compound 20 was synthesized from 35 (0.43 g, 0.113 g NHS, 0.133 g DCC, 1.07 g of the acid) in the same way as 18, yielding 20 as a colorless wax (0.80 g) $^1$H NMR (CDCl$_3$) δ5.10 (m, 1H), 4.20 (dd, J=-3.4 Hz, J'=12 Hz, 1H), 4.08 (dd, partially hidden, J=6.0 Hz, J'=12 Hz, 1H), 3.98 (s, 16H), 3.2–3.8 (m, 130H), 2.28 (t, J=7.5 Hz, 4H), 1.57 (m, 4H), 1.22 (s, 56H), 0.85 (t, J=6.5 Hz, 6H).

Example XI

This example illustrates in vivo immunogenicity of compounds of the present invention.

Female Balb/c mice (6–10 weeks old), 12 per group, were injected intravenously (i.v.) with 200 μL of 5 mM lipids [HBS control; DSPC/chol (55:45); DSPE/chol/MePEGA-2000-DSPE (50:14:5); DSPC/chol/ATTA8-DSPE (50:45:5)]. Four injections were given (at intervals of seven days) over a period of three weeks. A group of mice injected with 200 μL diluent over course of administration served as a base-line control. Three mice from each group were sacrificed 24 h after each lipid administration. Spleens were harvested and assayed for lipid specific clonal expansion (mitogenicity assay below) and cytokine release (ELISA assay below). The phenotypic profiles of the recovered cells were analyzed by measuring the expression of differentiation (CD22, CD4, CD8, CD11b) and activation (CD25, CD54, CD86, Ly6A/E, MHC-II) markers. Spleen cells (1×106) were stained with appropriate PE-conjugated antibodies (PharMingen, Calif.) and phenotypic analysis was performed on FACSsort flow cytometer (Becton Dickinson, Calif.).

The phenotypic profile of spleen cells recovered from mice after the $4^{th}$ injection following repeated lipid administration is shown in Table 2.

TABLE 2

| Formulation | CD4 | CD8 | CD22 | CD11b | CD25 |
|---|---|---|---|---|---|
| HBS | 25.67 | 12.93 | 52.45 | 13.78 | 1.27 |
| DSPC/chol | 22.2 | 11.92 | 57.72 | 13.23 | 1.11 |
| DSPC/chol/MePEGA-2000-DSPE | 21.99 | 21.99 | 57.74 | 13.48 | 1.36 |
| DSPC/chol/ATTA8-DSPE | 21.87 | 11.09 | 48.85 | 13.54 | 1.36 |

| Formulation | CD54 | CD86 | MHC-II | Ly6A/E |
|---|---|---|---|---|
| HBS | 18.51 | 10.46 | 57.92 | 7.75 |
| DSPC/chol | — | — | — | — |
| DSPC/chol/MePEGA-2000-DSPE | — | — | — | — |
| DSPC/chol/ATTA8-DSPE | 19.48 | 10.57 | 54.13 | 9.4 |

Example XII

This example illustrates a mitogenicity assay using compounds of the present invention.

The mitogenicity of liposomes was evaluated by measuring cellular immune response following stimulation of primary immune cells in vitro. Splenocytes from eight weeks old Balb/c untreated mice were used in cell proliferation assay. Splenocytes were tested for their ability to proliferate upon in vitro stimulation with liposomes or with polyclonal activators for T (Concanavalin A; Con A) and B cells (Lipopolysaccharide, LPS). Single-cell suspensions of lymphocytes were prepared from whole spleens in complete RPMI medium, supplemented with 5% heat-inactivated fetal bovine serum (FBS). Viability of cells was examined by trypan blue dye exclusion and exceeded 95% viability. Cells were counted on Colter Counter and were adjusted to a density of $5×10^6$/mL. 100 μl volumes of the cell suspensions were placed into triplicate flat-bottom wells of 96-well plates along with equal volumes of the appropriate liposomes. Cells were labeled with 1 μCi/well of [$^3$H]-thymidine for 48 h after incubation for 3 days with the test solutions (37° C., 5% $CO_2$). Cells were harvested on glass filters (Skatron harvester) and levels of incorporated radioactivity were measured in a beta scintillation counter (Beckman, LS 6500). Appropriate controls (mitogens or medium alone) were set up on each plate.

For the cytokine ELISA assays, splenocytes ($1×10^6$ cells/mL) were cultured in either the presence or absence of various concentrations of lipids in 24-well plates. The supernatants were collected at different times after culture initiation (24 h and 48 h) and the levels of cytokine release were (Interleukin-2 and Interleukin-4) determined by ELISA assays using the protocol and specific anti- interleukin antibodies provided by reagent mini-kit from Endogen (Endogen, Ma.). Briefly, 96-well Immulon II plates were coated overnight with anti-IL-2, or anti-IL-4 antibody. Plates were washed with PBS-Tween 20 (0.05%) and blocked with PBS-Tween 20/BSA(2%) for 1 hour at room temperature. Supernatant samples and standards (diluted in blocking buffer), were added and allowed to incubate overnight. Plates were washed and biotinylated anti-IL-2, or anti-IL-4 antibody, was added. After a 2 h incubation, plates were washed and HRP-Extravidin, followed by TMB, was added to each well. Plates were read at $OD_{450}$. The amount of cytokine was determined by comparing OD of test supernatants to a standard curve constructed from OD of serially diluted cytokine standards.

With regard to Table 3, cell proliferation and cytokine release following in vitro re-stimulation of spleen cells with 0.62 mM lipid formulations is shown. Cells were recovered from mice after the $4^{th}$ injection following repeated weekly administrations of buffer or the listed liposome compositions. Re-stimulation was performed with the same compositions used for the treatment. Cells recovered from animals treated with buffer only were treated with all compositions as a control for non specific effects.

TABLE 3

| | | $^3$H | cytokine release | |
|---|---|---|---|---|
| in vivo treatment | in vitro stimulation | DPM | IL-2 | IL-4 |
| HBS | HBS | 2544 | 0.816 | 0.588 |
| HBS | DSPC/chol | 6744 | 0.382 | 0.474 |
| HBS | DSPC/chol/MePEGA-2000-DSPE | 6085 | 0.333 | 0.328 |
| HBS | DSPC/chol/ATTA8-DSPE | 6916 | 0.67 | 0.321 |
| DSPC/chol | DSPC/chol | 2700 | 0.35 | 0.521 |
| DSPC/chol/MePEGA-2000-DSPE | DSPC/chol/MePEGA-2000-DSPE | 4144 | 0.44 | 0.44 |
| DSPC/chol/ATTA8-DSPE | DSPC/chol/ATTA8-DSPE | 4618 | 0.375 | 0.334 |

Example XIII

This example illustrates inhibition of hemolysis of erythrocytes by cationic lipids.

Preparation of sensitized sheep red blood cells (EA cells), an aliquot of whole sheep blood (a 50% solution in Alsever's; Cedarlane) was withdrawn from the stock solution and centrifuged for 10 minutes at 1500 rpm. The cells were then washed 3 times with 10 volumes of EDTA-GVB2-. The washed cells were resuspended in a volume of EDTA-GVB2- that is approximately 5 times the volume of the initial aliquot. An aliquot of the suspended cells (100 μl) of the resuspended cells was mixed with 2.9 mL of distilled water in a cuvette and the absorbance at 541 nm measured. The concentration of the cells was adjusted to $1×10^9$ cells/mL ($A_{541\ nm}$=0.385) with EDTA-GVB2-. The cell suspension was warmed to 37° C. in a shaking bath and rabbit anti-sheep red blood cell antibody (hemolysin) was added to give a final antibody dilution of 500 fold. This mixture was incubated for 30 minutes at 37° C. Following the incubation, the cells were centrifuged at 1500 rpm for 5 minutes at 4° C., the supernatant removed and the cells washed with EDTA-GVB2-. The cells were then washed two times with DGVB2+ in order to further remove any free antibody and to introduce cations into the cell suspension. Finally, the cell concentration was adjusted to 2×108 cells/mL ($A_{414\ nm}$=0.654) with DGVB2+. Cells were maintained at 4° C. at all times after preparation, and were used on the same day.

Figure 9:
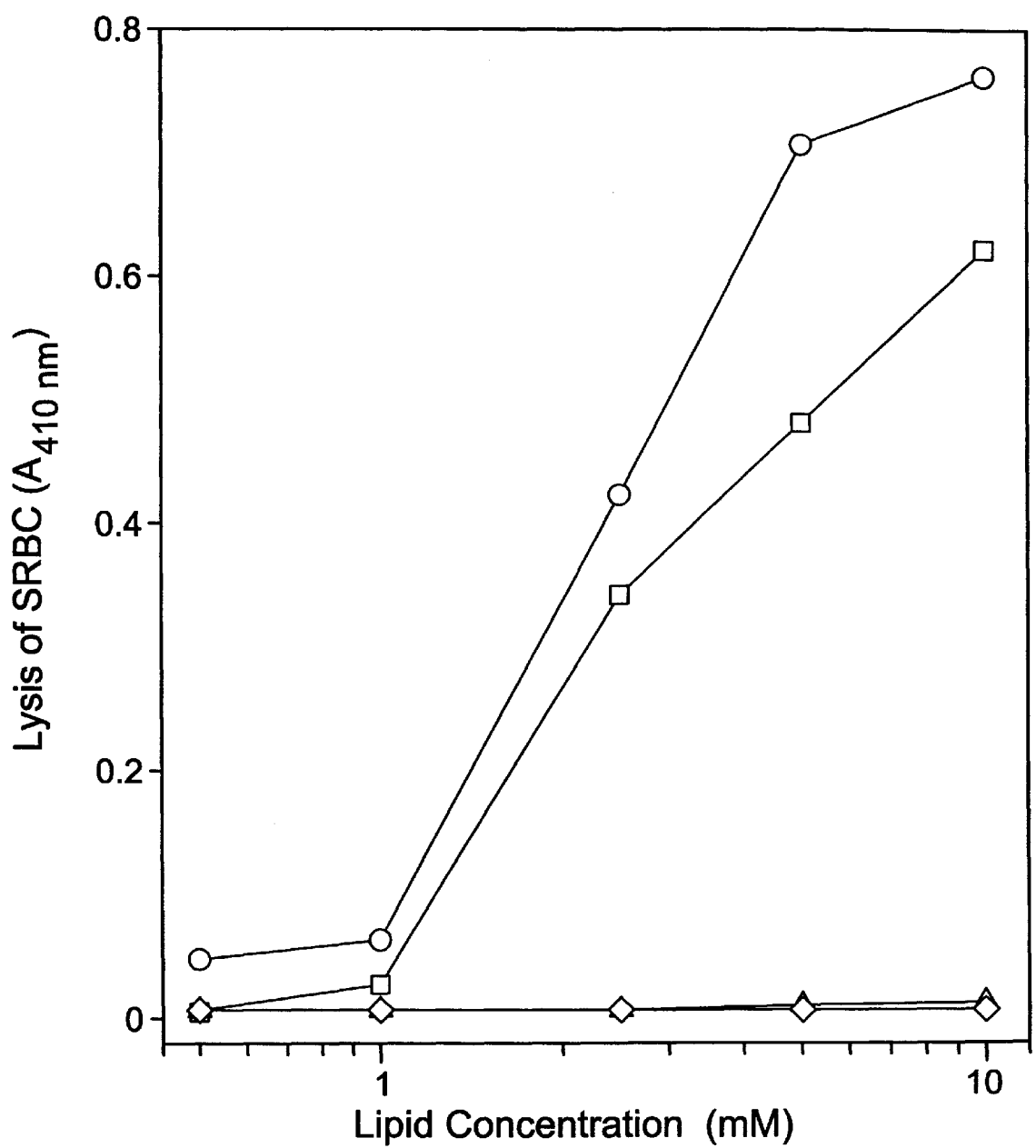
FIG. 9 illustrates the inhibition of hemolysis of erythrocytes by cationic lipids.

With regard to FIG. 9, inhibition of hemolysis of erythrocytes by cationic lipids is shown. Serial dilutions of DODAC/POPC (50:50, circles), DODAC/POPC/ATTA8-DSPE (50:40:10; diamonds), DODAC/POPC/MePEGA-2000-DSPE (50:40:10; triangles) and DODAC/POPC/MePEGS-2000-Mcer (50:40: 10; squares) liposomes (all 20 mM in VBS, 100 μL) were incubated with an equal volume of sheep red blood cells ($5×10^5$ cells) for 30 min at 37° C.

The sample was diluted with 1.0 mL of EDTA-GVB, centrifuged at 1500 rpm for 5 min, and the absorbance of the supernatant analyzed at 410 nm.

Example XIV

This example illustrates a complement activation assay.

Activation of the complement system by cationic lipid vesicles was assessed using a two step complement consumption assay previously described by Devine, D. V., Wong, K., Serrano, K., Chonn, A., and Cullis, P. R. (1994) *Liposome complement interactions in rat serum*: implications for liposome survival studies. *Biochim. Biophys. Acta* 1191, 43–51. Briefly, liposomes containing various SBL (steric barrier lipid) were prepared in VBS (20 mM, pH 7.50) and extruded through 2 stacked 100 nm polycarbonate filters using an extrusion apparatus (Lipex Biomembranes, Vancouver, Canada). Serial dilutions of the lipid vesicles (100 $\mu$l aliquoted volume) were added to an equal volume of 5x-diluted normal human serum and incubated for 30 min at 37° C. Samples were subsequently diluted with 300 $\mu$l of ice-cold DGVB2+. Aliquots (100 $\mu$L) were incubated with an equal volume of hemolysin-sensitized sheep red blood cells ($5\times10^5$ cells) for 30 min at 37° C. At the end of the incubation, EDTA-GVB (1 mL) was added to the sample to inhibit further complement activity. Samples were centrifuged at 1500 rpm for 5 min at 4° C. to remove non-lysed cells. The supernatant was then analyzed for hemoglobin content at 410 nm using a 96-well plate reader.

Figure 10:
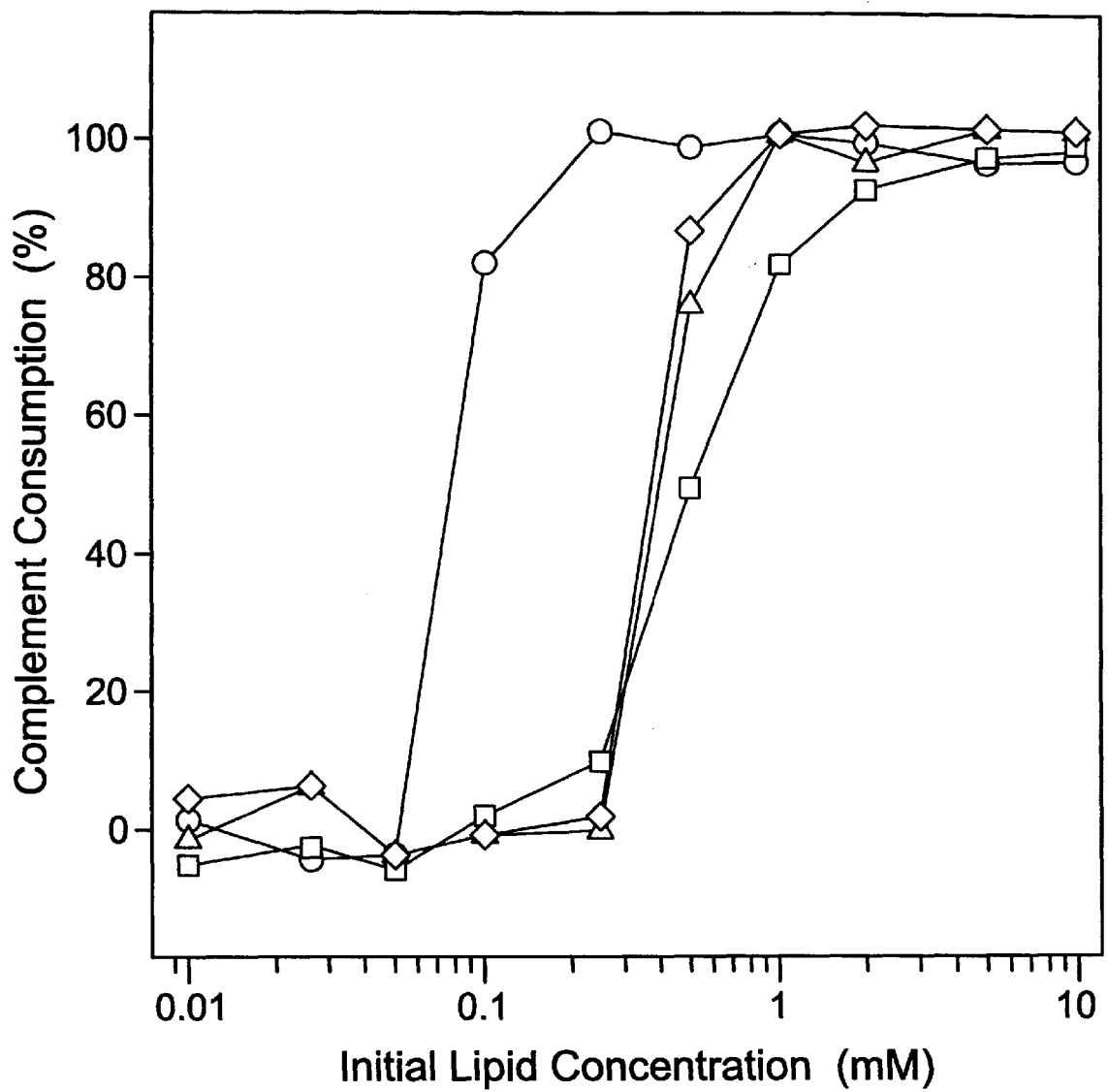
FIG. 10 illustrates the inhibition of complement activation by various vesicles.
Figure 11:
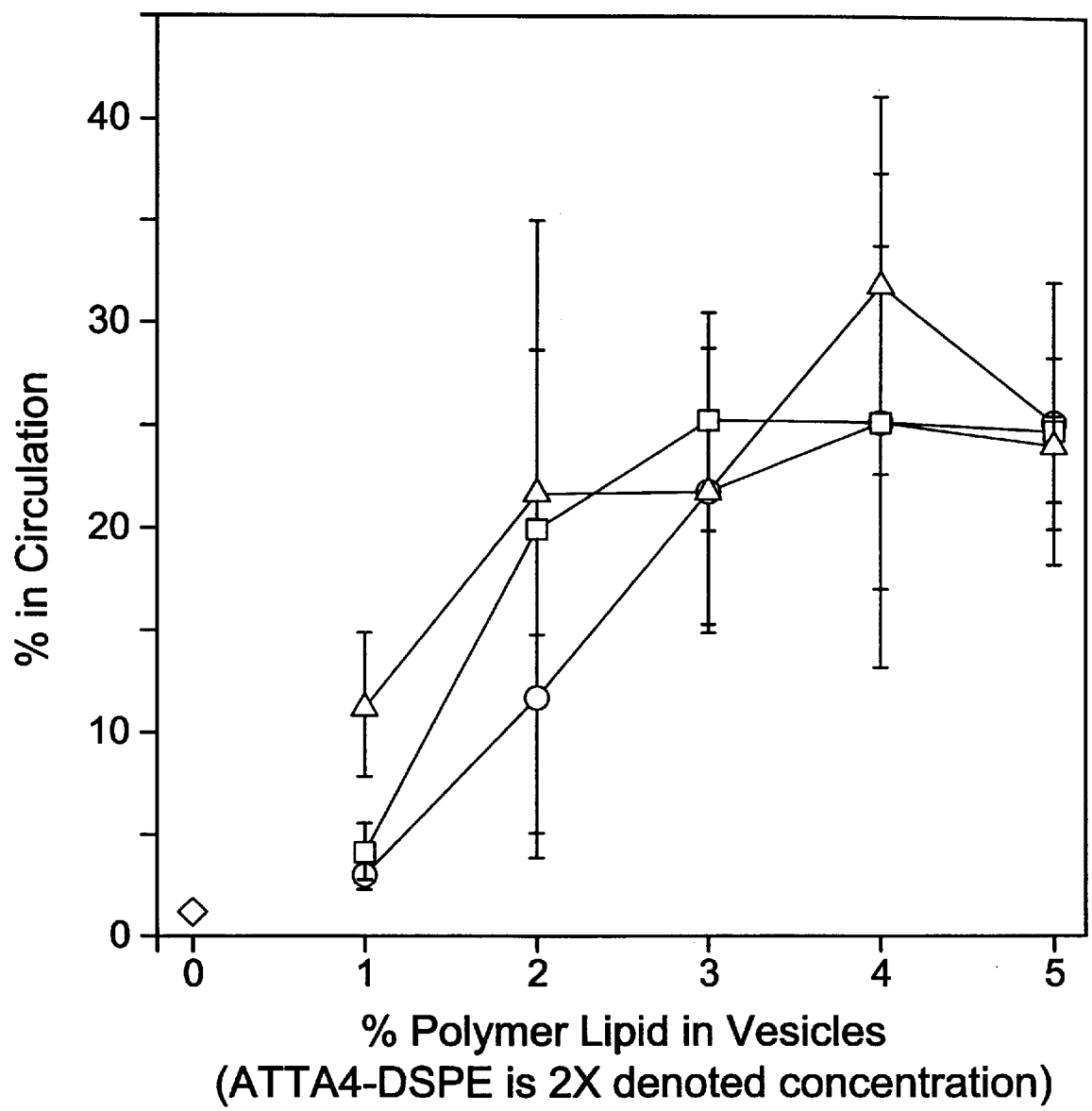
FIG. 11 illustrates clearance of sterically stabilized liposomes 20 hours post administration in female mice. [$^{14}$C]-CHE labeled liposomes composed of POPC/chol/SBL (55:45; 5 mM) were prepared in HBS (25 mM hepes, 150 mM NaCl, pH7.4) and administered to mice (200 μL per animal) by intravenous tail vein injection. Serum was collected after 20 h and analyzed for radioactivity by liquid scintillation counting. Steric barrier lipid (SBL)=MePEGA-2000-DSPE, circles; ATTA8-DSPE, squares; ATTA4-DSPE, triangles; no SBL, diamond. Error bars represent standard deviation for 5 animals.
Figure 12:
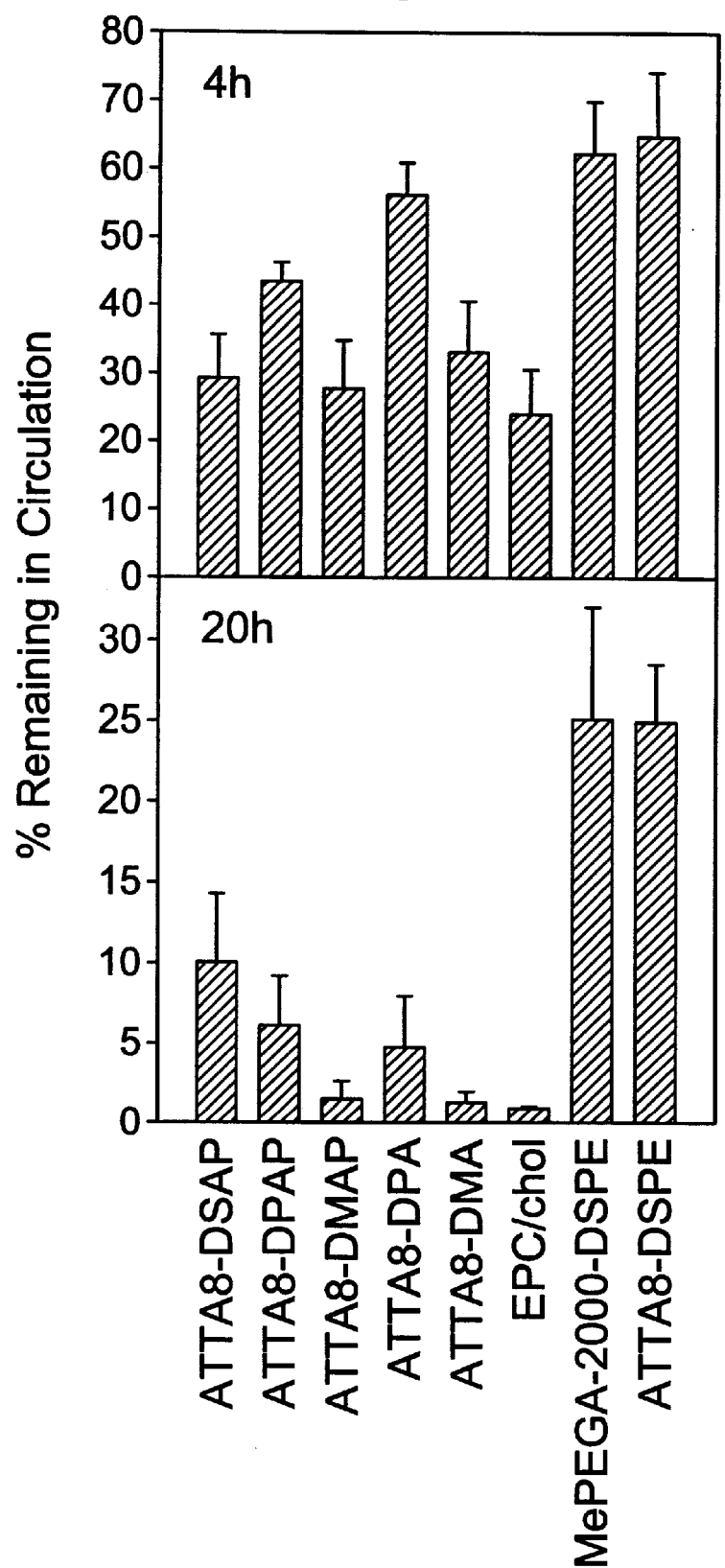
FIG. 12 illustrates clearance of sterically stabilized liposomes 20 hours post administration in female mice using neutral steric barrier lipids. [$^{14}$C]-CHE labeled liposomes composed of POPC/chol/SBL (50:45:5; 5 mM) were prepared in HBS (25 mM hepes, 150 mM NaCl, pH7.4) and administered to mice (200 μL per animal) by intravenous tail vein injection. Blood (25 μL) was collected 4 h post injection by tail nicks. Blood samples were digested in solvable and analyzed for radioactivity by liquid scintillation counting. Liposome levels were estimated based on estimated blood volume of 8%. Serum was collected after 20 h and analyzed for radioactivity by liquid scintillation counting. Liposome levels were estimated based on estimated serum volume of 4.55%. Error bars represent standard deviation for 5 animals.
Figure 13:
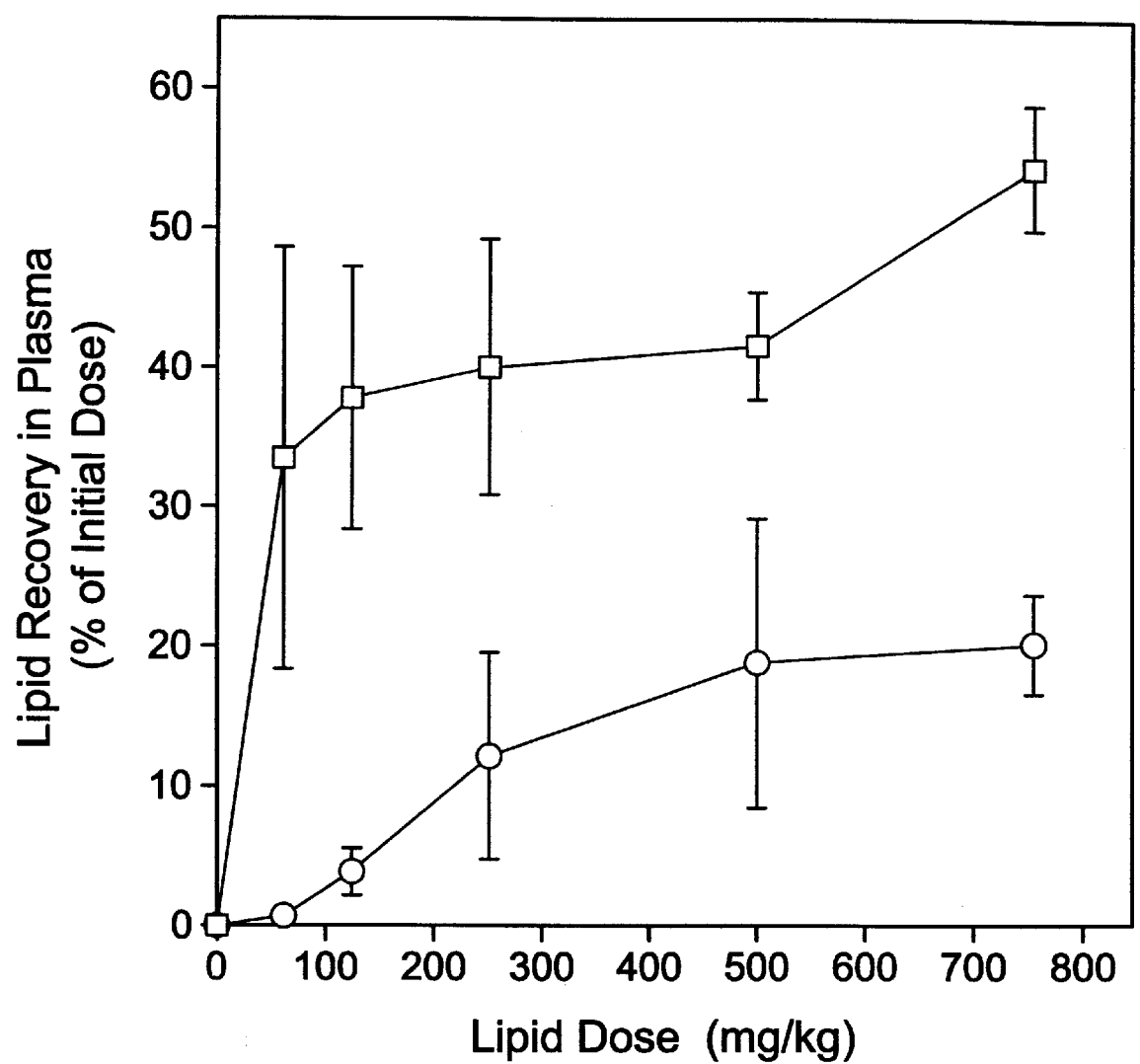
FIG. 13 illustrates lipid dose on circulation levels of antisense enscapsulated vesicles. Effect of lipid dose on circulation levels of antisense encapsulated in DSPC/chol/AL-1/SBL (20:45:25: 10) vesicles at 24 hours. SBL=MePEGS-2000-Mcer, circles; ATTA8-DSPE, squares. Error bars represent standard deviation.
Figure 14:
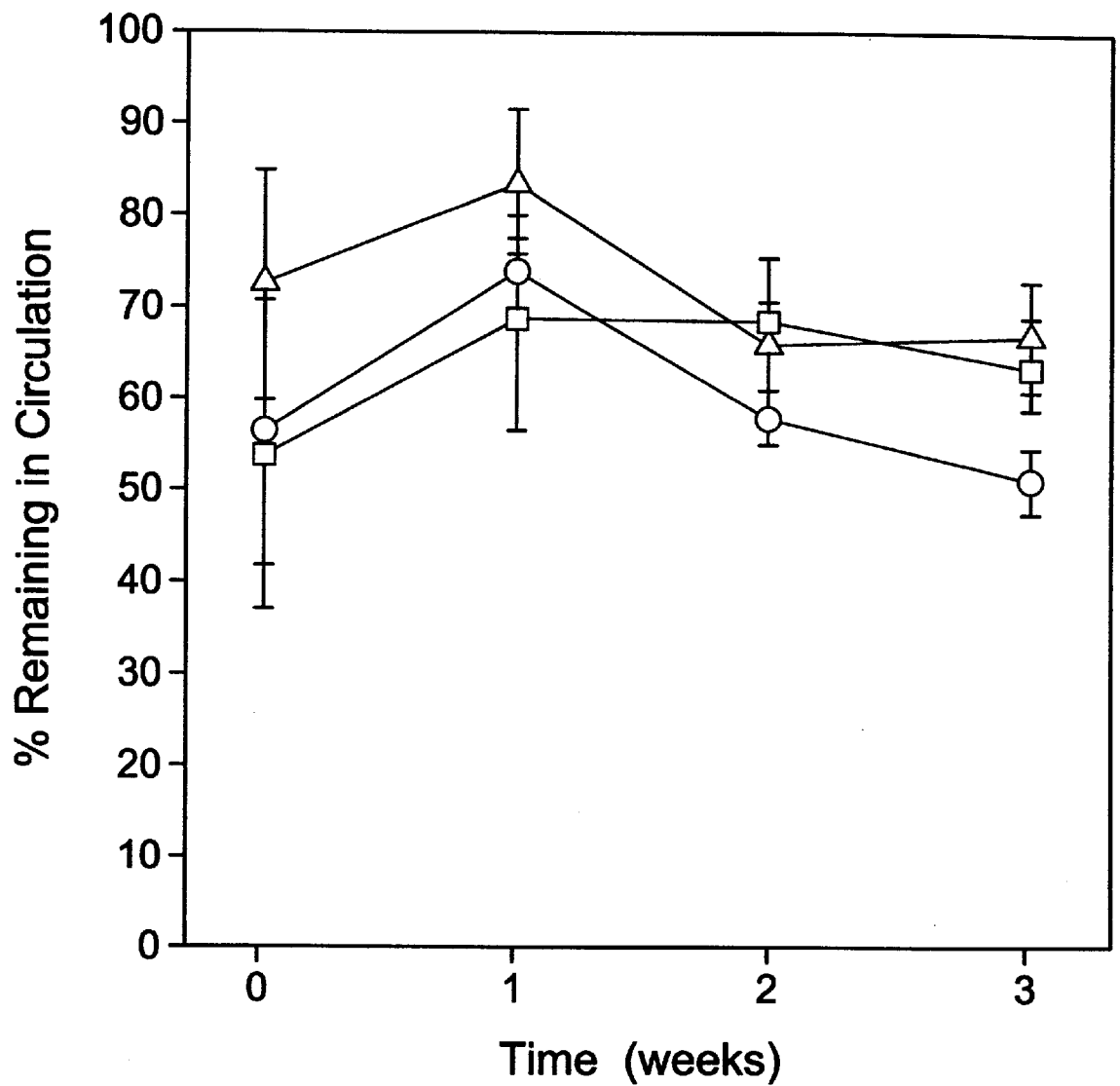
FIG. 14 illustrates clearance of liposomes 1 hour post administration in female mice subjected to weekly administrations. Liposomes [DSPC/chol (55:45, circles); DSPC/chol/ATTA8-DSPE (50:45:5, triangles); DSPC/chol/MePEGC-2000-DSPE (50:45:5, squares)] labeled with [$^3$H]-cholesteryl hexadecyl ether were prepared in HBS (Hepes buffered saline; 20 mM Hepes, 145 mM NaCl, pH7.4) and diluted such that the injected lipid dose was 50 mg/kg/week. Lipid was administered by intravenous tail vein injections (200 μL) at weekly intervals for three weeks. Blood (50 μL) was collected 1 hour post injection by tail nicks. Mice were weighed at weekly intervals to estimate blood volume (8% body weight). Blood samples were digested in solvable and analyzed for radioactivity by liquid scintillation counting. Error bars represent standard deviation for 6 animals per time point.

With respect to FIG. 10, inhibition of complement activation by DODAC/POPC/SBL vesicles is shown, i.e., DODAC/POPC (50:50, circles), DODAC/POPC/ATTA8-DSPE (50:40:10; squares), DODAC/POPC/MePEGA-2000-DSPE (50:40:10; triangles) and DODAC/POPC/MePEGS-2000-Mcer (50:40:10; diamonds).

Example XV

This example illustrates in vivo tolerability of polymer modified cationic liposomes.

Female, ICR mice, 6–8 weeks old were used for tolerability studies. Each time group consisted of at least 4 mice. All animal studies were performed in accordance with the guidelines established by the Canadian Council of Animal Care. The plasma circulation levels of DSPC:CHOL:AL-1:ATTA8-DSPE (20:45:25:10) and DSPC:CHOL:AL-1:PEG-CerC14 (20:45:25:10) containing a radiolabeled lipid marker, [$^3$H]-cholesterylhexadecyl ether, were evaluated at 24 h post administration. Mice received a single bolus dose of liposomes up to 750 mg/kg via intravenous administration in the lateral tail vein. At 24 h, mice were anesthetized with halothane and blood was collected into EDTA tubes after cardiac puncture. Mice were then terminated by cervical dislocation. Plasma levels were determined by standard liquid scintillation techniques. Plasma volumes were estimated to by 5% of total body weight. Tolerability of increasing doses of DSPC:CHOL:AL-1:ATTA8-DSPE (20:45:25:10) and DSPC:CHOL:AL-1:PEG-CerC14 (20:45:25:10) was evaluated by monitoring changes in tissue weights and enzymes typically associated with liver damage. At 24 h post-injection, tissues were excised, trimmed of fat and weighed on an analytical balance. An aliquot of the collected blood was placed in a serum tube, allowed to clot for 30 min at room temperature and assayed kinetically for alanine aminotransferase (ALT), aspartate aminotransferase (AST) and lactate dehydrogenase (LDH) according to the manufacturer's directions (Sigma Diagnostics). Clearance of sterically stabilized liposomes is shown in FIGS. 11, 12, 13 and 14.

Example XVI

This example illustrates a picogreen assay.

Picogreen working solution was prepared by diluting 1 $\mu$L of stock solution per mL of HBS. A DNA standard solution was prepared at 20 $\mu$g/mL in water. DNA standards (0–50 $\mu$L) and lipid/DNA samples (3 $\mu$L) were added to tubes. Picogreen working solution (3 mL) was added to each tube and the flouresence recorded ($T_o$) at 520 nm using excitation at 480 nm. 10% Triton X-100 (30 $\mu$L) was then added and the fluorescence recorded again ($T_f$). Entrapped DNA was calculated using the standard curve or with the equation % DNA trapped=$1-100(T_o/T_f)$.

Figure 15:
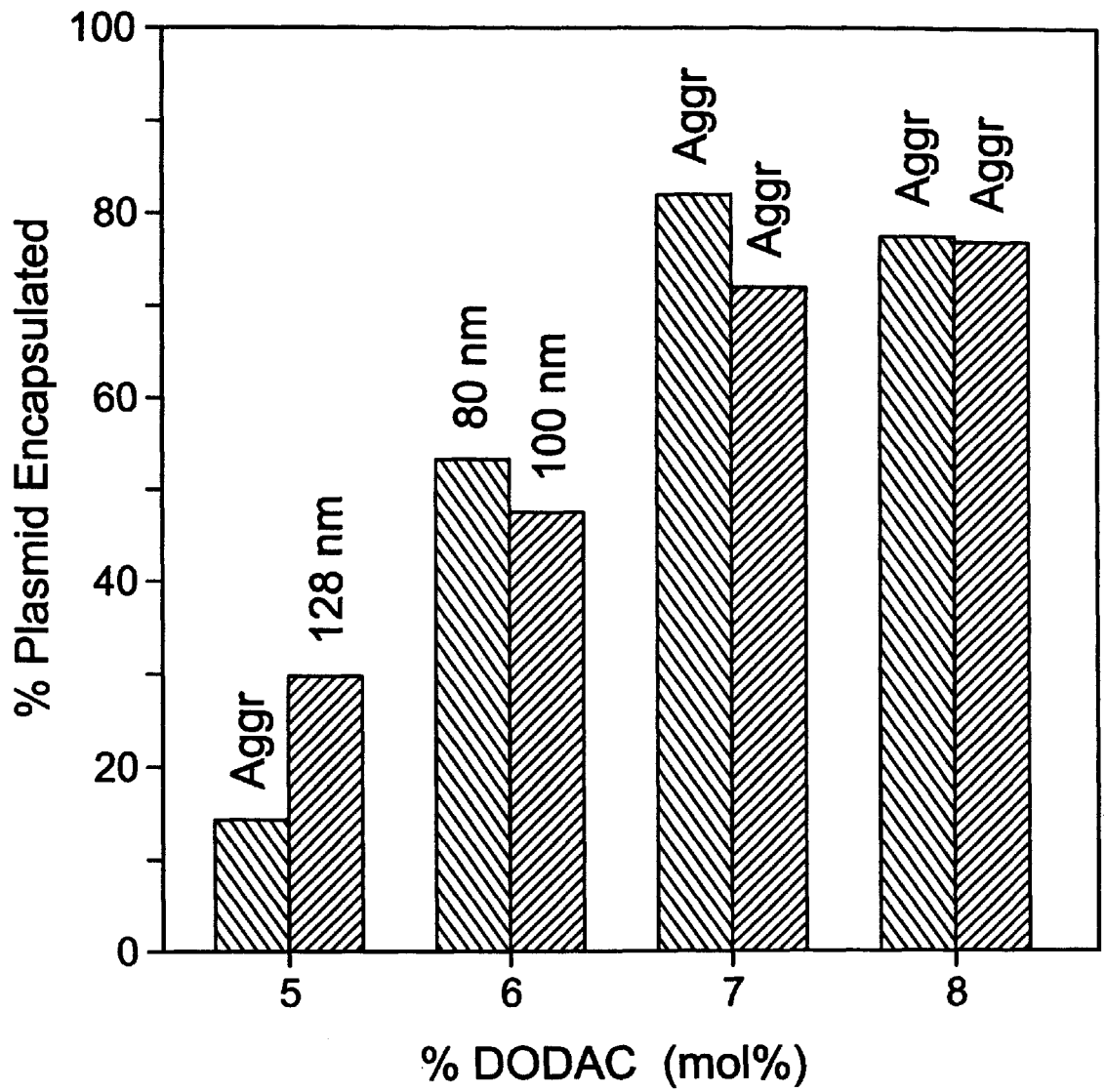
FIG. 15 illustrates the effect of SBL (steric barrier lipid) on plasmid formulation.

With regard to FIG. 15, the effect of SBL on plasmid formulation is shown pINEXL018 was encapsulated in DODAC:DOPE:SBL (n:90-n:10; n=5–8%; SBL=ATTA8-DMAP [black bars] or ATTA8-DSAP [hatched bars]) vesicles by detergent dialysis. Vesicle sizes were measured using a Nicomp Model 370 particle sizer. Encapsulation efficiency was determined using the picogreen assay.

Example XVII

This example illustrates an antisense formulation of a compound of the current invention.

Figure 16:
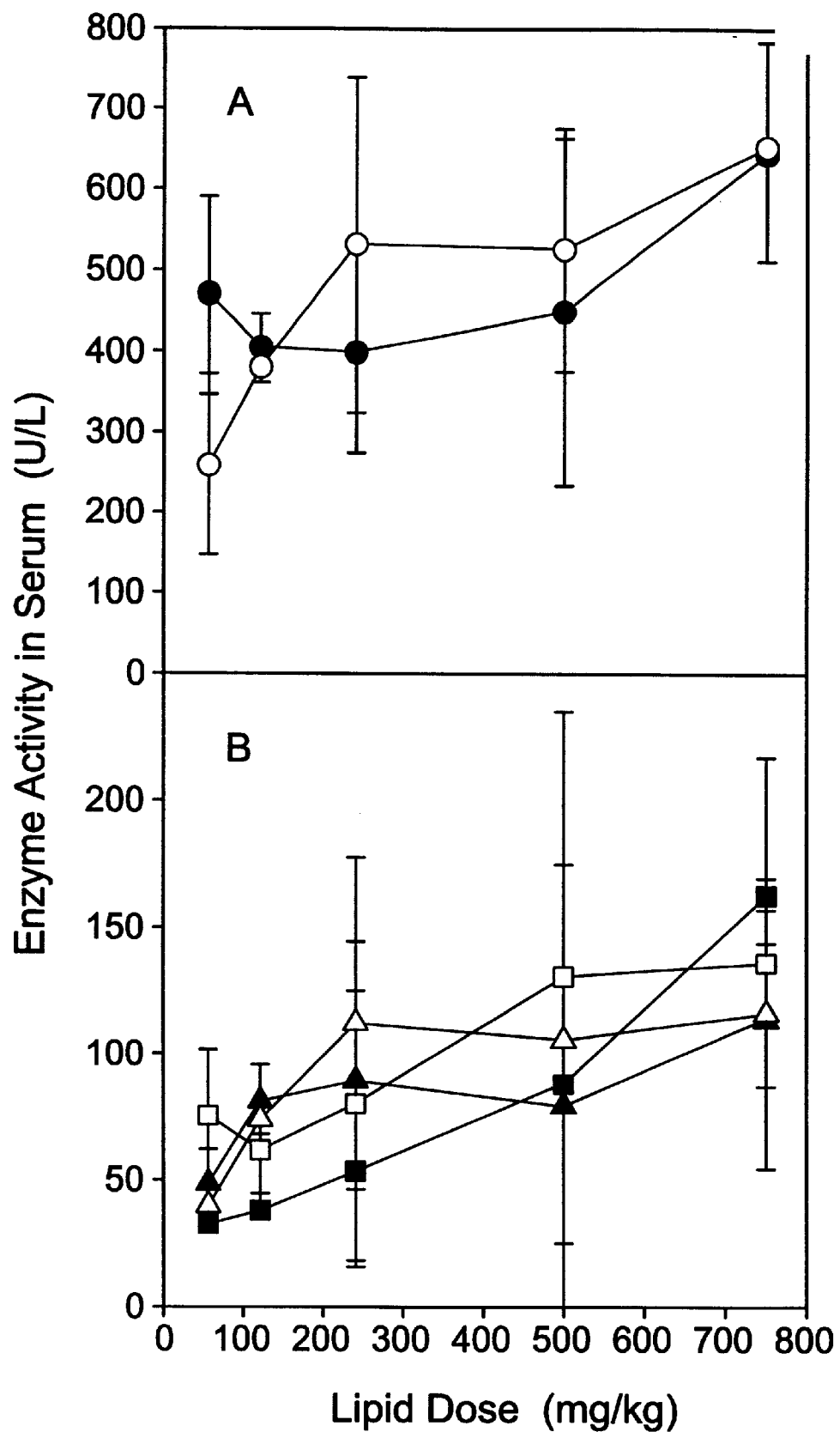
FIGS. 16A–B illustrates liver enzyme levels after administration of antisense encapsulated in DSPC/chol/AL-1/SBL (20:45:25:10) vesicles. Shaded symbols represent SBL=MePEGS-2000-Mcer, open symbols represent SBL=ATTA8-DSPE.
Figure 17:
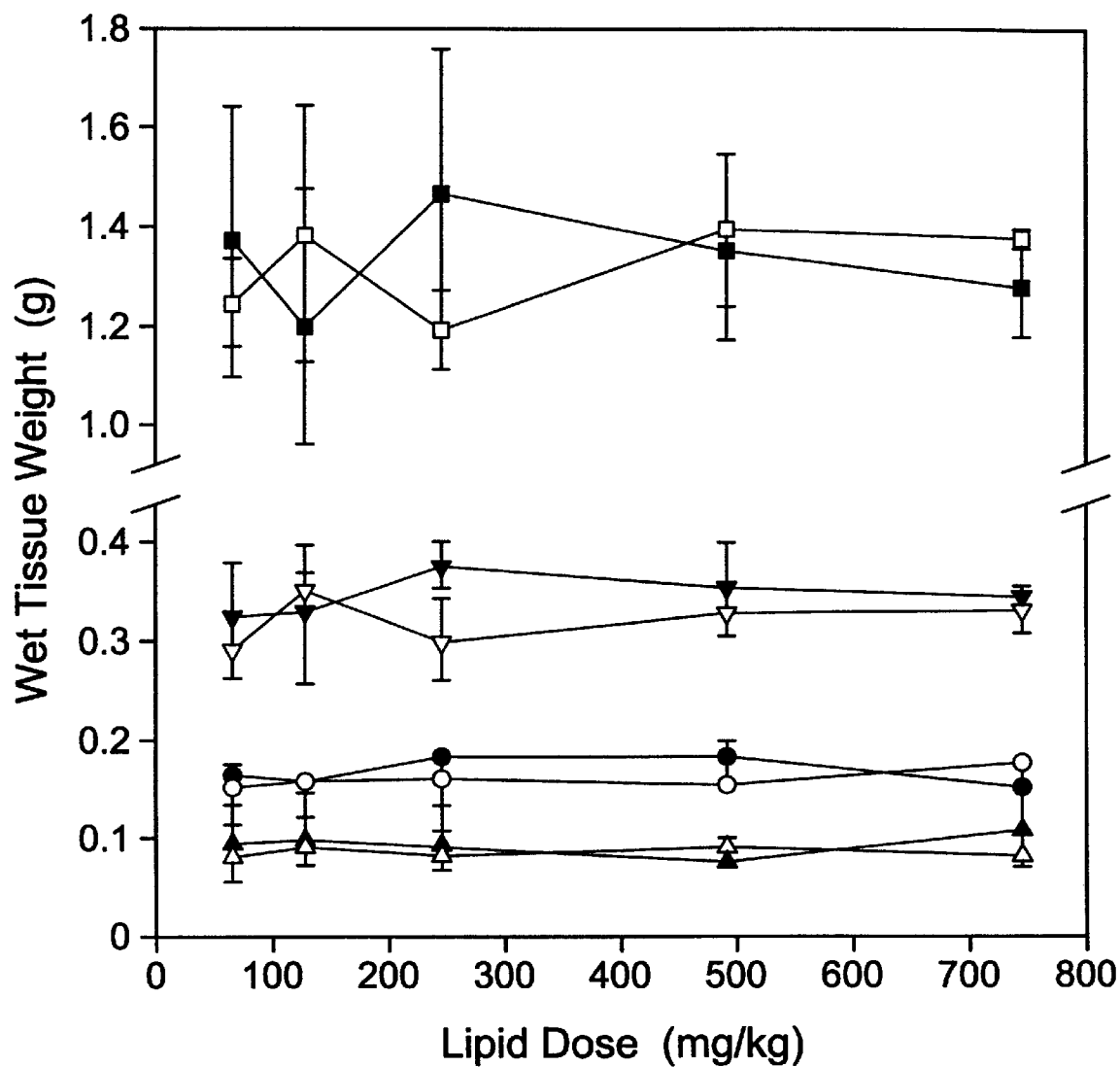
FIG. 17 illustrates single dose tolerability of encapsulated antisense oligonucleotide liposomes incorporating MePEGS-2000-Mcer (closed symbols) or ATTA8-DSPE (open symbols). Organs excised include liver (squares), kidney (inverted triangle), lung (circles) and spleen (triangle). Error bars represent standard deviation.

A stock solution of lipid (DSPC/chol/AL-1/SBL, 25:45:20:10 mole ratio, 13 $\mu$mol total lipid) in ethanol (0.4 mL) was slowly added to a solution of 20 mer antisense DNA (20 mg/0.6 mL) at 65° C. with constant vortexing. The mixture was extruded through two 100 nm filters at 65° C. as described above. The liposomes were dialyzed (3500 M.Wt. cutoff SpectraPor membrane) against citrate buffer (300 mM citrate, pH 4.0, 4000 mL) for 1–2 hours, against FBS (pH 7.4, 4000 mL) overnight and then passed down a Sepharose CL-6B DEAE column (3 mL in HBS). The lipid content was analyzed by HPLC. Antisense DNA content was determined in 1% Triton X-100 at 260 nm using the equation [DNA] ($\mu$g/mL)=$A_{260}/29.57$. Vesicle sizes were determined using a Nicomp Model 370 particle sizer. FIGS. 16 and 17 illustrate experiments using antisense formulations of the present invention.

Example XVIII

This example illustrates drug loading using compounds of the current invention.

Figure 18:
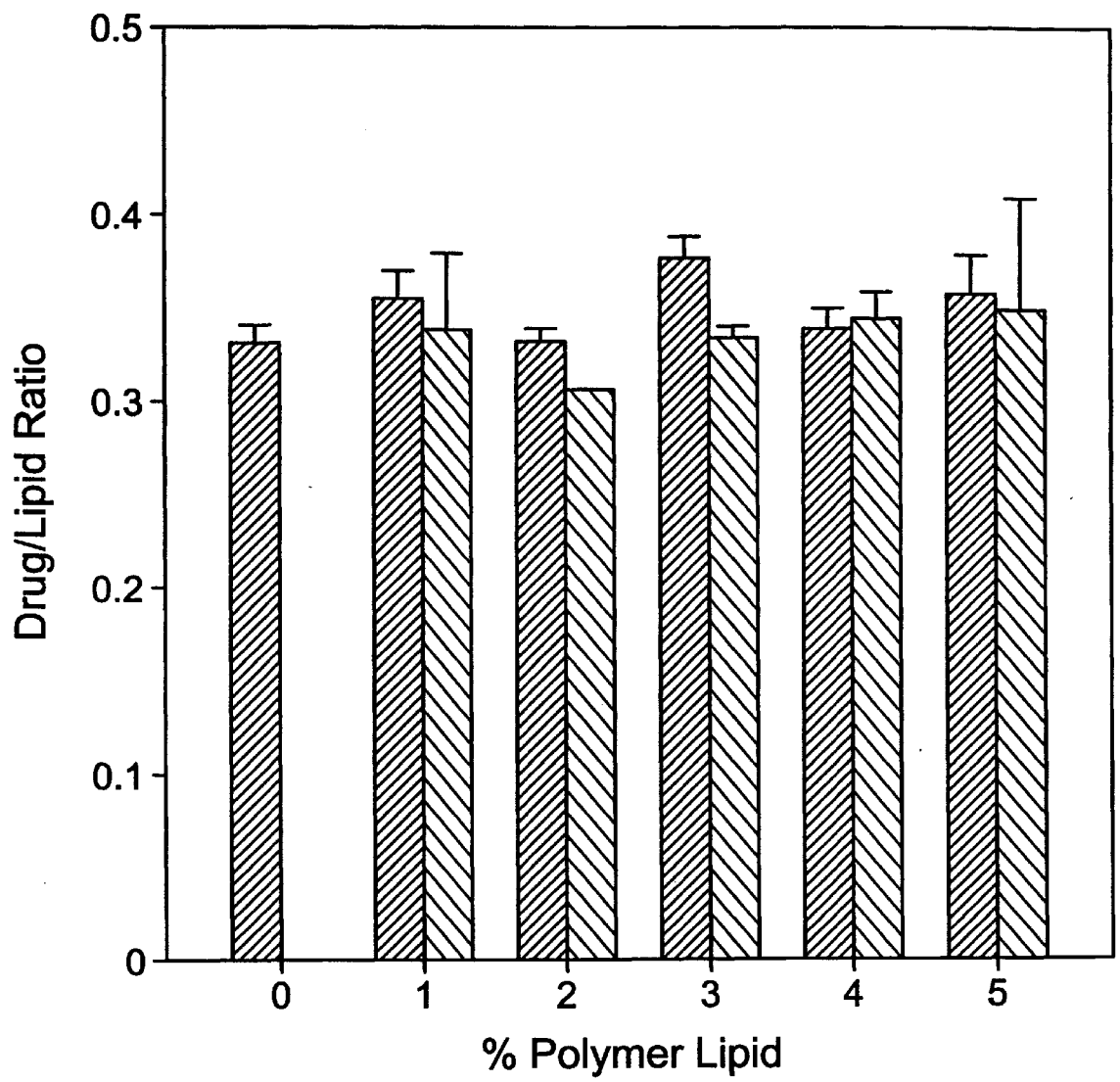
FIG. 18 illustrates effect of steric barrier lipids on drug loading.

With regard to FIG. 18, liposomes (POPC/chol/SBL (55-n:45:n; n=0 to 5; SBL=MePEGA-2000-DSPE [solid bars] or ATTA8-DSPE [hatched bars] 25 mM) were prepared in citrate buffer (300 mM citric acid, pH 4.0). Aliquots (100 $\mu$L) were added to sodium citrate buffer (300 mM sodium citrate, pH8.0; 356 $\mu$L). An aliquot (43.5 $\mu$L) from a stock solution of doxorubicin hydrochloride (10.0 mg/mL) was immediately added. Aliquots (10 $\mu$L) of potassium hydroxide solution (1N) were added in short order until the red color turned purple. The solutions were then warmed in a water bath at 60° C. for a few minutes with occasional shaking until the solutions turned dark red. The liposome suspensions were immediately passed down Sephadex G-50 columns (HBS, pH 7.4) to exchange buffer and remove any external doxorubicin. Doxorubicin content was assayed at 480 nm against a standard curve after lysis in 1% (net) Triton X-100. Lipid content was determined using the phosphate assay. With regard to FIG. 18, data represents the mean of two separate experiments. Error bars represent the range.

Example XIX

This example illustrates cytotoxicity of compounds of the current invention.

Figure 19:
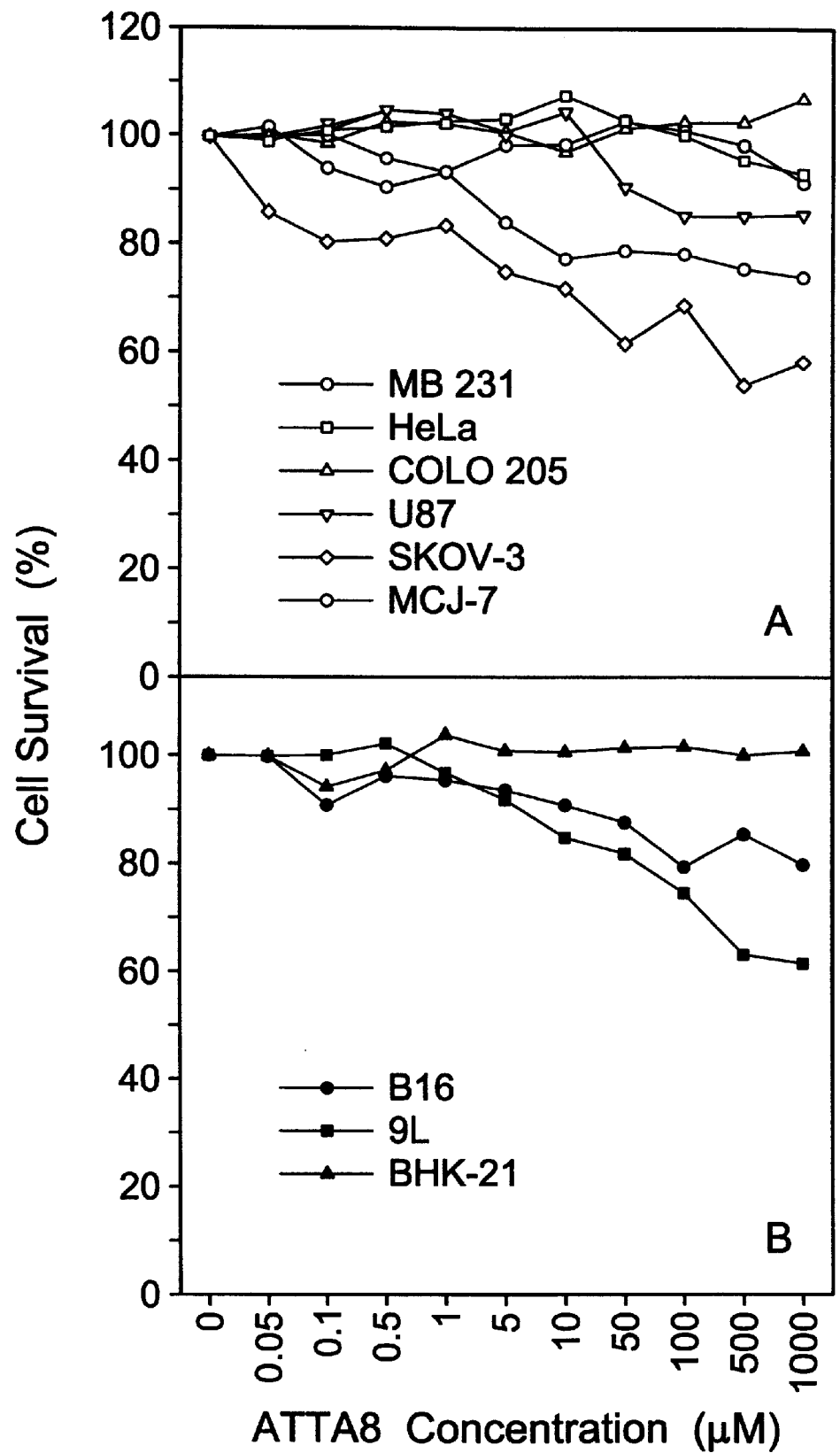
FIGS. 19A–B illustrates in vitro cytotoxity of ATTA8.

In this example, in vitro cytotoxicity of ATTA8 was examined. With regard to FIG. 19, the cell lines used (Panel A (human cell lines): MB 231, HeLa, Colo 205, U87, B16, 9L; Panel B (rodent cell lines): MCF-7, SKOV-3, and BHK-21; obtained from ATCC) were grown as monolayer cultures in T-75 flasks. The cells were subcultured twice a week at 37° C. in an atmosphere containing 5% $CO_2$ and maintained at a low passage number (5 to 10). The cells used in the assay were plated at $1 \times 10^4$ cells per well (inoculation volume: 100 μL /well) and left for 24 h at 37° C. to resume exponential growth. An equal volume (100 μL) of either complete culture medium (control wells), or test solution containing twice the final ATTA8 concentration diluted to volume with complete culture medium, was added 24 h later. Final ATTA8 concentrations ranged from between 5 μM and 1000 μM. Eight replicate wells for each test concentration were used. Cytotoxicity was evaluated 24 h later by means of the Crystal Violet assay (see, Hogan, M. M. (1997) Measurement of tumor necrosis factor. In *Current protocols in Immunology*, Vol. 1, 6.10.2., Coico, R. (Ed.), John Wiley & Sons, Inc.) In all experiments dose-response curves were plotted (values expressed as percentage of control optical density) and $IC_{50}$ values (50% inhibitory concentration) were estimated by regression analysis. The experiments were performed in duplicate.

Example XX

This example illustrates an aggregation-disaggregation assay which is for the study of ionic membrane interactions.

Figure 20:
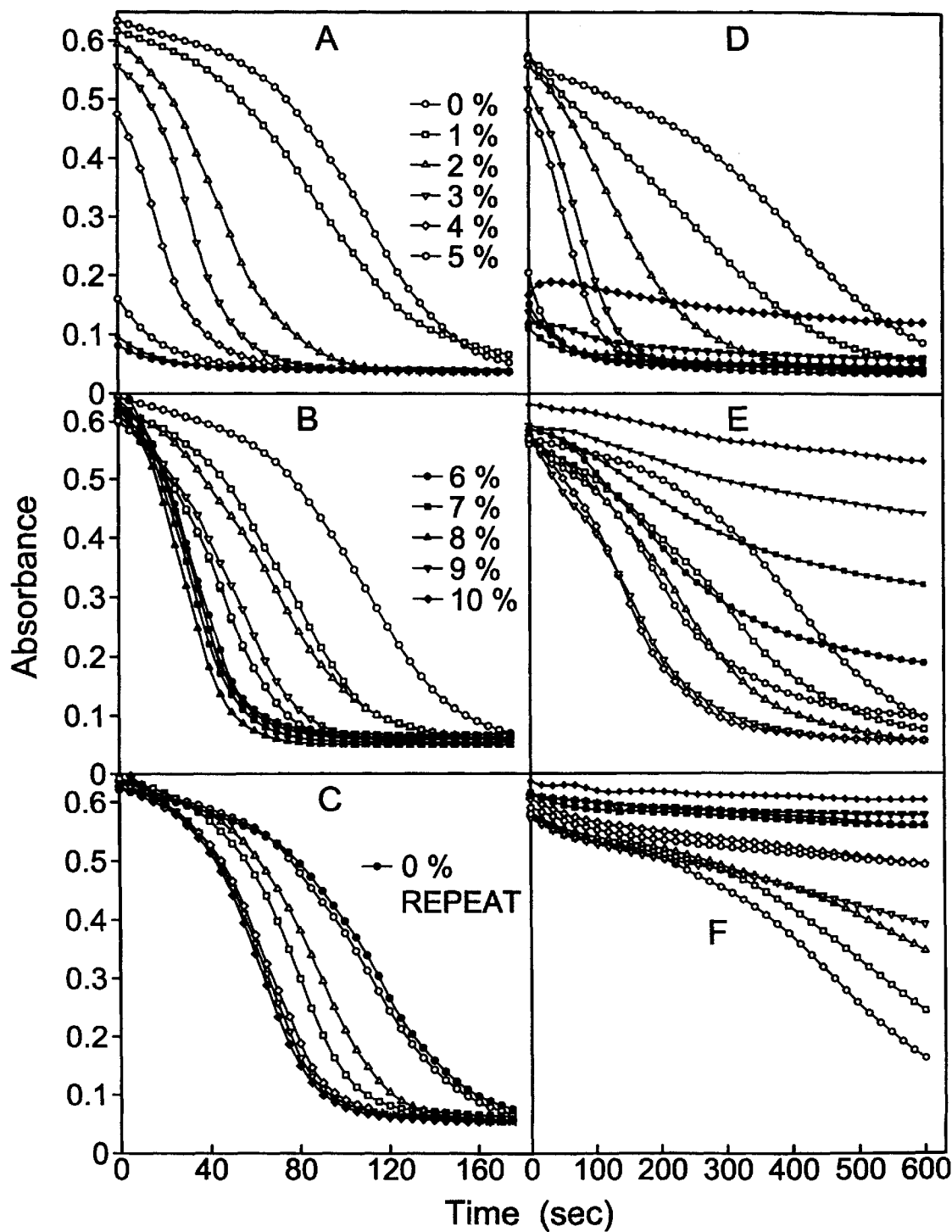
FIGS. 20A–F illustrates liposomes comprised of stearylamine/CL (5:95; CL—stearylamine, FIGS. 20A–C; CL—DODAC, FIGS. 20D–F) and DOPS/POPC/SBL (20:80-n:n; n=0–10; SBL=MePEGS-2000-DSPE, FIGS. 20A and D; ATTA8-DSPE FIGS. 20B and E; ATTA4-DSPE, FIGS. 20C and F) were prepared in buffer (10 mM hepes, 15 mM NaCl, pH7.4) and diluted to 1 mM. An aliquot of cationic liposomes (0.5 mL) was added to anionic liposomes (0.5 mL) in a cuvette and mixed vigorously. Photometric monitoring at 550 nm was started approximately 3–5 seconds after mixing. Absorbance measurements were taken at 10 second intervals for a total of 6 minutes (stearylamine) or at 15 second intervals for a total of 10 minutes (DODAC). were prepared in buffer (10 mM hepes, 15 mM NaCl, pH7.4) and diluted to 1 mM. An aliquot of cationic liposomes (0.5 mL) was added to anionic liposomes (0.5 mL) in a cuvette and mixed vigorously. Photometric monitoring at 550 nm was started approximately 3–5 seconds after mixing. Absorbance measurements were taken at 10 second intervals for a total of 6 minutes (stearylamine) or at 15 second intervals for a total of 10 minutes (DODAC).

In this example, cationic and anionic liposomes are allowed to mix, resulting in an immediate aggregation event due to charge interactions. The ionic lipids in these liposomes then slowly (or rapidly) exchange. Disaggregation occurs, under suitable conditions, once enough of the ionic lipid has exchanged to overcome long range ionic interactions between the charged lipids associated with the inner leaflets. In these experiments the polymer-lipids were incorporated into the anionic liposomes either by preformulation or by exchange. The systems investigated included 0–10% SBL (MePEGA-2000-DSPE [FIG. 20A, D], ATTA8-DSPE [FIG. 20B, E] and ATTA4-DSPE [FIG. 20C, F]) in POPC/DOPS/SBL (80-n:20:n) vesicles. The experiment (preformulated) was performed with both POPC/stearylamine (95:5; FIG. 20A–C) and POPC/DODAC (95:5; FIG. 20D–F) cationic vesicles. Similar behavior was observed when systems containing exchanged in SBL were used. The effects of environmental factors, such as temperature, were shown to be negligible by repeating the 0% experiment as the first and last experiments in the stearylamine data set (FIG. 20C). Data for the DODAC systems 0% plot (FIGS. 20D–F) were obtained on separate days.

All publications, patents and patent applications mentioned in this specification are herein incorporated by reference into the specification in their entirety for all purposes. Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound of Formula I

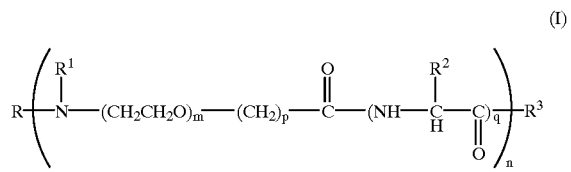

wherein:
R is a member selected from the group consisting of hydrogen, alkyl and acyl;
$R^1$ is a member selected from the group consisting of hydrogen and alkyl;
or optionally,
R and $R^1$ and the nitrogen to which they are bound form an azido moiety;
$R^2$ is a member of the group selected from hydrogen, optionally substituted alky, optionally substituted aryl and a side chain of an amino acid;
$R^3$ is a member selected from the group consisting of hydrogen, halogen, hydroxy, alkoxy, mercapto, hydrazino, amino and $NR^4R^5$, wherein $R^4$ and $R^5$ are independently hydrogen or alkyl;
n is 4 to 80;
m is 2 to 6;
p is 1 to 4; and
q is 0 or 1.

2. A compound according to claim 1, wherein:
R is hydrogen;
$R^1$ is hydrogen;
$R^3$ is a member selected from the group consisting of halogen, hydroxy, alkoxy, amino, mercapto and hydrazino; m is 4; p is 1; q is 0; and n is 8.

3. A compound according to claim 1, wherein:
R, $R^1$ and the nitrogen to which they are bound form an azido moiety; $R^3$ is a member selected from the group consisting of halogen, hydroxy, alkoxy, amino, mercapto and hydrazino; m is 4; p is 1; q is 0; and n is 8.

4. A compound of Formula II:

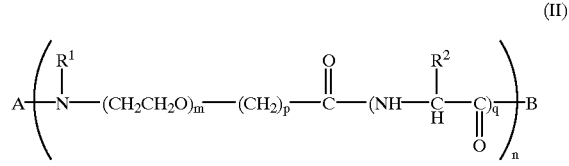

wherein:
$R^1$ is member selected from the group consisting of hydrogen and alkyl;
A is a member selected from the group consisting of hydrogen, alkyl, acyl and a ligand;
or, optionally,
$R^1$, A, and the nitrogen to which they are bound form an azido moiety;
$R^2$ is a member of the group selected from hydrogen, optionally substituted alkyl, optionally substituted aryl and a side chain of an amino acid;
B is a member selected from the group consisting of hydrogen, halogen, hydroxy, alkoxy, amino, $NR^4R^5$, wherein $R^4$ and $R^5$ are independently hydrogen or alkyl, mercapto, hydrazino, diacylglycerolyl, dialkylglycerolyl, N,N-dialkylamino, 1,2-diacyloxy-3-aminopropane, 1,2-dialkyloxy-3-aminopropane and a ligand;

n is 4 to 80;

m is 2 to 6;

p is 1 to 4; and q is 0 or 1.

5. A compound according to claim 4, wherein:

A and B are independently selected from the group consisting of hydrogen and a ligand selected from the group consisting of a lipid, a carrier compound, a bioaffinity compound, an analytically detectable compound, a therapeutically active compound, an enzyme, a protein, an immune stimulator, a radiolabel, a fluorogen, a biotin, a drug, a hapten, DNA, RNA, a polysaccharide, a liposome, an immunoglobulin and a functional group.

6. A compound according to claim 4, wherein n is 8 and m is 4.

7. A compound according to claim 6, wherein B is a lipid.

8. A compound according to claim 7, wherein said lipid is a phospholipid having a polar head group.

9. A compound according to claim 8, wherein B is a phosphatidylethanolamine coupled through a lipid amine group.

10. A compound according to claim 4, wherein B is a phospholipid having two acyl carbon chains with at least one unsaturated bond.

11. A compound according to claim 4, wherein B is a phospholipid having two acyl carbon chains, said acyl carbon chains being saturated.

12. A compound according to claim 4, wherein B is a phosphatidylethanolamine coupled through a lipid amine group, n is 8 and m is 4.

13. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is $NR^4R^5$, wherein $R^4$ is $C_{14}H_{29}$ and $R^5$ is $C_{14}H_{29}$.

14. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is $NR^4R^5$, wherein $R^4$ is $C_{16}H_{33}$ and $R^5$ is $C_{16}H_{33}$.

15. A compound according to claim 4, wherein:

n is 4, wherein for $n^1$: $R^1$, A and the nitrogen to which they are bound form an azido group; m is 4; p is 1; and q is 0; and wherein for $n^2$–$n^4$: $R^1$ is hydrogen, m is 4, p is 1; and q is 0; and B is 1,2-distearoyl-sn-glycero-3-phosphoethanolamine.

16. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is 1,2-dioleoyl-sn-glycero-3-phosphoethanolamine.

17. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is 1,2-distearoyl-sn-glycero-3-phosphoethanolamine.

18. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is 1,2-diacyloxy-3-aminopropane, wherein the acyl groups are $C_{13}H_{27}$.

19. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is 1,2-diacyloxy-3-aminopropane, wherein the acyl groups are $C_{15}H_{31}$.

20. A compound according to claim 4, wherein:

n is 8, wherein for $n^1$: $R^1$, A and the nitrogen to which they are bound form an azido group; m is 4; p is 1; and q is 0; and wherein for $n^2$–$n^8$: $R^1$ is hydrogen, m is 4, p is 1; and q is 0; and B is 1,2-diacyloxy-3-aminopropane, wherein the acyl groups are $C_{17}H_{35}$.

21. A compound of the Formula III (III)

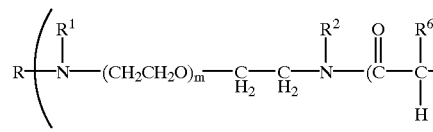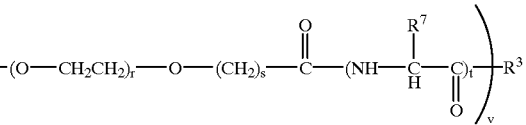

wherein:

R is a member selected from the group consisting of hydrogen, alkyl and acyl;

$R^1$ and $R^2$ are independently selected from the group consisting of hydrogen and alkyl; or, optionally, R, $R^1$, and the nitrogen to which they are bound form an azido moiety;

$R^3$ is a member selected from the group consisting of hydrogen, halogen, hydroxy, alkoxy, mercapto, hydrazino, amino and $NR^4R^5$, wherein $R^4$ and $R^5$ are independently selected from the group consisting of hydrogen and alkyl;

$R^6$ and $R^7$ are independently selected from the group consisting of hydrogen, optionally substituted alkyl or optionally substituted aryl, wherein the substituents include aryl, amine, carboxyl, thiol and hydroxy groups;

v is 2 to 40;

m and r are independently 2 to 6;

x and s are independently 1 to 4; and z and t are independently 0 or 1.

22. A compound according to claim 21, wherein:

R is hydrogen; $R^1$ is hydrogen; and $R^3$ is a member selected from the group consisting of hydrogen, alkyl, and acyl.

23. A compound of Formula IV:

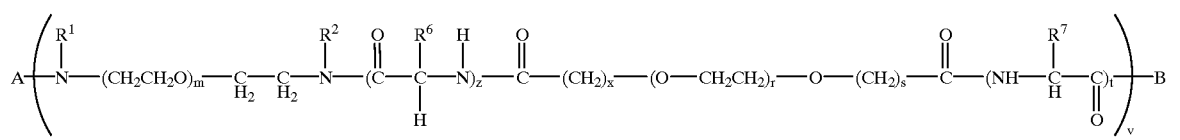

wherein:
- A is selected from the group consisting of hydrogen, alkyl, acyl and a ligand;
- $R^1$ and $R^2$ are independently selected from the group consisting of hydrogen and alkyl;
- $R^6$ and $R^7$ are independently selected from the group consisting of hydrogen, optionally substituted alkyl and optionally substituted aryl, wherein the substituents include aryl, amine, carboxyl, thiol and hydroxy groups;
- B is a member selected from the group consisting of hydrogen, halogen, hydroxy, alkoxy, amino, $NR^4R^5$, wherein $R^4$ and $R^5$ are independently hydrogen and alkyl, mercapto, hydrazino, diacylglycerolyl, dialkylglycerolyl, N,N-dialkylamino, 1,2-diacyloxy-3-aminopropane, 1,2-dialkyloxy-3-aminopropane and a ligand; and
- v is 2 to 40;
- m and r are independently 2 to 6;
- x and s are independently 1 to 4; and
- z and t are independently 0 or 1.

24. A compound according to claim 23, wherein:

A and B are independently selected from the group consisting of hydrogen and a ligand selected from the group consisting of a lipid, a carrier compound, a bioaffinity compound, an analytically detectable compound, a therapeutically active compound, an enzyme, a protein, an immune stimulator, a radiolabel, a fluorogen, a biotin, a drug, a hapten, DNA, RNA, a polysaccharide, a liposome, an immunoglobulin and a functional group.

* * * * *